(12) United States Patent
Fischer et al.

(10) Patent No.: US 7,888,285 B2
(45) Date of Patent: Feb. 15, 2011

(54) 2,4,6-PHENYL SUBSTITUTED CYCLIC KETOENOLS

(75) Inventors: Reiner Fischer, Monheim (DE); Klaus Kunz, Düsseldorf (DE); Stefan Lehr, Liederbach (DE); Michael Ruther, Langenfeld (DE); Udo Schneider, Leverkusen (DE); Markus Dollinger, Leverkusen (DE); Mark Wilhelm Drewes, Langenfeld (DE); Dieter Feucht, Eschborn (DE); Jörg Konze, Köln (DE); Ulrike Wachendorff-Neumann, Neuwied (DE); Guido Bojack, Wiesbaden (DE); Thomas Auler, Leichlingen (DE); Martin Jeffrey Hills, Idstein (DE); Thomas Bretschneider, Lohmar (DE); Olga Malsam, Rösrath (DE); Christoph Erdelen, Leichlingen (DE); Angelika Lubos-Erdelen, legal representative, Leichlingen (DE); Alfred Angermann, Kriftel (DE); Heinz Kehne, Hofheim (DE); Christopher Hugh Rosinger, Hofheim (DE)

(73) Assignee: Bayer CropScience AG, Monheim (DE)

( * ) Notice: Subject to any disclaimer, the term of this patent is extended or adjusted under 35 U.S.C. 154(b) by 1033 days.

(21) Appl. No.: 10/549,074

(22) PCT Filed: Mar. 2, 2004

(86) PCT No.: PCT/EP2004/002053

§ 371 (c)(1),
(2), (4) Date: Feb. 21, 2006

(87) PCT Pub. No.: WO2004/080962

PCT Pub. Date: Sep. 23, 2004

(65) Prior Publication Data

US 2007/0015664 A1 Jan. 18, 2007

(30) Foreign Application Priority Data

Mar. 14, 2003 (DE) .................... 103 11 300

(51) Int. Cl.
*A01N 43/713* (2006.01)
*A01N 43/08* (2006.01)
*C07D 207/46* (2006.01)
*C07D 307/33* (2006.01)

(52) U.S. Cl. .............. 504/138; 504/140; 548/407; 548/543; 548/565; 549/475; 549/477

(58) Field of Classification Search ............... 504/221, 504/283, 289, 292, 299, 138, 140; 544/53; 548/517, 407, 543, 565; 549/60, 62, 313, 549/290, 475, 477
See application file for complete search history.

(56) References Cited

U.S. PATENT DOCUMENTS

| | | | |
|---|---|---|---|
| 3,542,809 A | 11/1970 | Nakanishi | 260/332.2 |
| 4,021,224 A | 5/1977 | Pallos et al. | 71/88 |
| 4,137,070 A | 1/1979 | Pallos et al. | 71/100 |
| 4,175,135 A | 11/1979 | Haines | 424/311 |
| 4,186,130 A | 1/1980 | Teach | 548/215 |
| 4,209,532 A | 6/1980 | Wheeler | 424/331 |
| 4,243,811 A | 1/1981 | Teach | 548/215 |
| 4,256,657 A | 3/1981 | Wheeler | 260/465 D |
| 4,256,658 A | 3/1981 | Wheeler | 260/465 D |
| 4,256,659 A | 3/1981 | Wheeler | 260/465 D |
| 4,257,858 A | 3/1981 | Wheeler | 204/158 R |
| 4,269,618 A | 5/1981 | Pallos et al. | 71/88 |
| 4,283,348 A | 8/1981 | Wheeler | 260/465 D |
| 4,303,669 A | 12/1981 | D'Silva | 424/282 |
| 4,338,122 A | 7/1982 | Wheeler | 71/122 |
| 4,351,666 A | 9/1982 | Koerwer | 71/106 |
| 4,415,352 A | 11/1983 | Pallos et al. | 71/88 |
| 4,415,353 A | 11/1983 | Pallos et al. | 71/100 |
| 4,422,870 A | 12/1983 | Wheeler | 71/106 |
| 4,436,666 A | 3/1984 | Wheeler | 260/455 B |
| 4,526,723 A | 7/1985 | Wheeler et al. | 260/410.5 |
| 4,551,547 A | 11/1985 | Wheeler | 560/255 |
| 4,613,617 A | 9/1986 | Sousa | 514/521 |
| 4,623,727 A | 11/1986 | Hübele | 546/178 |
| 4,632,698 A | 12/1986 | Wheeler | 71/106 |
| 4,639,266 A | 1/1987 | Heubach et al. | 71/92 |
| 4,659,372 A | 4/1987 | Wheeler | 71/106 |
| 4,708,735 A | 11/1987 | Pallos et al. | 71/118 |

(Continued)

FOREIGN PATENT DOCUMENTS

CA 2 382 432 A1 3/2001

(Continued)

OTHER PUBLICATIONS

Cited ref-STN-10549074.*

(Continued)

*Primary Examiner*—Yong Chu
(74) *Attorney, Agent, or Firm*—Richard E. L. Henderson

(57) ABSTRACT

The present invention relates to novel 2,4,6-phenyl-substituted cyclic ketoenols of the formula (I)

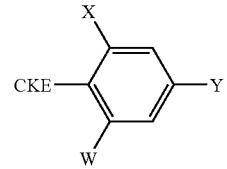

in which W, X, Y and CKE have the meanings given in the disclosure, to a plurality of processes for their preparation and to their use as pesticides and/or herbicides. The invention further relates to selectively herbicidal compositions containing 2,4,6-phenyl-substituted cyclic ketoenols and a compound which improves crop plant tolerance.

11 Claims, No Drawings

U.S. PATENT DOCUMENTS

| | | | | |
|---|---|---|---|---|
| 4,758,264 A | 7/1988 | Hubele | | 71/94 |
| 4,785,105 A | 11/1988 | Hubele | | 546/178 |
| 4,785,106 A | 11/1988 | Hubele | | 546/178 |
| 4,822,884 A | 4/1989 | Hubele | | 546/177 |
| 4,851,033 A | 7/1989 | Hubele | | 71/94 |
| 4,881,966 A | 11/1989 | Nyffeler et al. | | 71/94 |
| 4,891,057 A | 1/1990 | Sohn et al. | | 71/72 |
| 4,902,340 A | 2/1990 | Hubele | | 71/94 |
| 4,925,868 A | 5/1990 | Terao et al. | | 514/425 |
| 4,971,618 A | 11/1990 | Pallos et al. | | 71/93 |
| 4,985,063 A | 1/1991 | Fischer et al. | | 71/88 |
| 5,023,333 A | 6/1991 | Hubele | | 546/175 |
| 5,045,107 A | 9/1991 | Hubele | | 71/94 |
| 5,045,560 A | 9/1991 | Fischer et al. | | 514/425 |
| 5,082,949 A | 1/1992 | Sohn et al. | | 548/378 |
| 5,094,681 A | 3/1992 | Kramer et al. | | 71/88 |
| 5,102,445 A | 4/1992 | Hubele | | 71/94 |
| 5,116,836 A | 5/1992 | Fischer et al. | | 514/224.2 |
| 5,186,737 A | 2/1993 | Fischer et al. | | 504/283 |
| 5,207,817 A | 5/1993 | Krämer et al. | | 504/299 |
| 5,225,434 A | 7/1993 | Bertram et al. | | 514/411 |
| 5,258,527 A | 11/1993 | Krauskopf et al. | | 548/543 |
| 5,262,383 A | 11/1993 | Fischer et al. | | 504/195 |
| 5,314,863 A | 5/1994 | Löher et al. | | 504/100 |
| 5,380,852 A | 1/1995 | Schütze et al. | | 546/174 |
| 5,401,700 A | 3/1995 | Sohn et al. | | 504/106 |
| 5,407,897 A | 4/1995 | Cary et al. | | 504/108 |
| 5,462,913 A | 10/1995 | Fischer et al. | | 504/138 |
| 5,494,890 A | 2/1996 | Cederbaum et al. | | 504/281 |
| 5,504,057 A | 4/1996 | Fischer et al. | | 504/283 |
| 5,506,193 A | 4/1996 | Cederbaum et al. | | 504/282 |
| 5,516,750 A | 5/1996 | Willms et al. | | 504/106 |
| 5,516,918 A | 5/1996 | Cary et al. | | 549/23 |
| 5,565,450 A | 10/1996 | Fischer et al. | | 514/227.2 |
| 5,567,671 A | 10/1996 | Fischer et al. | | 504/283 |
| 5,602,078 A | 2/1997 | Fischer et al. | | 504/283 |
| 5,610,122 A | 3/1997 | Fischer et al. | | 504/251 |
| 5,622,917 A | 4/1997 | Fischer et al. | | 504/283 |
| 5,677,449 A | 10/1997 | Fischer et al. | | 544/165 |
| 5,696,050 A | 12/1997 | Cary et al. | | 504/108 |
| 5,700,758 A | 12/1997 | Rösch et al. | | 504/106 |
| 5,703,008 A | 12/1997 | Rösch et al. | | 504/106 |
| 5,719,310 A | 2/1998 | Fischer et al. | | 560/83 |
| 5,739,079 A | 4/1998 | Holdgrün et al. | | 504/103 |
| 5,808,135 A | 9/1998 | Fischer et al. | | 560/129 |
| 5,830,825 A | 11/1998 | Fischer et al. | | 504/130 |
| 5,830,826 A | 11/1998 | Fischer et al. | | 504/195 |
| 5,840,661 A | 11/1998 | Fischer et al. | | 504/348 |
| 5,847,211 A | 12/1998 | Fischer et al. | | 564/123 |
| 5,922,732 A | 7/1999 | Urch et al. | | 514/304 |
| 5,945,444 A | 8/1999 | Fischer et al. | | 514/445 |
| 5,945,541 A | 8/1999 | Sohn et al. | | 548/374.1 |
| 5,968,947 A | 10/1999 | Urch et al. | | 514/299 |
| 5,977,029 A | 11/1999 | Fischer et al. | | 504/283 |
| 5,994,274 A | 11/1999 | Fischer et al. | | 504/282 |
| 6,051,723 A | 4/2000 | Fischer et al. | | 549/420 |
| 6,071,937 A | 6/2000 | Bretschneider et al. | | 514/336 |
| 6,093,726 A | 7/2000 | Urch et al. | | 514/299 |
| 6,110,872 A | 8/2000 | Lieb et al. | | 504/284 |
| 6,114,374 A | 9/2000 | Lieb et al. | | 514/424 |
| 6,133,246 A | 10/2000 | Lieb et al. | | 514/299 |
| 6,140,358 A * | 10/2000 | Lieb et al. | | 514/425 |
| 6,150,304 A | 11/2000 | Fischer et al. | | 504/309 |
| 6,172,255 B1 | 1/2001 | Fischer et al. | | 560/24 |
| 6,174,894 B1 | 1/2001 | Urch et al. | | 514/299 |
| 6,177,442 B1 | 1/2001 | Urch et al. | | 514/299 |
| 6,200,932 B1 | 3/2001 | Fischer et al. | | 504/225 |
| 6,207,676 B1 | 3/2001 | Urch et al. | | 514/304 |
| 6,235,680 B1 | 5/2001 | Ziemer et al. | | 504/112 |
| 6,251,827 B1 | 6/2001 | Ziemer et al. | | 504/130 |
| 6,251,830 B1 | 6/2001 | Fischer et al. | | 504/251 |
| 6,251,833 B1 | 6/2001 | Erdelen et al. | | 504/348 |
| 6,255,342 B1 | 7/2001 | Lieb et al. | | 514/533 |
| 6,271,180 B2 * | 8/2001 | Lieb et al. | | 504/292 |
| 6,291,474 B1 | 9/2001 | Brightwell et al. | | 514/299 |
| 6,358,887 B1 | 3/2002 | Fischer et al. | | 504/284 |
| 6,359,151 B2 | 3/2002 | Lieb et al. | | 549/265 |
| 6,388,123 B1 * | 5/2002 | Lieb et al. | | 560/76 |
| 6,391,883 B1 | 5/2002 | Urch et al. | | 514/255 |
| 6,410,480 B1 | 6/2002 | Mühlebach et al. | | 504/105 |
| 6,417,370 B1 | 7/2002 | Lieb et al. | | 548/408 |
| 6,451,843 B1 | 9/2002 | Lieb et al. | | 514/422 |
| 6,458,965 B1 | 10/2002 | Lieb et al. | | 548/408 |
| 6,469,196 B2 | 10/2002 | Fischer et al. | | 560/105 |
| 6,472,419 B1 | 10/2002 | Fischer et al. | | 514/425 |
| 6,482,947 B1 | 11/2002 | Holdgrün et al. | | 544/239 |
| 6,486,343 B1 * | 11/2002 | Lieb et al. | | 560/39 |
| 6,504,036 B1 | 1/2003 | Lieb et al. | | 549/265 |
| 6,511,940 B1 | 1/2003 | Ziemer et al. | | 504/118 |
| 6,511,942 B1 | 1/2003 | Lieb et al. | | 504/299 |
| 6,555,499 B1 | 4/2003 | Glock et al. | | 504/130 |
| 6,569,810 B1 | 5/2003 | Fischer et al. | | 504/290 |
| 6,573,275 B1 | 6/2003 | Urch et al. | | 514/304 |
| 6,576,771 B1 | 6/2003 | Bretschneider et al. | | 549/24 |
| 6,596,873 B1 | 7/2003 | Lieb et al. | | 546/256 |
| 6,693,092 B2 | 2/2004 | Lieb et al. | | 514/183 |
| 6,716,832 B2 | 4/2004 | Lieb et al. | | 514/183 |
| 6,746,990 B2 | 6/2004 | Fischer et al. | | 504/299 |
| 6,759,548 B2 | 7/2004 | Fischer et al. | | 560/81 |
| 6,806,264 B2 | 10/2004 | Lieb et al. | | 514/183 |
| 6,894,005 B1 | 5/2005 | Maetzke et al. | | 504/218 |
| 6,933,261 B2 | 8/2005 | Lieb et al. | | 504/298 |
| 6,962,894 B1 | 11/2005 | Glock | | 504/238 |
| 2001/0004629 A1 | 6/2001 | Lieb et al. | | 504/292 |
| 2002/0010204 A1 | 1/2002 | Lieb et al. | | 514/424 |
| 2002/0022575 A1 | 2/2002 | Fischer et al. | | 504/221 |
| 2002/0061913 A1 | 5/2002 | Urch et al. | | 514/366 |
| 2002/0188136 A1 | 12/2002 | Lieb et al. | | 548/368.4 |
| 2003/0045432 A1 | 3/2003 | Fischer et al. | | 504/221 |
| 2003/0073851 A1 | 4/2003 | Lieb et al. | | 548/366.4 |
| 2003/0096806 A1 | 5/2003 | Lieb et al. | | 514/212.01 |
| 2003/0144504 A1 | 7/2003 | Fischer et al. | | 544/54 |
| 2003/0171219 A1 | 9/2003 | Lieb et al. | | 504/221 |
| 2003/0171220 A1 | 9/2003 | Ziemer et al. | | 504/271 |
| 2003/0216260 A1 | 11/2003 | Ruther et al. | | 504/283 |
| 2004/0019061 A1 | 1/2004 | Fischer et al. | | 514/256 |
| 2004/0127365 A1 | 7/2004 | Lieb et al. | | 504/282 |
| 2004/0167031 A1 | 8/2004 | Lieb et al. | | 504/308 |
| 2004/0266624 A1 | 12/2004 | Hofer | | 504/282 |
| 2005/0038021 A1 | 2/2005 | Lieb et al. | | 514/227.5 |
| 2005/0090399 A1 | 4/2005 | Friedmann et al. | | 504/282 |
| 2005/0164883 A1 | 7/2005 | Maetzke et al. | | 504/131 |
| 2005/0164886 A1 | 7/2005 | Glock | | 504/282 |
| 2005/0187110 A1 | 8/2005 | Maetzke et al. | | 504/221 |

FOREIGN PATENT DOCUMENTS

| | | |
|---|---|---|
| CA | 2 513 501 | 8/2004 |
| EP | 346 620 A1 | 12/1989 |
| EP | 0 442 077 | 8/1991 |
| EP | 0 508 126 | 10/1992 |
| EP | 0 521 334 | 1/1993 |
| EP | 0 588 137 | 3/1994 |
| GB | 2 266 888 A | 11/1993 |
| JP | 2000-53670 | 2/2000 |
| WO | 94/29268 A1 | 12/1994 |
| WO | 95/01971 | 1/1995 |
| WO | 96/02539 A1 | 2/1996 |
| WO | 96/11574 | 4/1996 |
| WO | 96/21652 A1 | 7/1996 |
| WO | 96/35664 | 11/1996 |
| WO | 98/25928 | 6/1998 |
| WO | 99/16748 | 4/1999 |
| WO | 99/24437 | 5/1999 |

| | | |
|---|---|---|
| WO | 01/17351 A1 | 2/2001 |
| WO | 01/23354 | 4/2001 |
| WO | 03013249 | 2/2003 |

OTHER PUBLICATIONS

Chem. Pharm. Bull., 15, (month unavailable) 1967, pp. 1120-1122, Seikichi Suzuki et al, "Studies on Antiviral Agents, IV. Biological Activity of Tenuazonic Acid Derivatives".

Liebigs Ann. Chem., (month unavailable) 1985, pp. 1095-1098, Roland Schmierer et al, "Cyclisierung von N-Acylalanin- und N-Acylglycinestern".

J. Chem. Soc. Perkin Trans. 1, (month unavailable) 1985, pp. 1567-1576, Alexander C. Campbell et al. "Synthesis of (E)- and (Z)-Pulvinones".

Arch. Pharm., 309, (month unavailable) 1976, pp. 558-564, Ali M. Chirazi et al, "Synthesen von Heterocyclen, 184 Zur Synthese von Kawalactonderivaten".

Chem. Ber., 91, (month unavailable) 1958, p. 2849, Karl-Heinz Boltze et al, "Zur Synthese 3-substituierter 4-Hydroxy-pyrone-(2), I Ringschlüsse mit Malonsäure-dichloriden".

Monatsh, 95, (month unavailable) 1964, pp. 147-155, E. Ziegler et al, "Synthesen von Heterocyclen, 52. Mitt.: Über Derivate des 2-Phenyl-4-hydroxy-[1,3-thiazinons-(6)]".

J. Heterocycl. Chem. 10, Apr. 1973, pp. 223-224, Roger Ketcham et al, "Synthesis of Heterocycles. 174 (1,2) Substituted Thiazines and Bisthiazinyls from Dithiooxamide and Trichlorophenyl Malonates".

Tetrahedron, vol. 48, No. 36, (month unavailable) 1992, pp. 7519-7526, Jason Micklefield et al, "Alkylation and Acylation of 5-Phenylsulphonyl- and 5-Cyanobutyrolactones".

J. Chem. Soc. (C), (month unavailable) 1967, pp. 405-409, R.L. Edwards et al, Constituents of the Higher Fungi. Part IV. Involutin, a Diphenylcyclopenteneone from *Paxillus involutus* (Oeder ex Fries).

J. Ecomonic Entomology, vol. 66, No. 2, Apr. 1973, pp. 584-586, A.A. Sousa et al, "Esters of 3-Hydroxy-2- Arylindones, a New Class of Acaricide".

J. Org. Chem., 44, No. 26, (month unavailable) 1979, pp. 4906-4912, Thomas N. Wheeler, "Novel Photochemical Synthesis of 2-Aryl-1,3-cyclohexanediones".

Chemical Reviews, 52, (month unavailable) 1953, pp. 237-416, Norman O.V. Sonntag, "The Reactions of Aliphatic Acid Chlorides".

Indian J. Chem., vol. 6, Jul. 1968, pp. 341-345, Bhabatosh Bhattacharya, "Isoquinoline Derivatives: Part XVIII—Formation of I-Alkyl-(or alkaryl or aryl)-3-methyl-7-chloro-(or 5-chloro)-isoquinolines".

Chem. Ind. London, Nov. 9, 1968, p. 1568, H.R. Harrison et al, "Use of molecular sieves in the methyl esterification of carboxylic acids".

Organikum, (month unavailable) 1977, p. 505, "Reaktionen von Carbonsäuren und Carbonsäurederivaten mit Basen".

Houben-Weyl Methoden der Organischen Chemie [Methods in Organic Chemistry] vol. 8, (month unavailable) 1952, pp. 467-470, H. Henecka, "Carbonsäuren".

Ann. Chim., (month unavailable) 1970, pp. 11-22, P.L. Compagnon et M. Miocque, "Addition Des Réactifs Nucléophiles Sur La Triple Liaison Nitrile I.—Addition Des Hydrures, De L'eau, De L'Hydrogène Sulfuré Et De L'Hydrogène Sélénié".

Ann. Chim., (month unavailable) 1970, pp. 23-38, P.L. Compagnon et M. Miocque, "Addition Des Réactifs Nucléophiles Sur La Triple Liaison Nitrile II.—Addition Des Alcools, Des Composés Azotés, Des Organométalliques; Condensation De Plusieurs Molécules De Nitriles".

J. Chem. Soc., (month unavailable) 1961, pp. 4372-4379, L. Munday, "Amino-acids of the Cyclohexane Series. Part I".

Can. J. Chem., vol. 53, (month unavailable) 1975, pp. 3339-3350, John T. Edward et al, "Stereochemistry of the Bucherer-Bergs and Strecker Reactions of 4-*tert*-Butylcyclohexanone".

J. Chem. Soc., Chem. Commun., (month unavailable) 1987, pp. 1228-1230, Mark S. Chambers et al, "An Asymmetric Synthesis of Thiotetronic Acids using Chirality Transfer via an Allyl Xanthate-to-Dithiocarbonate Rearrangement. X-Ray Crystal Structure of (5R)-2,5-Dihydro-4-hydroxy-5-methyl-3-phenyl-5-prop-1'-enyl-2-oxothiophene".

Organic Preparations and Procedures Int., 7(4), (month unavailable) 1975, pp. 155-158, "Synthesis of Chlorocarbonyl Ketenes".

Organikum, (month unavailable) 1977, pp. 517-518, "Reaktionen von Carbonsäuren und Carbonsäurederivaten mit Basen".

Tetrahedron Letters, vol. 27, No. 24, (month unavailable) 1986, pp. 2763-2766, Enrico Baciocchi et al, "Dimethyl Arylmalonates from Cerium(IV) Ammonium Nitrate Promoted Reactions of Dimethyl Malonate with Aromatic Compounds in Methanol".

Organikum, VEB, (month unavailable) 1977, p. 587-589, "Esterkondensation".

Organikum, 15$^{th}$ ed., (month unavailable) 1977, p. 499, "Reaktionen mit metallorganischen Verbindungen".

Organikum 15$^{th}$ ed., (month unavailable) 1977, p. 519-521, "Reaktionen vinyloger Elektronendonorverbindungen".

Justus Liebigs Annalen Der Chemie, 585, (month unavailable) 1954, pp. 1-15 Heinz Dannenberg et al, "Versuche zur Synthese des "Steranthrens"III. 3,4-Aceperinaphthan und 6,7-Aceperinaphthan".

Reaktionen der organischen Synthese [Reactions in organic synthesis], (month unavailable) 1978, pp. 212 and 513-515, C. Ferris, "Organische Reaktionen, nach Reaktionstypen geordner".

Liebigs Ann. Chem., 443, (month unavailable) 1925, pp. 242-262, Otto Diels et al, "Über das aus Cyclopentadien und Azoester entstehende Endomethylen-piperidazin und seine Überführung in 1,3-Diamino-cyclopentan".

Chem. Ber. 98, (month unavailable) 1965, pp. 2551-2555, Rainer Askani, "Zur Reaktion von Cyclohexadien-(1,3) mit Azodicarbonsäure-diäthylester".

Chem. Ind., 37, (month unavailable) 1985, pp. 730-732, Harry R. Ungerer, "Schiffsfarben—eine Spezialität der seenahen Lackindustrie".

* cited by examiner

2,4,6-PHENYL SUBSTITUTED CYCLIC KETOENOLS

The present patent application has been filed under 35 U.S.C. 371 as a national stage application of PCT/EP2004/002053, filed Mar. 2, 2004, which was published in German as International Patent Publication WO 2004/080962 on Sep. 23, 2004, and is entitled to the right of priority of German Patent Application 103 11 300.2, filed Mar. 14, 2003.

The present invention relates to new 2,4,6-phenyl-substituted cyclic ketoenols, to a plurality of processes for their preparation, and to their use as pesticides and/or herbicides. The invention furthermore relates to selectively herbicidal compositions comprising firstly 2,4,6-phenyl-substituted cyclic ketoenols and secondly a compound which improves crop plant tolerance.

Pharmaceutical properties have been previously described of 3-acyl-pyrrolidine-2,4-diones (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-aryl-pyrrolidine-2,4-diones), of which, however, no herbicidal, insecticidal or acaricidal action has been disclosed. Unsubstituted, bicyclic 3-arylpyrrolidine-2,4-dione derivatives (EP-A-355 599, EP415 211 and JP-A-12-053 670) and substituted monocyclic 3-arylpyrrolidine-2,4-dione derivatives (EP-A-377 893 and EP-A-442 077) having a herbicidal, insecticidal or acaricidal action have been disclosed.

There have also been disclosed polycyclic 3-arylpyrrolidine-2,4-dione derivatives (EP-A-442 073) and 1H-arylpyrrolidine-dione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275 WO 98/05638, WO 98/06721, WO 98/25928, WO 99/16748, WO 99/24437, WO 99/43649, WO 99/48869 and WO 99/55673, WO 01/17972, WO 01/23354, WO 01/74770.

It has been disclosed that certain substituted $\Delta^3$-dihydrofuran-2-one derivatives have herbicidal properties (cf. DE-A-4 014 420). The synthesis of the tetronic acid derivatives used as starting compounds (such as, for example, 3-(2-methyl-phenyl)-4-hydroxy-5-(4-fluorophenyl)-$\Delta^3$-dihydrofuran-2-one) is also described in DE-A-4 014 420. Compounds of a similar structure without any mention of an insecticidal and/or acaricidal activity are known from the publication Campbell et al., J. Chem. Soc., Perkin Trans. 1, 1985, (8) 1567-76. 3-Aryl-$\Delta^3$-dihydrofuranone derivatives having herbicidal, acaricidal and insecticidal properties are furthermore disclosed in EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354 and WO 01/74770. 3-Aryl-$\Delta^3$-dihydrothiophenone derivatives are also known (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354 and WO 01/74770).

Certain phenyl-pyrone derivatives which are unsubstituted in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849), a possible use of these compounds as pesticides not being mentioned. Phenyl-pyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972 and WO 01/74770.

Certain 5-phenyl-1,3-thiazine derivatives which are unsubstituted in the phenyl ring have already been disclosed (cf. E. Ziegler and E. Steiner, Monatsh. 95, 147 (1964), R. Ketcham. T. Kappe and E. Ziegler, J. Heterocycl. Chem. 10, 223 (1973)), a possible use of these compounds as pesticides not being mentioned. 5-Phenyl-1,3-thiazine derivatives which are substituted in the phenyl ring and have a herbicidal, acaricidal and insecticidal action are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972 and WO 01/74770.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698, WO 96/01 798; WO 96/03 366, WO 97/14 667 and also WO 98/39281, WO 99/43649, WO 99/48869, WO 99/55673, WO 01/17972 and WO 01/74770). Moreover, compounds with similar substitutions are known; 3-hydroxy-5,5-dimethyl-2-phenylcyclopent-2-en-1-one from the publication Micklefield et al., Tetrahedron, (1992), 7519-26 and the natural product involutin (–)-cis-5-(3,4-dihydroxyphenyl)-3,4-dihydroxy-2-(4-hydroxyphenyl)-cyclopent-2-en-one from the publication Edwards et al., J. Chem. Soc. S, (1967), 405-9. An insecticidal or acaricidal activity is not described. Moreover, 2-(2,4,6-trimethylphenyl)-1,3-indanedione is known from the publication J. Economic Entomology, 66, (1973), 584 and the Offenlegungsschrift DE-A-2 361 084, with herbicidal and acaricidal activities being detailed.

It is known that certain substituted 2-arylcyclohexanediones have herbicidal, insecticidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673, WO 01/17972 and WO 01/74770).

It is known that certain substituted 4-aryl-pyrazolidine-3,5-diones have acaricidal, insecticidal and herbicidal properties (cf., for example, WO 92/16 510, EP-A-508 126, WO 96/11 574, WO 96/21 652, WO 99/47525, WO 01/17351, WO 01/17352, WO 01/17 353, WO 01/17 972, WO 01/17 973, WO 03/028 466 and WO 03/062 244).

However, the activity and range of action of these compounds is not always entirely satisfactory, in particular when low rates and concentrations are applied. Furthermore, these compounds are not always sufficiently well tolerated by plants.

There have now been found new compounds of the formula (I)

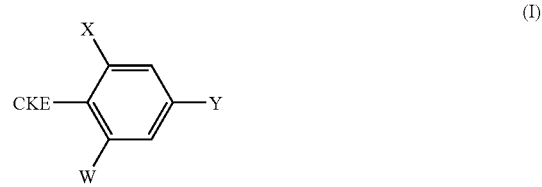

in which

W represents alkoxy, halogenoalkoxy, alkoxyalkyloxy, alkoxy-bis-alkyloxy or optionally substituted cycloalkylalkanediyloxy, which can optionally be interrupted by hetero atoms, X represents alkyl, Y represents chlorine, bromine or iodine, CKE represents one of the groups

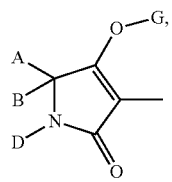 (1)

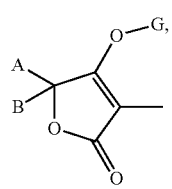 (2)

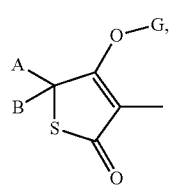 (3)

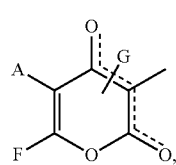 (4)

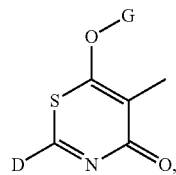 (5)

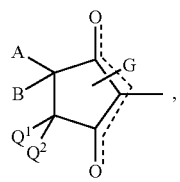 (6)

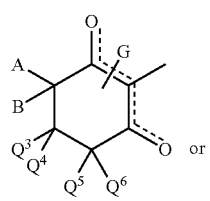 (7)

or

-continued

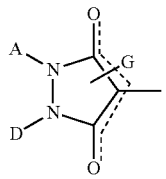 (8)

in which

A represents hydrogen, or represents alkyl, alkenyl, alkoxyalkyl or alkylthioalkyl, each of which is optionally substituted by halogen, or represents saturated or unsaturated, optionally substituted cycloalkyl in which at least one ring atom is optionally replaced by a hetero atom, or represents aryl, arylalkyl or hetaryl, each of which is optionally substituted by halogen, alkyl, halogenoalkyl, alkoxy, halogenoalkoxy, cyano or nitro, B represents hydrogen, alkyl or alkoxyalkyl, or A and B together with the carbon atom to which they are bonded represent a saturated or unsaturated, unsubstituted or substituted cycle which optionally contains at least one hetero atom, D represents hydrogen or an optionally substituted radical from the series consisting of alkyl, alkenyl, alkinyl, alkoxyalkyl, saturated or unsaturated cycloalkyl in which optionally one or more ring members are replaced by hetero atoms; arylalkyl, aryl, hetarylalkyl or hetaryl, or A and D together with the atoms to which they are bonded represent a saturated or unsaturated cycle which is unsubstituted or substituted in the A, D moiety and which optionally contains at least one (in the case of CKE=8, a further) hetero atom, or A and $Q^1$ together represent alkanediyl or alkenediyl which are optionally substituted by hydroxyl or by in each case optionally substituted alkyl, alkoxy, alkylthio, cycloalkyl, benzyloxy or aryl, or $Q^1$ represents hydrogen or alkyl, $Q^2$, $Q^4$, $Q^5$ and $Q^6$ independently of one another represent hydrogen or alkyl, $Q^3$ represents hydrogen, optionally substituted alkyl, alkoxyalkyl, alkylthioalkyl, optionally substituted cycloalkyl (in which a methylene group is optionally replaced by oxygen or sulphur) or optionally substituted phenyl, or $Q^3$ and $Q^4$ together with the carbon atom to which they are bonded represent a saturated or unsaturated, unsubstituted or substituted cycle which optionally contains a hetero atom, G represents hydrogen (a) or one of the groups

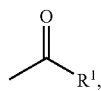 (b)

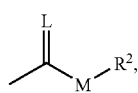 (c)

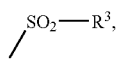 (d)

-continued

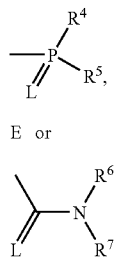
(e)

E or
(f)

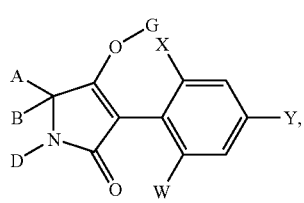
(g)

where

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, each of which is optionally substituted by halogen, or represents cycloalkyl which can be interrupted by at least one hetero atom and which is optionally substituted by halogen, alkyl or alkoxy, or represents in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, each of which is optionally substituted by halogen, or represents in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, each of which is optionally substituted by halogen, or represent in each case optionally substituted phenyl, benzyl, phenoxy or phenylthio, $R^6$ and $R^7$ independently of one another represent hydrogen, or represent alkyl, cycloalkyl, alkenyl, alkoxy or alkoxyalkyl, each of which is optionally substituted by halogen, or represent optionally substituted phenyl, or represent optionally substituted benzyl, or together with the N atom to which they are bonded represent a cycle which is optionally interrupted by oxygen or sulphur.

Depending on the nature of the substituents also, the compounds of the formula (I) can be present in the form of geometric and/or optical isomers or variously composed isomer mixtures, which can optionally be separated in the customary manner. The present invention relates to the pure isomers and also to the isomer mixtures, to their preparation, their use, and to compositions comprising them. However, the following text will always mention compounds of the formula (I), for the sake of simplicity, even though this is to be understood as meaning the pure compounds and, if appropriate, also mixtures containing various proportions of isomeric compounds.

Taking into consideration the meanings (1) to (8) of the CKE group, the following main structures (I-1) to (I-8) result:

(I-1)

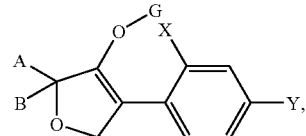

(I-2)

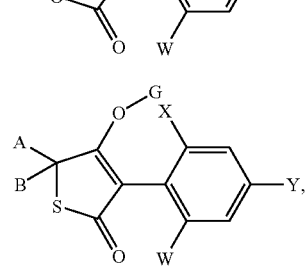

(I-3)

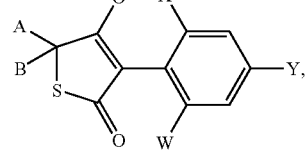

(I-4)

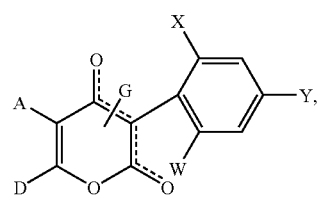

(I-5)

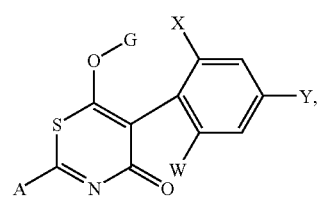

(I-6)

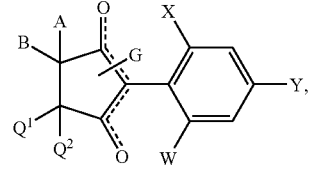

(I-7)

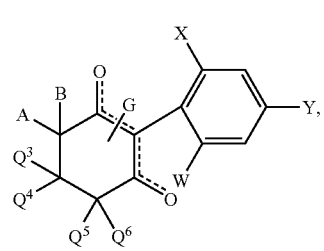

(I-8)

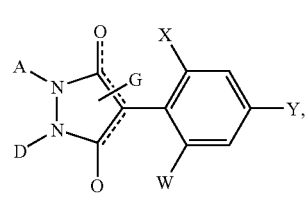

in which

A, B, D, G, $Q^1$, $Q^2$, $Q^3$, $Q^4$, $Q^5$, $Q^6$, W, X and Y have the abovementioned meanings.

Taking into consideration the various meanings (a), (b), (c), (d), (e), (f) and (g) of group G, the following main structures (I-1-a) to (I-1-g) result if CKE represents group (1)

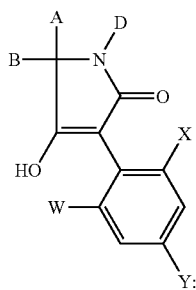
(I-1-a)
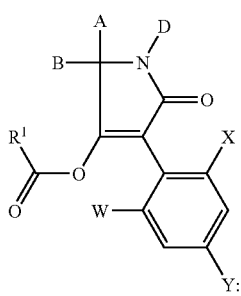
(I-1-b)
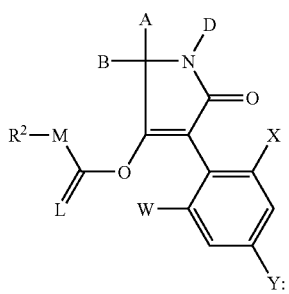
(I-1-c)
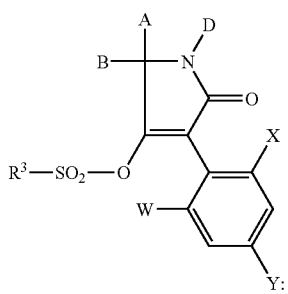
(I-1-d)
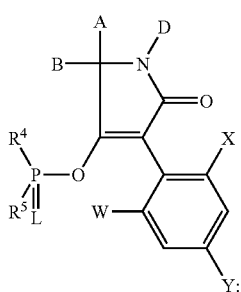
(I-1-e)
-continued
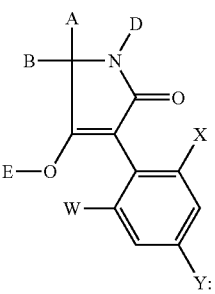
(I-1-f)
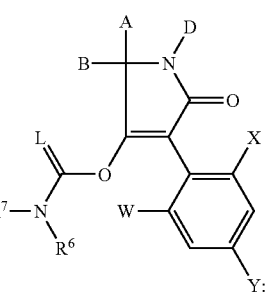
(I-1-g)
in which
A, B, D, E, L, M, W, X, Y, $R^1$, $R^2$, $R^3$, $R^4$, $R^5$, $R^6$ and $R^7$ have the abovementioned meanings.
Taking into consideration the various meanings (a), (b), (c), (d), (e), (f) and (g) of group G, the following main structures (I-2-a) to (I-2-g) result if CKE represents group (2)
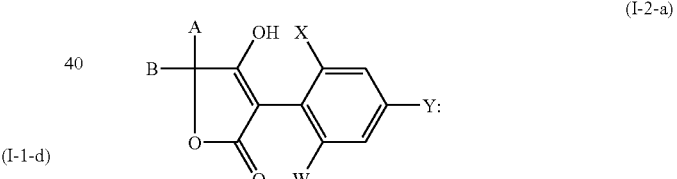
(I-2-a)
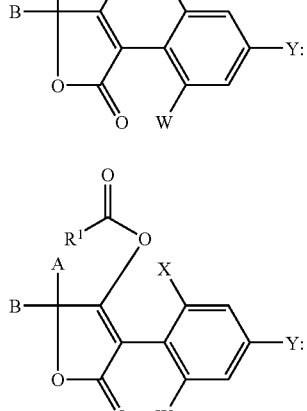
(I-2-b)
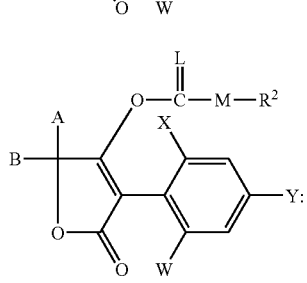
(I-2-c)

-continued

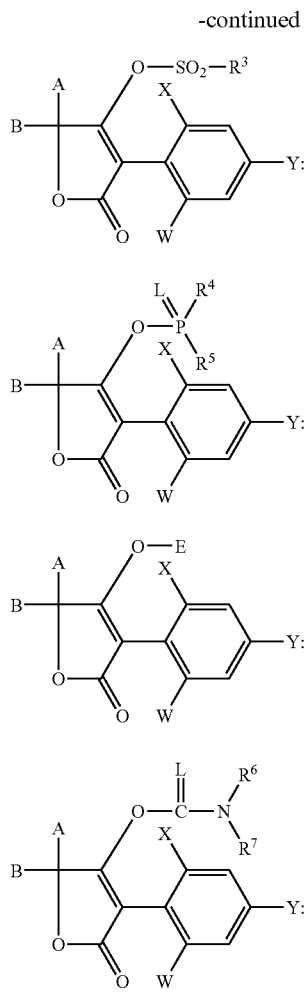

(I-2-d)
(I-2-e)
(I-2-f)
(I-2-g)

in which
A, B, E, L, M, W, X, Y, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-3-a) to (I-3-g) result if CKE represents group (3)

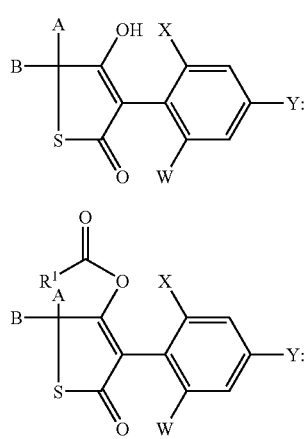

(I-3-a)
(I-3-b)

-continued (I-3-c)
(I-3-d)
(I-3e)
(I-3-f)
(I-3-g)

in which
A, B, E, L, M, W, X, Y, $R^1$, $R^2$, $R^3$, $R^4$, $R^5$, $R^6$ and $R^7$ have the abovementioned meanings.

Depending on the position of the substituent G, the compounds of the formula (I-4) can exist in the two isomeric forms of the formulae (I-4-A) and (I-4-B)

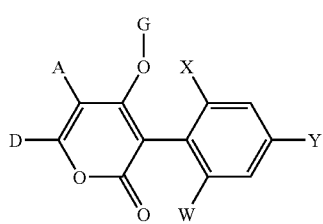

(I-4-A)

-continued (I-4-B)

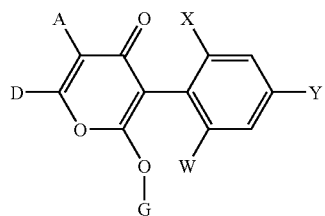

which is intended to be expressed by the broken line in formula (I-4).

The compounds of the formulae (I-4-A) and (I-4-B) can exist as mixtures and also in the form of their pure isomers. If appropriate, mixtures of the compounds of the formulae (I-4-A) and (I-4-B) can be separated in a manner known per se using physical methods, for example by chromatographic methods.

For reasons of improved clarity, the following text will always mention only one of the isomers which are possible. This does not exclude the fact that the compounds can be present, if appropriate, in the form of the isomer mixtures or in the respective other isomeric form.

Taking into consideration the various meanings (a), (b), (c), (d), (e), (f) and (g) of group G, the following main structures (I-4-a) to (I-4-g) result if CKE represents group (4)

(I-4-a)

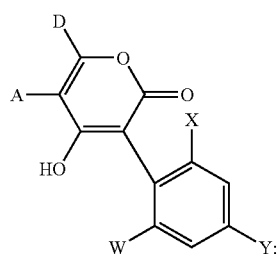

(I-4-b)

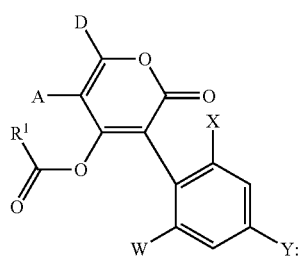

(I-4-c)

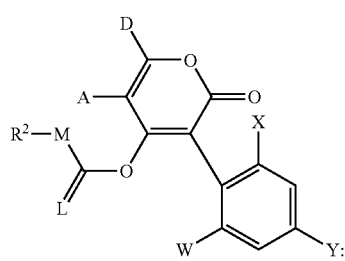

(I-4-d)

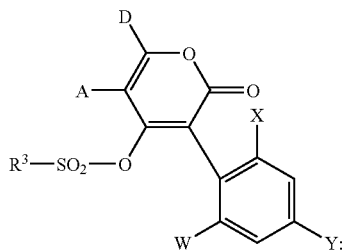

(I-4-e)

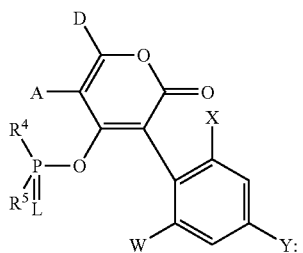

(I-4-f)

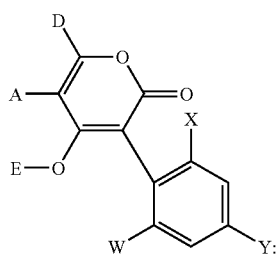

(I-4-g)

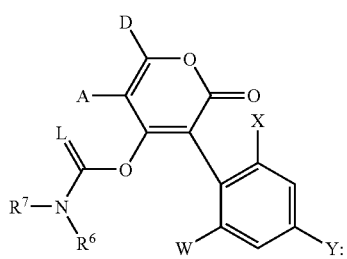

in which

A, D, E, L, M, W, X, Y, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-5-a) to (I-5-g) result if CKE represents group (5)

(I-5-a)

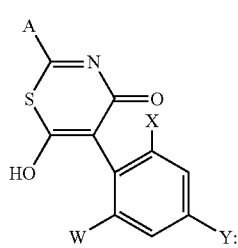

-continued

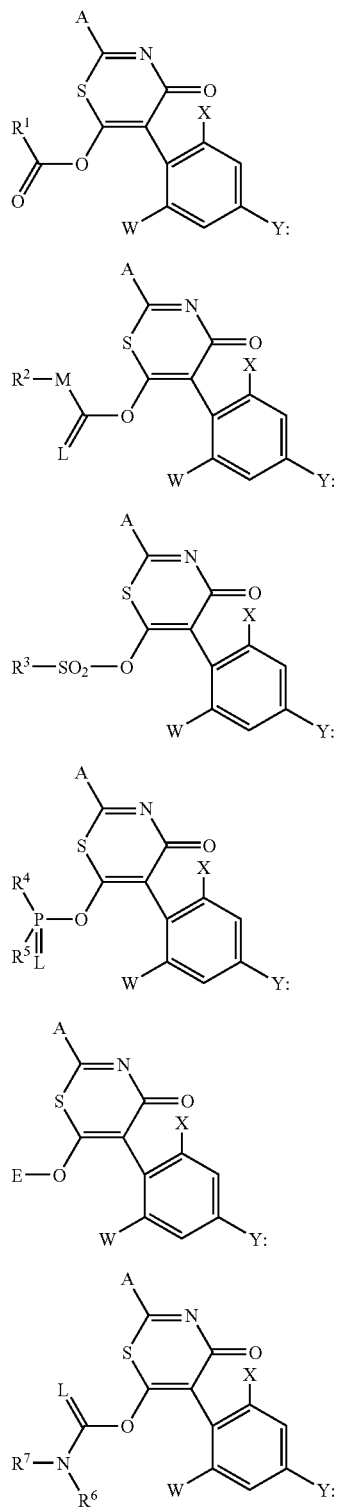

(I-5-b)

(I-5-c)

(I-5-d)

(I-5-f)

(I-5-g)

in which
A, E, L, M, W, X, Y, R$^1$, R$^2$, R$^3$, R$^4$, R$^5$, R$^6$ and R$^7$ have the abovementioned meanings.

Depending on the position of the substituent G, the compounds of the formula (I-6) can exist in the two isomeric forms of the formulae (I-6-A) and (I-6-B)

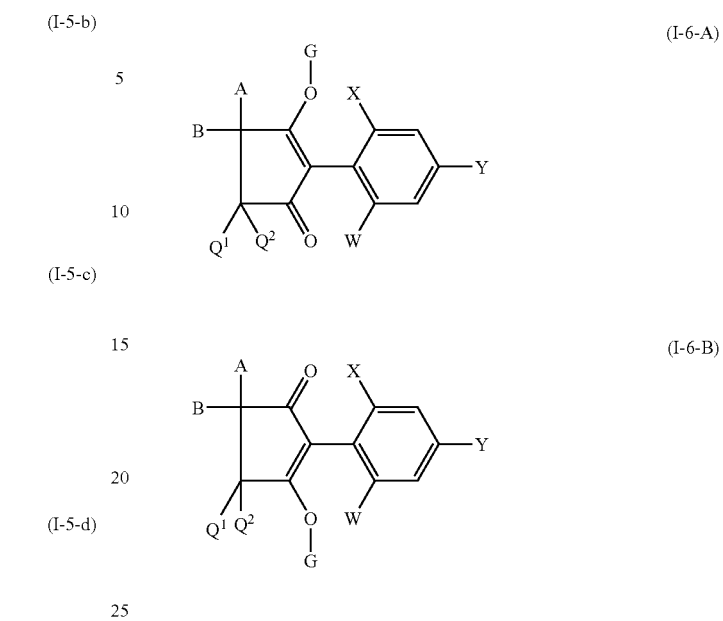

(I-6-A)

(I-6-B)

which is intended to be expressed by the broken line in formula (I).

The compounds of the formulae (I-6-A) and (I-6-B) can exist as mixtures and also in the form of their pure isomers. If appropriate, mixtures of the compounds of the formulae (I-6-A) and (I-6-B) can be separated using physical methods, for example by chromatographic methods.

For reasons of improved clarity, the following text will always mention only one of the isomers which are possible. This does not exclude the fact that the compounds can be present, if appropriate, in the form of the isomer mixtures or in the respective other isomeric form.

Taking into consideration the various meanings (a), (b), (c), (d), (e), (f) and (g) of group G, the following main structures (I-6-a) to (I-6-g) result:

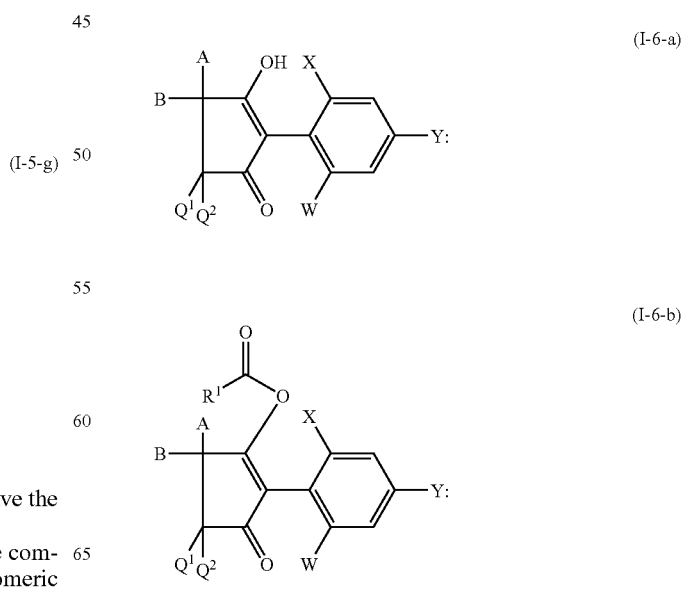

(I-6-a)

(I-6-b)

-continued

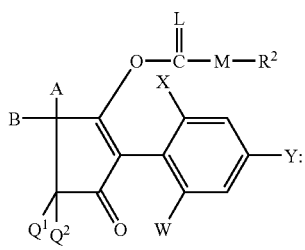 (I-6-c)

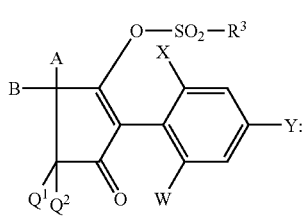 (I-6-d)

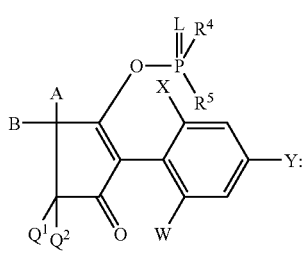 (I-6-e)

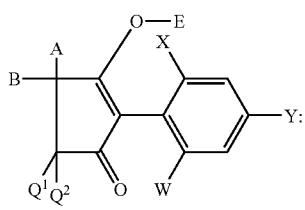 (I-6-f)

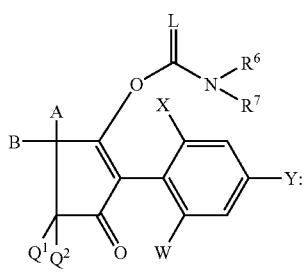 (I-6-g)

in which
A, B, $Q^1$, $Q^2$, E, L, M, W, X, Y, $R^1$, $R^2$, $R^3$, $R^4$, $R^5$, $R^6$ and $R^7$
have the abovementioned meanings.

Depending on the position of the substituent G, the compounds of the formula (I-7) can exist in the two isomeric forms of the formulae (I-7-A) and (I-7-B), which is intended to be expressed by the broken line in formula (I-7):

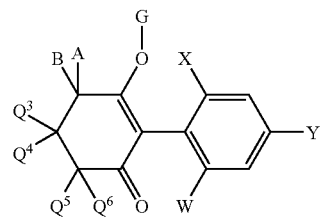 (I-7-A)

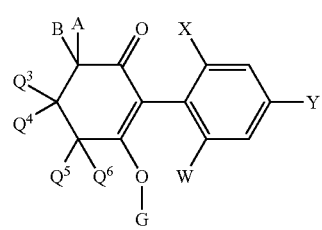 (I-7-B)

The compounds of the formulae (I-7-A) and (I-7-B) can exist as mixtures and also in the form of their pure isomers. If appropriate, mixtures of the compounds of the formulae (I-7-A) and (I-7-B) can be separated using physical methods, for example by chromatographic methods.

For reasons of improved clarity, the following text will always mention only one of the isomers which are possible. This includes the fact that the compound in question can be present, if appropriate, in the form of an isomer mixture or in the respective other isomeric form.

Taking into consideration the various meanings (a), (b), (c), (d), (e), (f) and (g) of group G, the following main structures (I-7-a) to (I-7-g) result:

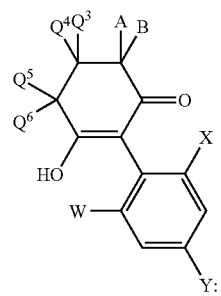 (I-7-a)

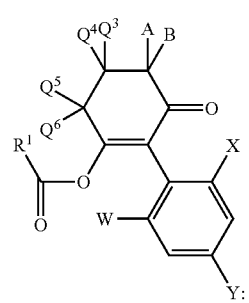 (I-7-b)

-continued

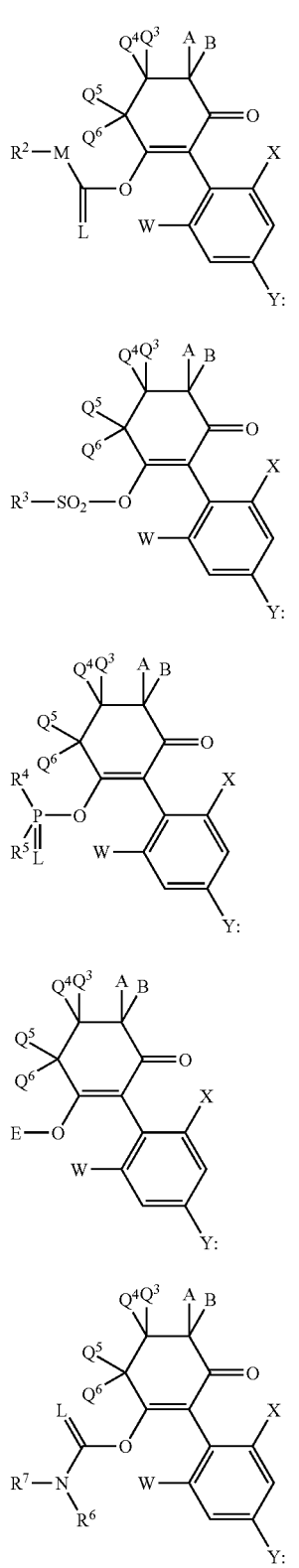

(I-7-c)

(I-7-d)

(I-7-e)

(I-7-f)

(I-7-g)

in which
A, B, E, L, M, $Q^3$, $Q^4$, $Q^5$, $Q^6$, W, X, Y, $R^1$, $R^2$, $R^3$, $R^4$, $R^5$, $R^6$ and $R^7$ have the abovementioned meanings.

Depending on the position of the substituent G, the compounds of the formula (I-8) can exist in the two isomeric formulae (I-8-A) and (I-8-B),

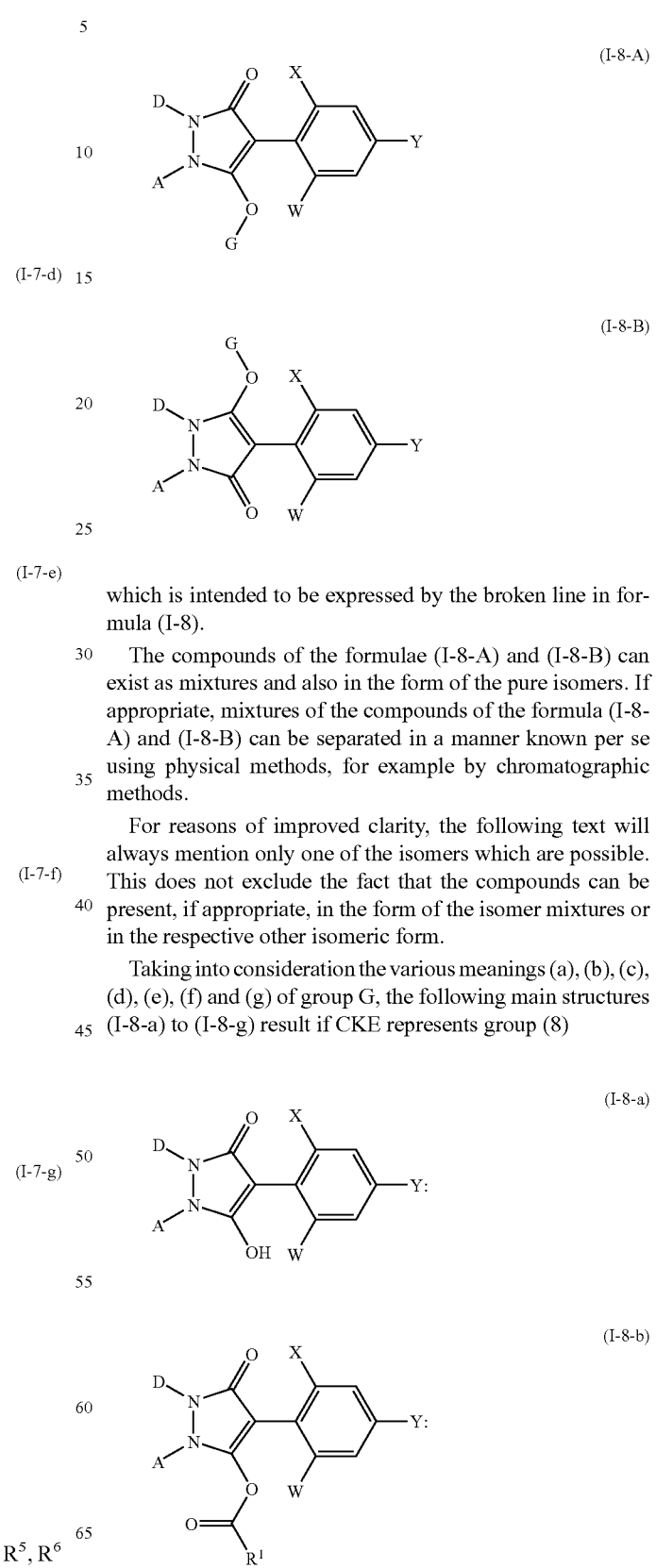

which is intended to be expressed by the broken line in formula (I-8).

The compounds of the formulae (I-8-A) and (I-8-B) can exist as mixtures and also in the form of the pure isomers. If appropriate, mixtures of the compounds of the formula (I-8-A) and (I-8-B) can be separated in a manner known per se using physical methods, for example by chromatographic methods.

For reasons of improved clarity, the following text will always mention only one of the isomers which are possible. This does not exclude the fact that the compounds can be present, if appropriate, in the form of the isomer mixtures or in the respective other isomeric form.

Taking into consideration the various meanings (a), (b), (c), (d), (e), (f) and (g) of group G, the following main structures (I-8-a) to (I-8-g) result if CKE represents group (8)

-continued (I-8-c)
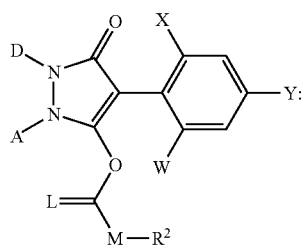

(I-8-d)
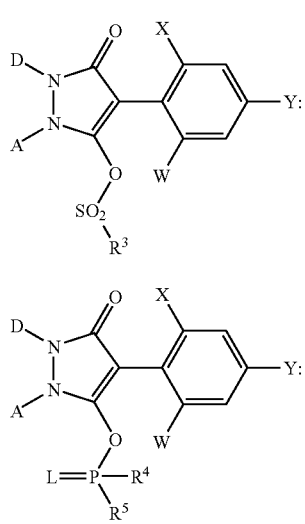

(I-8-e)

(I-8-f)
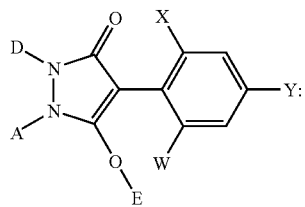

(I-8-g)
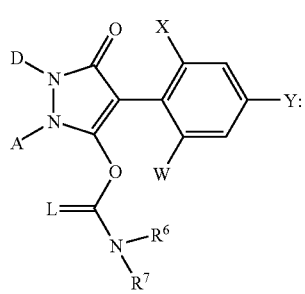

in which

A, D, E, L, M, W, X, Y, $R^1$, $R^2$, $R^3$, $R^4$, $R^5$, $R^6$ and $R^7$ have the abovementioned meanings.

Furthermore, it has been found that the new compounds of the formula (I) are obtained by one of the processes described below:

(A) Substituted 3-phenylpyrrolidine-2,4-diones or their enols of the formula (I-1-a)

(I-1-a)
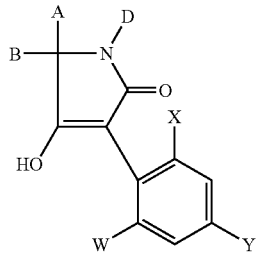

in which
A, B, D, W, X and Y have the abovementioned meanings
are obtained when
N-acylamino acid esters of the formula (II)

(II)
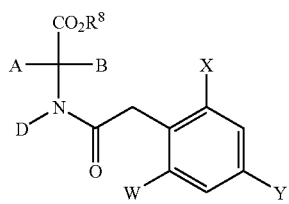

in which
A, B, D, W, X and Y have the abovementioned meanings
and
$R^8$ represents alkyl (preferably $C_1$-$C_6$-alkyl)
are subjected to an intramolecular condensation reaction in the presence of a diluent and in the presence of a base.

(B) Furthermore, it has been found that substituted 3-phenyl-4-hydroxy-$\Delta^3$-dihydrofuranone derivatives of the formula (I-2-a)

(I-2-a)
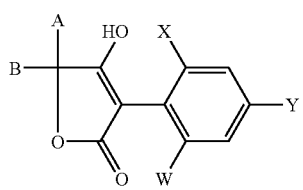

in which
A, B, W, X and Y have the abovementioned meanings
are obtained when
carboxylic esters of the formula (II)

(III)
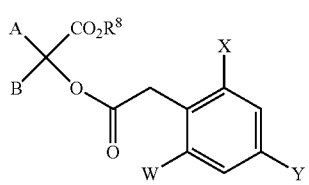

in which
A, B, W, X, Y and $R^8$ have the abovementioned meanings are subjected to an intramolecular condensation reaction in the presence of a diluent and in the presence of a base.

(C) Furthermore, it has been found that substituted 3-phenyl-4-hydroxy-Δ³-dihydrothiophenone derivatives of the formula (I-3-a)

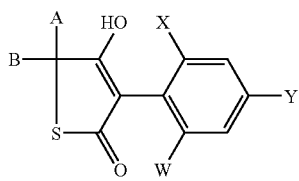
(I-3-a)

in which
A, B, W, X and Y have the abovementioned meanings are obtained when
β-ketocarboxylic esters of the formula (IV)

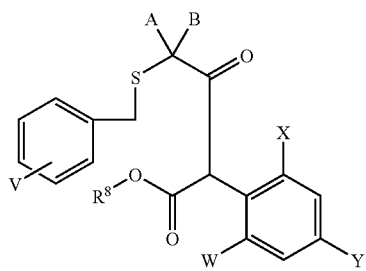
(IV)

in which
A, B, W, X, Y and R⁸ have the abovementioned meanings and
V represents hydrogen, halogen, alkyl (preferably $C_1$-$C_6$-alkyl) or alkoxy (preferably $C_1$-$C_8$-alkoxy)
are subjected to intramolecular cyclization, if appropriate in the presence of a diluent and in the presence of an acid.

(D) Furthermore, it has been found that the new substituted 3-phenyl-pyrone derivatives of the formula (I-4-a)

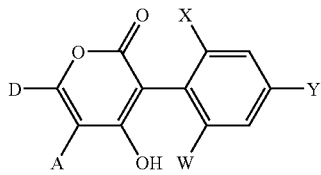
(I-4-a)

in which
A, D, W, X and Y have the abovementioned meanings are obtained when
carbonyl compounds of the formula (V)

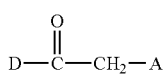
(V)

in which
A and D have the abovementioned meanings
or their silyl enol ethers of the formula (Va)

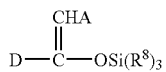
(Va)

in which
A, D and R⁸ have the abovementioned meanings
are reacted with ketene acid halides of the formula (VI)

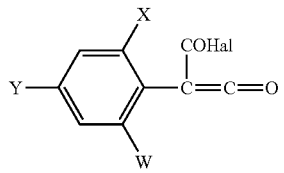
(VI)

in which
W, X and Y have the abovementioned meanings and
Hal represents halogen (preferably chlorine or bromine),
if appropriate in the presence of a diluent and if appropriate in the presence of an acid acceptor.

Furthermore, it has been found
(E) that the new substituted phenyl-1,3-thiazine derivatives of the formula (I-5-a)

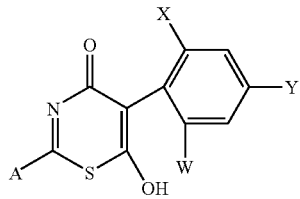
(I-5-a)

in which
A, W, X and Y have the abovementioned meanings
are obtained when thioamides of the formula (VII)

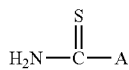
(VII)

in which
A has the abovementioned meaning
are reacted with ketene acid halides of the formula (VI)

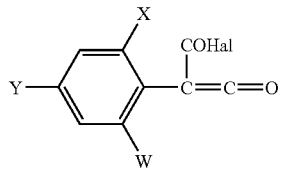
(VI)

in which
Hal, W, X and Y have the abovementioned meanings,
if appropriate in the presence of a diluent and if appropriate in the presence of an acid acceptor.

Furthermore, it has been found (F) that compounds of the formula (I-6-a)

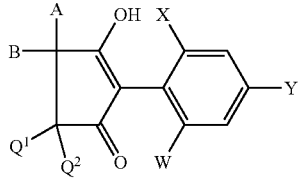
(I-6-a)

in which

A, B, $Q^1$, $Q^2$, W, X and Y have the abovementioned meanings are obtained when ketocarboxylic esters of the formula (VIII)

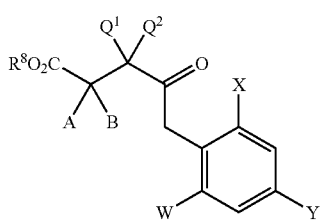
(VIII)

in which

A, B, $Q^1$, $Q^2$, W, X and Y have the abovementioned meanings and $R^8$ represents alkyl (in particular $C_1$-$C_8$-alkyl)

are subjected to an intramolecular cyclization reaction, if appropriate in the presence of a diluent and in the presence of a base.

Furthermore, it has been found (G) that compounds of the formula (I-7-a)

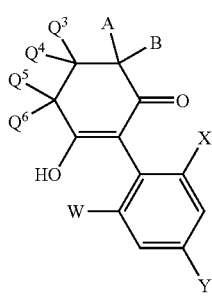
(I-7-a)

in which

A, B, $Q^3$, $Q^4$, $Q^5$, $Q^6$, W, X and Y have the abovementioned meanings are obtained when 6-aryl-5-ketohexanoic esters of the formula (IX)

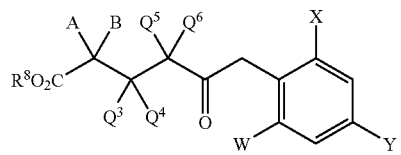
(IX)

in which

A, B, $Q^3$, $Q^4$, $Q^5$, $Q^6$, W, X and Y have the abovementioned meanings and $R^8$ represents alkyl (preferably $C_1$-$C_6$-alkyl)

are subjected to an intramolecular condensation reaction in the presence of a diluent and in the presence of a base.

(H) Furthermore, it has been found that the compounds of the formula (I-8-a)

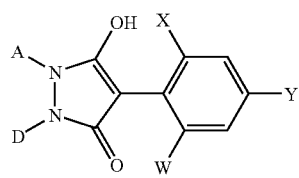
(I-8-a)

in which

A, D, W, X and Y have the abovementioned meanings are obtained when compounds of the formula (X)

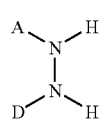
(X)

in which

A and D have the abovementioned meanings

α) are reacted with compounds of the formula (VI)

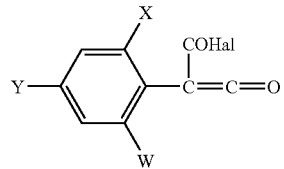
(VI)

in which

Hal, X, Y and W have the abovementioned meanings, if appropriate in the presence of a diluent and if appropriate in the presence of an acid acceptor, or β) are reacted with compounds of the formula (XI)

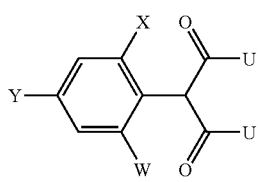

(XI)

in which

W, X and Y have the abovementioned meanings, and U represents $NH_2$ or $O-R^8$, where $R^8$ has the abovementioned meaning, if appropriate in the presence of a diluent and if appropriate in the presence of a base, or γ) are reacted with compounds of the formula (XII)

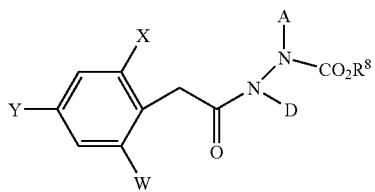

(XII)

in which

A, D, W, X, Y and $R^8$ have the abovementioned meanings, if appropriate in the presence of a diluent and if appropriate in the presence of a base.

Furthermore, it has been found (I) that the compounds of the formulae (I-1-b) to (I-8-b) shown above in which A, B, D, $Q^1$, $Q^2$, $Q^3$, $Q^4$, $Q^5$, $Q^6$, $R^1$, W, X, and Y have the abovementioned meanings are obtained when compounds of the formulae (I-1-a) to (I-8-a) shown above in which A, B, D, $Q^1$, $Q^2$, $Q^3$, $Q^4$, $Q^5$, $Q^6$, W, X and Y have the abovementioned meanings are reacted in each case (α) with acid halides of the formula (XIII)

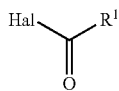

(XIII)

in which $R^1$ has the abovementioned meaning and

Hal represents halogen (in particular chlorine or bromine), or (β) with carboxylic anhydrides of the formula (XIV)

 (XIV)

in which $R^1$ has the abovementioned meaning, if appropriate in the presence of a diluent and if appropriate in the presence of an acid-binding agent;

(J) that the compounds of the formulae (I-1-c) to (I-8-c) shown above in which A, B, D, $Q^1$, $Q^2$, $Q^3$, $Q^4$, $Q^5$, $Q^6$, $R^2$, M, W, X and Y have the abovementioned meanings and L represents oxygen are obtained when compounds of the formulae (I-1-a) to (I-8-a) shown above in which A, B, D, $Q^1$, $Q^2$, $Q^3$, $Q^4$, $Q^5$, $Q^6$, W, X and Y have the abovementioned meanings are reacted in each case with chloroformic esters or chloroformic thioesters of the formula (XV)

 (XV)

in which $R^2$ and M have the abovementioned meanings, if appropriate in the presence of a diluent and if appropriate in the presence of an acid-binding agent;

(K) that compounds of the formulae (I-1-c) to (I-8-c) shown above in which A, B, D, $Q^1$, $Q^2$, $Q^3$, $Q^4$, $Q^5$, $Q^6$, $R^2$, M, W, X and Y have the abovementioned meanings and L represents sulphur are obtained when compounds of the formulae (I-1-a) to (I-8-a) shown above in which A, B, D, $Q^1$, $Q^2$, $Q^3$, $Q^4$, $Q^5$, $Q^6$, W, X and Y have the abovementioned meanings are reacted in each case with chloromonothioformic esters or chlorodithioformic esters of the formula (XVI)

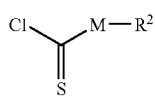

(XVI)

in which

M and $R^2$ have the abovementioned meanings, if appropriate in the presence of a diluent and if appropriate in the presence of an acid-binding agent, and (L) that compounds of the formulae (I-1-d) to (I-8-d) shown above in which A, B, D, $Q^1$, $Q^2$, $Q^3$, $Q^4$, $Q^5$, $Q^6$, $R^3$, W, X and Y have the abovementioned meanings are obtained when compounds of the formulae (I-1-a) to (I-8-a) shown above in which A, B, D, $Q^1$, $Q^2$, $Q^3$, $Q^4$, $Q^5$, $Q^6$, W, X and Y have the abovementioned meanings are reacted in each case with sulphonyl chlorides of the formula (XVII)

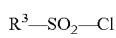 (XVII)

in which $R^3$ has the abovementioned meaning, if appropriate in the presence of a diluent and if appropriate in the presence of an acid-binding agent, (M) that compounds of the formulae (I-1-e) to (I-8-e) shown above in which A, B, D, L, $Q^1$, $Q^2$, $Q^3$, $Q^4$, $Q^5$, $Q^6$ $R^4$, $R^5$, W, X and Y have the abovementioned meanings are obtained when compounds of the formulae (I-1-a) to (I-8-a) shown above in which A, B, D, $Q^1$, $Q^2$, $Q^3$, $Q^4$, $Q^5$, $Q^6$, W, X and Y have the abovementioned meanings are reacted in each case with phosphorus compounds of the formula (XVII)

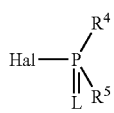

(XVIII)

in which

L, $R^4$ and $R^5$ have the abovementioned meanings and

Hal represents halogen (in particular chlorine or bromine), if appropriate in the presence of a diluent and if appropriate in the presence of an acid-binding agent, (N) that compounds of the formulae (I-1-f) to (I-8-f) shown above in which A, B, D, E, $Q^1, Q^2, Q^3, Q^4, Q^5, Q^6$, W, X and Y have the abovementioned meanings are obtained when compounds of the formulae (I-1-a) to (I-8-a) in which A, B, D, $Q^1, Q^2, Q^3, Q^4, Q^5, Q^6$, W, X and Y have the abovementioned meanings are in each case reacted with metal compounds or amines of the formulae (XIX) or (XX)

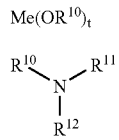     (XIX)

     (XX)

in which

Me represents a mono- or divalent metal (preferably an alkali metal or alkaline earth metal, such as lithium, sodium, potassium, magnesium or calcium), or represents an ammonium ion

t represents the number 1 or 2 and
$R^{10}, R^{11}$ and $R^{12}$ independently of one another represent hydrogen or alkyl (preferably $C_1$-$C_8$-alkyl),
if appropriate in the presence of a diluent, (O) that compounds of the formulae (I-1-g) to (I-8-g) shown above in which A, B, D, L, $Q^1, Q^2, Q^3, Q^4, Q^5, Q^6, R^6, R^7$, W, X and Y have the abovementioned meanings are obtained when compounds of the formulae (I-1-a) to (I-8-a) shown above in which A, B, D, $Q^1, Q^2, Q^3, Q^4, Q^5, Q^6$, W, X and Y have the abovementioned meanings are reacted in each case (α) with isocyanates or isothiocyanates of the formula (XXI)

$R^6$—N=C=L     (XXI)

in which
$R^6$ and L have the abovementioned meanings,
if appropriate in the presence of a diluent and if appropriate in the presence of a catalyst, or ( ) with carbamoyl chlorides or thiocarbamoyl chlorides of the formula (XXII)

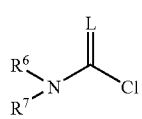     (XXII)

in which
L, $R^6$ and $R^7$ have the abovementioned meanings, if appropriate in the presence of a diluent and if appropriate in the presence of an acid-binding agent, (P) that compounds of the formulae (I-1-a) to (I-8-a) shown above in which A, B, D, $Q^1, Q^2, Q^3, Q^4, Q^5, Q^6$, W, X and Y have the abovementioned meanings are obtained when compounds of the formulae (I-1-a') to (I-8-a') in which A, B, D, $Q^1, Q^2, Q^3, Q^4, Q^5, Q^6$, X and Y have the abovementioned meanings and W' preferably represents bromine

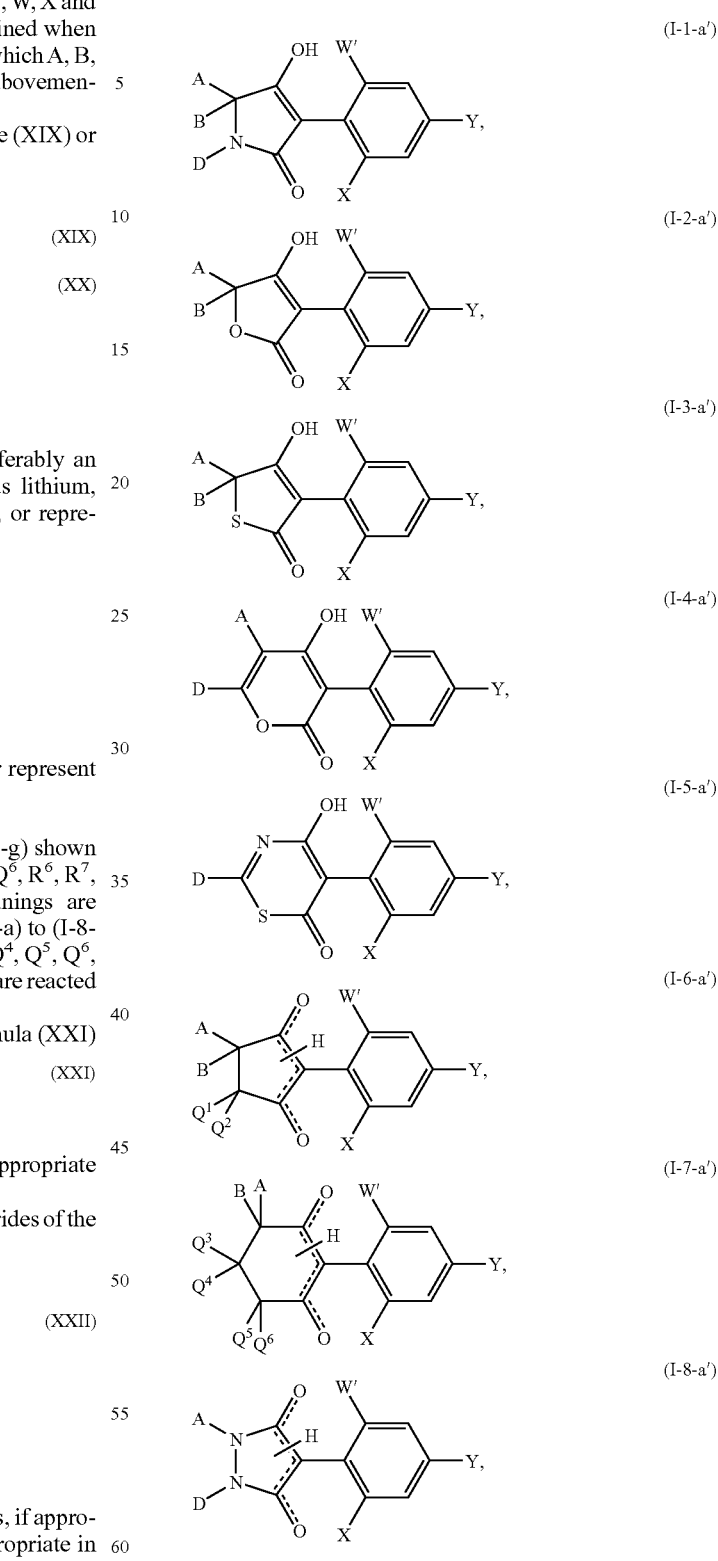

are reacted with alcohols of the formula

in which
W has the abovementioned meaning, if appropriate in the presence of a diluent, a Cu(I) salt (for example CuBr, CuI) and a strong base (for example sodium hydride, potassium tert-butoxide).

Furthermore, it has been found that the new compounds of the formula (I) have a very good activity as pesticides, preferably as insecticides, acaricides and/or herbicides.

Surprisingly, it has now also been found that certain substituted cyclic ketoenols, when used jointly with the compounds which improve crop plant tolerance (safeners/antidotes) described hereinbelow, are extremely effective in preventing damage of the crop plants and can be used especially advantageously as combination products with a broad range of activity for the selective control of undesired plants in crops of useful plants, such as, for example, in cereals, but also in maize, soybeans and rice.

The invention also relates to selectively herbicidal compositions with an effective content of an active compound combination comprising, as components, (a') at least one substituted cyclic ketoenol of the formula (I) in which CKE, W, X and Y have the abovementioned meanings and (b') at least one compound which improves crop plant tolerance and which is selected from the following group of compounds:

4-dichloroacetyl-1-oxa-4-aza-spiro[4.5]-decane (AD-67, MON-4660), 1-dichloro-acetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl—cf. also related compounds in EP-A-86750, EP-A-94349, EP-A-191736, EP-A-492366), 3-(2-chloro-benzyl)-1-(1-methyl-1-phenyl-ethyl)-urea (cumyluron), α-(cyanomethoximino)-phenylacetonitrile (cyometrinil), 2,4-dichloro-phenoxyacetic acid (2,4-D), 4-(2,4-dichloro-phenoxy)-butyric acid (2,4-DB), 1-(1-methyl-1-phenyl-ethyl)-3-(4-methyl-phenyl)-urea (daimuron, dymron), 3,6-dichloro-2-methoxy-benzoic acid (dicamba), S-1-methyl-1-phenyl-ethyl piperidine-1-thiocarboxylate (dimepiperate), 2,2-dichloro-N-(2-oxo-2-(2-propenylamio)-ethyl)-N-(2-propenyl)-acetamide (DKA-24), 2,2-dichloro-N,N-di-2-propenyl acetamide (dichlormid), 4,6-dichloro-2-phenyl-pyrimidine (fenclorim), ethyl 1-(2,4-dichloro-phenyl)-5-trichloro-methyl-1H-1,2,4-triazole-3-carboxylate (fenchlorazole-ethyl—cf. also related compounds in EP-A-174562 and EP-A-346620), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazole-carboxylate (isoxadifen-ethyl—cf. also related compounds in WO-A-95/07897), 1-(ethoxycarbonyl)-ethyl-3,6-dichloro-2-methoxybenzoate (lactidichlor), (4-chloro-o-tolyloxy)-acetic acid (MCPA), 2-(4-chloro-o-tolyloxy)-propionic acid (mecoprop), diethyl 1-(2,4-dichloro-phenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-aza-spiro[4.5]decane 4-carbodithioate (MG-838), 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chloro-phenoxy)-butyric acid, diphenylmethoxyacetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl)-5-phenyl-1H-pyrazole-3-carboxylate (cf. also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinolin-8-oxy-acetate, ethyl 5-chloro-quinolin-8-oxy-acetate, allyl 5-chloro-quinoxalin-8-oxy-acetate, 2-oxo-prop-1-yl 5-chloro-quinolin-8-oxy-acetate, diethyl 5-chloro-quinolin-8-oxy-malonate, diallyl 5-chloro-quinoxalin-8-oxy-malonate, diethyl 5-chloro-quinolin-8-oxy-malonate (cf. also related compounds in EP-A-582198), 4-carboxy-chroman-4-yl-acetic acid (AC-304415, cf. EP-A-613618), 4-chloro-phenoxy-acetic acid, 3,3'-dimethyl-4-methoxy-benzophenone, 1-bromo4-chloromethylsulphonyl-benzene, 1-[4-(N-2-methoxybenzoylsulphamoyl)-phenyl]-3-methyl-urea (alias N-(2-methoxy-benzoyl)-4-[(methylamino-carbonyl)-amino]-benzenesulphonamide), 1-[4-(N-2-methoxybenzoylsulphamoyl)-phenyl]-3,3-dimethyl-urea, 1-[4-(N4,5-dimethylbenzoylsulphamoyl)-phenyl]-3-methyl-urea, 1-[4-(N-naphthylsulphamoyl)-phenyl]-3,3-dimethyl-urea, N-(2-methoxy-5-methyl-benzoyl)-4-(cyclopropylaminocarbonyl)-benzenesulphonamide, and/or one of the following compounds (defined by general formulae)

of the general formula (IIa)

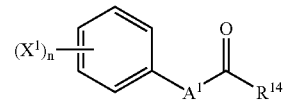

or of the general formula (IIb)

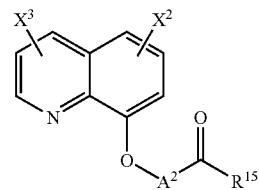

or of the formula (IIc)

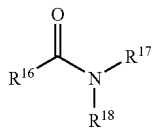

where n represents a number of between 0 and 5,

A¹ represents one of the divalent heterocyclic groups outlined hereinbelow

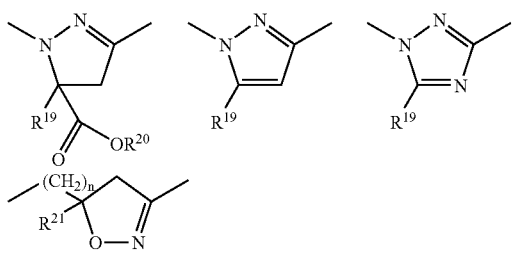

n represents a number of between 0 and 5,

A² represents alkanediyl having 1 or 2 carbon atoms which is optionally substituted by $C_1$-$C_4$-alkyl and/or $C_1$-$C_4$-alkoxycarbonyl, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{16}$ represents $C_1$-$C_4$-alkyl which is optionally substituted in each case by fluorine, chlorine and/or bromine, $R^{17}$ represents hydrogen, or represents $C_1$-$C_6$-alkyl, $C_2$-$C_6$-alkenyl or $C_2$-$C_6$-alkinyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, $R^{18}$ represents hydrogen, or represents $C_1$-$C_6$-alkyl, $C_2$-$C_6$-alkenyl or $C_2$-$C_6$-alkinyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, or together with $R^{17}$ represents $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are bonded, form a 5- or 6-membered carbocycle, $R^{19}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $R^{20}$ represents hydrogen, or represents $C_1$-$C_6$-alkyl, $C_3$-$C_6$-cycloalkyl or tri($C_1$-$C_4$-alkyl)silyl, in each case optionally substituted by hydroxyl, cyano, halogen or $C_1$-$C_4$-alkoxy, $R^{21}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $X^1$ represents nitro, cyano, halogen, $C_1$-$C_4$-alkyl, $C_1$-$C_4$-halogenoalkyl, $C_1$-$C_4$-alkoxy or $C_1$-$C_4$-halogenoalkoxy, $X^2$ represents hydrogen, cyano, nitro, $C_1$-$C_4$-alkyl, $C_1$-$C_4$-halogenoalkyl, $C_1$-$C_4$-alkoxy or $C_1$-$C_4$-halogenoalkoxy, $X^3$ represents hydrogen, cyano, nitro, $C_1$-$C_4$-alkyl, $C_1$-$C_4$-halogenoalkyl, $C_1$-$C_4$-alkoxy or $C_1$-$C_4$-halogenoalkoxy, and/or the following compounds (defined by general formulae)

of the general formula (IId)

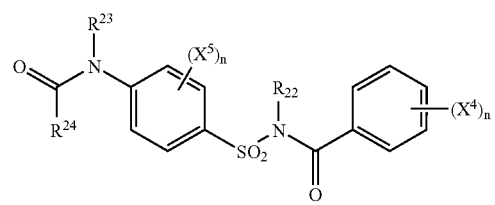

or of the general formula (IIe)

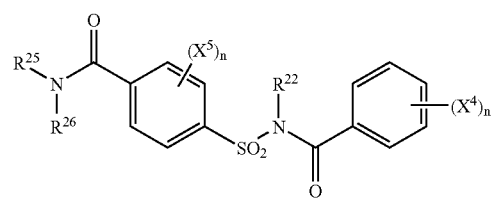

where n represents a number of between 0 and 5, $R^{22}$ represents hydrogen or $C_1$-$C_4$-alkyl, $R^{23}$ represents hydrogen or $C_1$-$C_4$-alkyl, $R^{24}$ represents hydrogen, or represents $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, each of which is optionally substituted by cyano, halogen or $C_1$-$C_4$-alkoxy, or represents $C_3$-$C_6$-cycloalkyl, $C_3$-$C_6$-cycloalkyloxy, $C_3$-$C_6$-cycloalkylthio or $C_3$-$C_6$-cycloalkylamino, each of which is optionally substituted by cyano, halogen or $C_1$-$C_4$-alkyl, $R^{25}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkinyl, each of which is optionally substituted by cyano or halogen, or represents $C_3$-$C_6$-cycloalkyl which is optionally substituted by cyano, halogen or $C_1$-$C_4$-alkyl, $R^{26}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkinyl, each of which is optionally substituted by cyano or halogen, or represents $C_3$-$C_6$-cycloalkyl which is optionally substituted by cyano, halogen or $C_1$-$C_4$-alkyl, or represents phenyl which is optionally substituted by nitro, cyano, halogen, $C_1$-$C_4$-alkyl, $C_1$-$C_4$-halogenoalkyl, $C_1$-$C_4$-alkoxy or $C_1$-$C_4$-halogenoalkoxy, or together with $R^{25}$ represents $C_2$-$C_6$-alkanediyl or $C_2$-$C_5$-oxaalkanediyl, each of which is optionally substituted by $C_1$-$C_4$-alkyl, $X^4$ represents nitro, cyano, carboxyl, carbamoyl, formyl, sulphamoyl, hydroxyl, amino, halogen, $C_1$-$C_4$-alkyl, $C_1$-$C_4$-halogenoalkyl, $C_1$-$C_4$-alkoxy or $C_1$-$C_4$-halogenoalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-halogenoalkyl, $C_1$-$C_4$-alkoxy or $C_1$-$C_4$-halogenoalkoxy.

Formula (I) provides a general definition of the compounds according to the invention. Preferred substituents or ranges of the radicals given in the formulae mentioned hereinabove and hereinbelow are illustrated in the following text:

W preferably represents $C_1$-$C_6$-alkoxy, $C_1$-$C_6$-halogenoaloxy, $C_1$-$C_4$-alkoxy-$C_2$-$C_4$-alkyloxy, $C_1$-$C_4$-alkoxy-bis- $C_2$-$C_4$-alkyloxy, or represents $C_3$-$C_6$-cycloalkyl-$C_1$-$C_3$-alkanediyloxy which is optionally monosubstituted to trisubstituted by fluorine, chlorine, $C_1$-$C_3$-alkyl or $C_1$-$C_3$-alkoxy and in which one methylene group of the ring can optionally be interrupted by oxygen or sulphur, X preferably represents $C_1$-$C_6$-alkyl, Y preferably represents chlorine, bromine or iodine, CKE preferably represents one of the groups

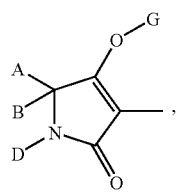

(1)

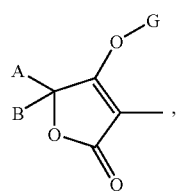

(2)

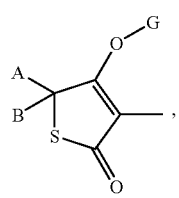

(3)

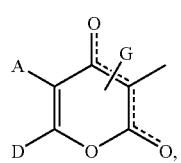

(4)

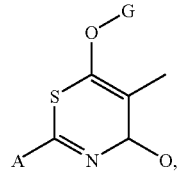

(5)

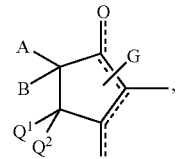

(6)

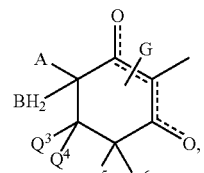

(7)

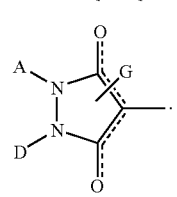

(8)

A preferably represents hydrogen, or represents $C_1$-$C_{12}$-alkyl, C3-C8-alkenyl, $C_1$-$C_{10}$-alkoxy-$C_1$-$C_8$-alkyl or $C_1$-$C_{10}$-alkylthio-$C_1$-$C_6$-alkyl, each of which is optionally substituted by halogen, or represents $C_3$-$C_8$-cycloalkyl in which one or two ring members which are not directly adjacent are optionally replaced by oxygen and/or sulphur and which is optionally substituted by halogen, $C_1$-$C_6$-alkyl or $C_1$-$C_6$-alkoxy, or represents phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, each of which is optionally substituted by halogen, $C_1$-$C_6$-alkyl, $C_1$-$C_6$-halogenoalkyl, $C_1$-$C_6$-alkoxy, $C_1$-$C_6$-halogenoalkoxy, cyano or nitro, B preferably represents hydrogen, $C_1$-$C_{12}$-alkyl or $C_1$-$C_8$-alkoxy-$C_1$-$C_6$-alkyl, or A, B and the carbon atom to which they are bonded preferably represent saturated $C_3$-$C_{10}$-cycloalkyl or unsaturated $C_5$-$C_{10}$-cycloalkyl in which one ring member is optionally replaced by oxygen or sulphur and which is optionally monosubstituted or disubstituted by $C_1$-$C_8$-alkyl, $C_3$-$C_{10}$-cycloalkyl, $C_1$-$C_8$-halogenoalkyl, $C_1$-$C_8$-alkoxy, $C_1$-$C_8$-alkylthio, halogen or phenyl, or A, B and the carbon atom to which they are bonded preferably represent $C_3$-$C_6$-cycloalkyl which is substituted by an alkylenediyl group which is optionally substituted by $C_1$-$C_4$-alkyl and which optionally contains one or two oxygen and/or sulphur atoms which are not directly adjacent, or by an alkylenedioxy or by an alkylenedithio group, this group together with the carbon atom to which it is bonded forming a further five- to eight-membered ring, or A, B and the carbon atom to which they are bonded preferably represent $C_3$-$C_8$-cycloalkyl or $C_5$-$C_8$-cycloalkenyl in which two substituents together with the carbon atoms to which they are bonded represent $C_2$-$C_6$-alkanediyl, $C_2$-$C_6$-alkenediyl or $C_4$-$C_6$-alkanedienediyl, in which one methylene group is optionally replaced by oxygen or sulphur and each of which is optionally substituted by $C_1$-$C_6$-alkyl, $C_1$-$C_6$-alkoxy or halogen, D preferably represents hydrogen, or represents $C_1$-$C_{12}$-alkyl, $C_3$-$C_8$-alkenyl, $C_3$-$C_8$-alkinyl, $C_1$-$C_{10}$-alkoxy-$C_2$-

$C_8$-alkyl, each of which is optionally substituted by halogen, or represents $C_3$-$C_8$-cycloalkyl in which a ring member is optionally replaced by oxygen or sulphur and which is optionally substituted by halogen, $C_1$-$C_4$-alkyl, $C_1$-$C_4$-alkoxy or $C_1$-$C_4$-halogenoalkyl, or represents phenyl, hetaryl having 5 or 6 ring atoms, (for example furanyl, imidazolyl, pyridyl, thiazolyl, pyrazolyl, pyrinidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl), each of which is optionally substituted by halogen, $C_1$-$C_6$-alkyl, $C_1$-$C_6$-halogenoalkyl, $C_1$-$C_6$-alkoxy, $C_1$-$C_6$-halogenoalkoxy, cyano or nitro, or A and D together preferably represent in each case optionally substituted $C_3$-$C_6$-alkanediyl or $C_3$-$C_6$-alkenediyl, in which one methylene group is optionally replaced by a carbonyl group, oxygen or sulphur, and where suitable substituents in each case are:
halogen, hydroxyl, mercapto, or $C_1$-$C_{10}$-alkyl, $C_1$-$C_6$-alkoxy, $C_1$-$C_6$-alkylthio, $C_3$-$C_7$-cycloalkyl, phenyl or benzyloxy, each of which is optionally substituted by halogen; or a further $C_3$-$C_6$-alkanediyl group, $C_3$-$C_6$-alkenediyl group or a butadienyl group which is optionally substituted by $C_1$-$C_6$-alkyl or in which two adjacent substituents together with the carbon atoms to which they are bonded optionally form a further saturated or unsaturated cycle having 5 or 6 ring atoms (in the case of the compound of the formula (I-1), A and D will now jointly with the atoms to which they are bonded represent for example the groups AD-1 to AD-10, which are detailed further below) which can contain oxygen or sulphur, or which optionally contains one of the following groups

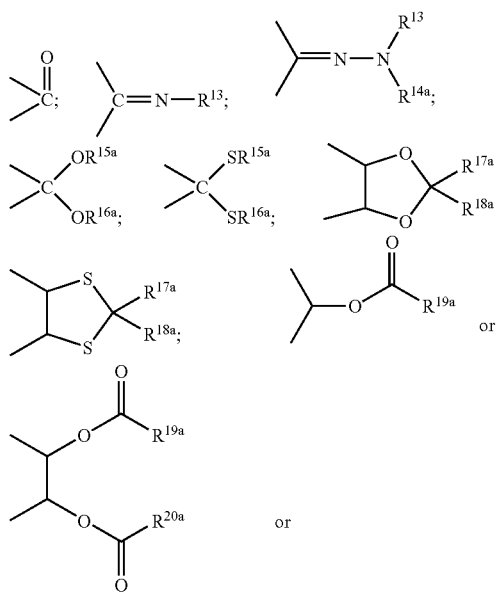

A and $Q^1$ jointly preferably represent $C_3$-$C_6$-alkanediyl or $C_4$-$C_6$-alkenediyl, each of which is optionally monosubstituted or disubstituted by identical or different substituents from the series consisting of halogen, hydroxyl, or $C_1$-$C_{10}$-alkyl, $C_1$-$C_6$-alkoxy, $C_1$-$C_6$-alkylthio, $C_3$-$C_7$-cycloalkyl, each of which is optionally monosubstitued to trisubstituted by identical or different halogen substituents, or benzyloxy or phenyl, each of which is optionally monosubstituted to trisubstituted by identical or different substituents from the series consisting of halogen, $C_1$-$C_6$-alkyl or $C_1$-$C_6$-alkoxy, this $C_3$-$C_6$-alkanediyl or $C_4$-$C_6$-alkenediyl additionally optionally containing one of the following groups

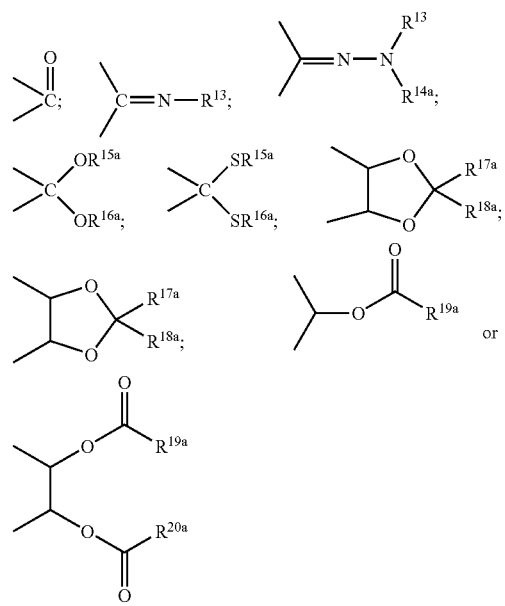

or being bridged via a $C_1$-$C_2$-alkanediyl group or by an oxygen atom, or $Q^1$ preferably represents hydrogen or $C_1$-$C_4$-alkyl, $Q^2$, $Q^4$, $Q^5$ and $Q^6$ independently of one another preferably represent hydrogen or $C_1$-$C_4$-alkyl, $Q^3$ preferably represents hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, $C_3$-$C_8$-cycloalkyl which is optionally substituted by $C_1$-$C_4$-alkyl or $C_1$-$C_4$-alkoxy and in which one methylene group is optionally replaced by oxygen or sulphur, or phenyl which is optionally substituted by halogen, $C_1$-$C_4$-alkyl, $C_1$-$C_4$-alkoxy, $C_1$-$C_2$-halogenoalkyl, $C_1$-$C_2$-halogenoalkoxy, cyano or nitro, or $Q^3$ and $Q^4$ together with the carbon atom to which they are bonded preferably represent a $C_3$-$C_7$ ring which is optionally substituted by $C_1$-$C_4$-alkyl, $C_1$-$C_4$-alkoxy or $C_1$-$C_2$-halogenoalkyl and in which one ring member is optionally replaced by oxygen or sulphur, G preferably represents hydrogen (a) or one of the groups

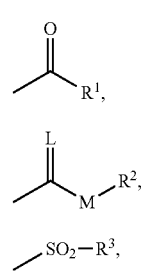

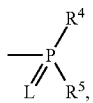 (e)

E or (f)

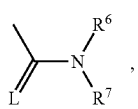 (g)

in particular (a), (b), (c) or (g),
in which
E represents a metal ion equivalent or an ammonium ion,
L represents oxygen or sulphur and
M represents oxygen or sulphur.

$R^1$ preferably represents $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl, each of which is optionally substituted by halogen, or represents $C_3$-$C_8$-cycloalkyl in which one or more (preferably not more than two) ring members which are not directly adjacent are optionally replaced by oxygen and/or sulphur and which is optionally substituted by halogen, $C_1$-$C_6$-alkyl or $C_1$-$C_6$-alkoxy, or phenyl which is optionally substituted by halogen, cyano, nitro, $C_1$-$C_6$-alkyl, $C_1$-$C_6$-alkoxy, $C_1$-$C_6$-halogenoalkyl, $C_1$-$C_6$-halogenoalkoxy, $C_1$-$C_6$-alkylthio or $C_1$-$C_6$-alkylsulphonyl, or phenyl-$C_1$-$C_6$-alkyl which is optionally substituted by halogen, nitro, cyano, $C_1$-$C_6$-alkyl, $C_1$-$C_6$-alkoxy, $C_1$-$C_6$-halogenoalkyl or $C_1$-$C_6$-halogenoalkoxy, or 5- or 6-membered hetaryl (for example pyrazolyl, thiazolyl, pyridyl, pyrimidyl, furanyl or thienyl) which is optionally substituted by halogen or $C_1$-$C_6$-alkyl, or phenoxy-$C_1$-$C_6$-alkyl which is optionally substituted by halogen or $C_1$-$C_6$-alkyl, or 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl) which is optionally substituted by halogen, amino or $C_1$-$C_6$-alkyl.

$R^2$ preferably represents $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, each of which is optionally substituted by halogen, or $C_3$-$C_8$-cycloalkyl which is optionally substituted by halogen, $C_1$-$C_6$-alkyl or $C_1$-$C_6$-alkoxy, or phenyl or benzyl, each of which is optionally substituted by halogen, cyano, nitro, $C_1$-$C_6$-alkyl, $C_1$-$C_6$-alkoxy, $C_1$-$C_6$-halogenoalkyl or $C_1$-$C_6$-halogenoalkoxy, $R^3$ preferably represents $C_1$-$C_8$-alkyl which is optionally substituted by halogen, or phenyl or benzyl, each of which is optionally substituted by halogen, $C_1$-$C_6$-alkyl, $C_1$-$C_6$-alkoxy, $C_1$-$C_4$-halogenoalkyl, $C_1$-$C_4$-halogenoalkoxy, cyano or nitro, $R^4$ and $R^5$ preferably independently of one another represent $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio or $C_3$-$C_7$-cycloalkylthio, each of which is optionally substituted by halogen, or phenyl, phenoxy or phenylthio, each of which is optionally substituted by halogen, nitro, cyano, $C_1$-$C_4$-alkoxy, $C_1$-$C_4$-halogenoalkoxy, $C_1$-$C_4$-alkylthio, $C_1$-$C_4$-halogenoalkylthio, $C_1$-$C_4$-alkyl or $C_1$-$C_4$-halogenoalkyl, $R^6$ and $R^7$ independently of one another preferably represent hydrogen, or $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_1$-$C_8$-alkyl, each of which is optionally substituted by halogen, or phenyl which is optionally substituted by halogen, $C_1$-$C_8$-halogenoalkyl, $C_1$-$C_8$-alkyl or $C_1$-$C_8$-alkoxy, or benzyl which is optionally substituted by halogen, $C_1$-$C_8$-alkyl, $C_1$-$C_8$-halogenoalkyl or $C_1$-$C_8$-alkoxy, or together represent a $C_3$-$C_6$-alkylene radical which is optionally substituted by $C_1$-$C_4$-alkyl and in which one carbon atom is optionally replaced by oxygen or sulphur, $R^{13}$ preferably represents hydrogen, $C_1$-$C_8$-alkyl or $C_1$-$C_8$-alkoxy, each of which is optionally substituted by halogen, $C_3$-$C_8$-cycloalkyl in which one methylene group is optionally replaced by oxygen or sulphur and which is optionally substituted by halogen, $C_1$-$C_4$-alkyl or $C_1$-$C_4$-alkoxy, or phenyl, phenyl-$C_1$-$C_4$-alkyl or phenyl-$C_1$-$C_4$-alkoxy, each of which is optionally substituted by halogen, $C_1$-$C_6$-alkyl, $C_1$-$C_6$-alkoxy, $C_1$-$C_4$-halogenoalkyl, $C_1$-$C_4$-halogenoalkoxy, nitro or cyano, $R^{14a}$ preferably represents hydrogen or $C_1$-$C_8$-alkyl, or $R^{13}$ and $R^{14a}$ together preferably represent $C_4$-$C_6$-alkanediyl, $R^{15a}$ and $R^{16a}$ are identical or different and preferably represent $C_1$-$C_6$-alkyl, or $R^{15a}$ and $R^{16a}$ together preferably represent a $C_2$-$C_4$-alkanediyl radical which is optionally substituted by $C_1$-$C_6$-alkyl, $C_1$-$C_6$-halogenoalkyl or by phenyl which is optionally substituted by halogen, $C_1$-$C_6$-alkyl, $C_1$-$C_4$-halogenoalkyl, $C_1$-$C_6$-alkoxy, $C_1$-$C_4$-halogenoalkoxy, nitro or cyano, $R^{17a}$ and $R^{18a}$ independently of one another preferably represent hydrogen, $C_1$-$C_8$-alkyl which is optionally substituted by halogen, or phenyl which is optionally substituted by halogen, $C_1$-$C_6$-alkyl, $C_1$-$C_6$-alkoxy, $C_1$-$C_4$-halogenoalkyl, $C_1$-$C_4$-halogenalkoxy, nitro or cyano, or $R^{17a}$ and $R^{18a}$ together with the carbon atom to which they are bonded preferably represent a carbonyl group or $C_5$-$C_7$-cycloalkyl in which one methylene group is optionally replaced by oxygen or sulphur and which is optionally substituted by halogen, $C_1$-$C_4$-alkyl or $C_1$-$C_4$-alkoxy.

$R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the definitions of radicals which have been mentioned as being preferred, halogen represents fluorine, chlorine, bromine and iodine, in particular fluorine, chlorine and bromine.

W especially preferably represents $C_1$-$C_4$-alkoxy, $C_1$-$C_4$-halogenoalkoxy, $C_1$-$C_3$-alkoxy-$C_2$-$C_3$-alkyloxy, $C_1$-$C_2$-alkoxy-bis- $C_2$-$C_3$-alkyloxy or $C_3$-$C_6$-cycloalkyl-$C_1$-$C_2$-alkanediyloxy in which one methylene group of the ring can optionally be interrupted by oxygen, X especially preferably represents $C_1$-$C_3$-alkyl, Y especially preferably represents chlorine or bromine, CKE especially preferably represents one of the groups (1) 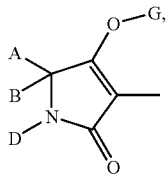

(2) 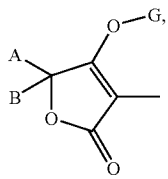

(3) 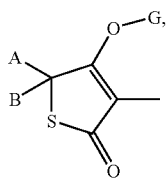

(4) 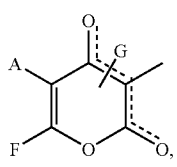

(5) 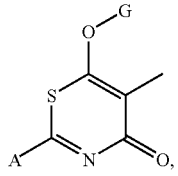

(6) 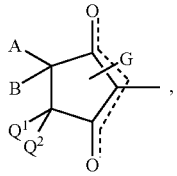

(7) 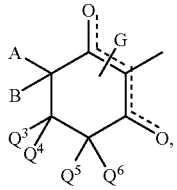

(8) 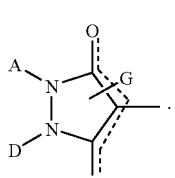

A especially preferably represents hydrogen, or represents $C_1$-$C_6$-alkyl, $C_1$-$C_4$-alkoxy-$C_1$-$C_2$-alkyl, each of which is optionally monosubstituted to trisubstituted by fluorine or chlorine, or represents $C_3$-$C_6$-cycloalkyl which is optionally monosubstituted or disubstituted by $C_1$-$C_2$-alkyl or $C_1$-$C_2$-alkoxy, or (but not in the case of the compounds of formulae (I-3), (I-4), (I-6) and (I-7)) represents phenyl or benzyl, each of which is optionally monosubstituted or disubstituted by fluorine, chlorine, bromine, $C_1$-$C_4$-alkyl, $C_1$-$C_2$-halogenoalkyl, $C_1$-$C_4$-alkoxy, $C_1$-$C_2$-halogenoalkoxy, cyano or nitro, B especially preferably represents hydrogen, $C_1$-$C_4$-alkyl or $C_1$-$C_2$-alkoxy-$C_1$-$C_2$-alkyl, or A, B and the carbon atom to which they are bonded especially preferably represent saturated or unsaturated $C_5$-$C_7$-cycloalkyl in which one ring member is optionally replaced by oxygen or sulphur and which is optionally monosubstituted or disubstituted by $C_1$-$C_6$-alkyl, trifluoromethyl or $C_1$-$C_6$-alkoxy, with the proviso that, in this case, $Q^3$ especially preferably represents hydrogen or methyl, or A, B and the carbon atom to which they are bonded especially preferably represent $C_5$-$C_6$-cycloalkyl which is optionally substituted by an alkylenediyl group which optionally contains one or two oxygen or sulphur atoms which are not directly adjacent to each other and is optionally substituted by methyl or ethyl, or by an alkylenedioxyl or by an alkylenedithiol group, which group, together with the carbon atom to which it is bonded, forms a further five- or six-membered ring, with the proviso that, in this case, $Q^3$ especially preferably represents hydrogen or methyl, A, B and the carbon atom to which they are bonded especially preferably represent $C_3$-$C_6$-cycloalkyl or $C_5$-$C_6$-cycloalkenyl in which two substituents together with the carbon atoms to which they are bonded represent $C_2$-$C_4$-alkanediyl, $C_2$-$C_4$-alkenediyl or butandienediyl, each of which is optionally substituted by $C_1$-$C_2$-alkyl or $C_1$-$C_2$-alkoxy, with the proviso that, in this case, $Q^3$ especially preferably represents hydrogen or methyl, D especially preferably represents hydrogen, or represents $C_1$-$C_6$-alkyl, $C_3$-$C_6$-alkenyl, $C_1$-$C_4$-alkoxy-$C_2$-$C_3$-alkyl, each of which is optionally monosubstituted to trisubstituted by fluorine, or represents $C_3$-$C_6$-cycloalkyl which is optionally monosubstituted or disubstituted by $C_1$-$C_4$-alkyl, $C_1$-$C_4$-alkoxy or $C_1$-$C_2$-halogenoalkyl and in which one methylene group is optionally replaced by oxygen, or (but not in the case of the compounds of the formulae (I-1)) represents phenyl or pyridyl, each of which is optionally monosubstituted or disubstituted by fluorine, chlorine, bromine, $C_1$-$C_4$-alkyl, $C_1$-$C_4$-halogenoalkyl, $C_1$-$C_4$-alkoxy or $C_1$-$C_4$-halogenoalkoxy, or A and D jointly especially preferably represent $C_3$-$C_5$-alkanediyl which is optionally monosubstituted or disubstituted and in which one methylene group can be replaced by a carbonyl group (but not in the case of the compounds of the formula (I-1)), oxygen or sulphur, with $C_1$-$C_2$-alkyl or $C_1$-$C_2$-alkoxy being suitable substituents, or A and D (in the case of the compounds of the formula (I-1)) together with the atoms to which they are bonded represent one of the groups AD-1 to AD-10

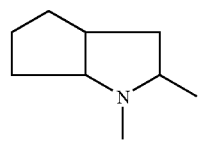

AD-1

-continued

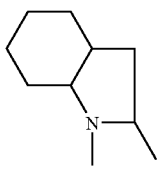
AD-2

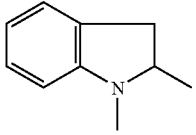
AD-3

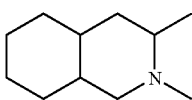
AD-4

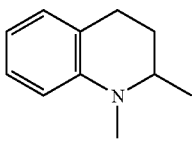
AD-5

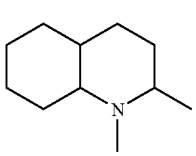
AD-6

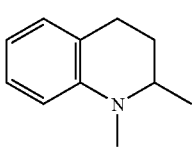
AD-7

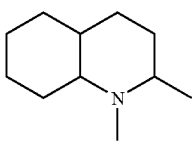
AD-8

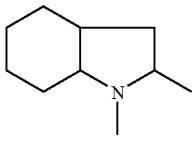
AD-9

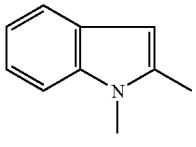
AD-10 or

A and $Q^1$ together especially preferably represent $C_3$-$C_4$-alkanediyl, in each case optionally monosubstituted or disubstituted by identical or different substituents from the series consisting of $C_1$-$C_2$-alkyl or $C_1$-$C_2$-alkoxy, or $Q^1$ especially preferably represents hydrogen, $Q^2$ especially preferably represents hydrogen, $Q^4$, $Q^5$ and $Q^6$ especially preferably independently of one another represent hydrogen or $C_1$-$C_3$-alkyl, $Q^3$ especially preferably represents hydrogen, $C_1$-$C_4$-alkyl or $C_3$-$C_6$-cycloalkyl which is optionally monosubstituted or disubstituted by methyl or methoxy, or $Q^3$ and $Q^4$ especially preferably together with the carbon atom to which they are bonded represent a saturated $C_5$-$C_6$ ring which is optionally substituted by $C_1$-$C_2$-alkyl or $C_1$-$C_2$-alkoxy and in which one ring member is optionally replaced by oxygen or sulphur, with the proviso that, in this case, A especially preferably represents hydrogen or methyl, or G especially preferably represents hydrogen (a) or one of the groups

 (b)

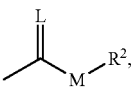 (c)

 (d)

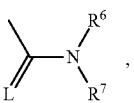 (e)

E or (f)

(g)

in particular (a), (b) or (c), in which

E represents a metal ion equivalent or an ammonium ion,

L represents oxygen or sulphur and

M represents oxygen or sulphur.

$R^1$ especially preferably represents $C_1$-$C_8$-alkyl, $C_2$-$C_{18}$-alkenyl, $C_1$-$C_4$-alkoxy-$C_1$-$C_2$-alkyl, $C_1$-$C_4$-alkylthio-$C_1$-$C_2$-alkyl, each of which is optionally monosubstituted to trisubstituted by fluorine or chlorine, or represents $C_3$-$C_6$-cycloalkyl which is optionally monosubstituted or disubstituted by fluorine, chlorine, $C_1$-$C_2$-alkyl or $C_1$-$C_2$-alkoxy and in which one or two ring members which are not directly adjacent are optionally replaced by oxygen, or represent phenyl which is optionally monosubstituted or disubstituted by fluorine, chlorine, bromine, cyano, nitro, $C_1$-$C_4$-alkyl, $C_1$-$C_4$-alkoxy, $C_1$-$C_2$-halogenoalkyl or $C_1$-$C_2$-halogenoalkoxy, $R^2$ especially preferably represents $C_1$-$C_8$-alkyl, $C_2$-$C_8$-alkenyl or $C_1$-$C_4$-alkoxy-$C_2$-$C_4$-alkyl, each of which is optionally monosubstituted to trisubstituted by fluorine, or represents $C_3$-$C_6$-cycloalkyl which is optionally substituted by $C_1$-$C_2$-alkyl or $C_1$-$C_2$-alkoxy, or represents phenyl or benzyl, each of which is optionally monosubstituted or disubstituted by fluorine, chlorine, bromine, cyano, nitro, $C_1$-$C_4$-alkyl, $C_1$-$C_3$-alkoxy, trifluoromethyl or trifluoromethoxy, $R^3$ especially preferably represents $C_1$-$C_6$-alkyl which is optionally monosubstituted to trisubstituted by fluorine, or represents phenyl which is optionally in each case monosubstituted by fluorine, chlorine, bromine, $C_1$-$C_4$-alkyl, $C_1$-$C_4$-alkoxy, trifluoromethyl, trifluoromethoxy, cyano or nitro, R[4] especially preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, or represents phenyl, phenoxy or phenylthio, each of which is optionally monosubstituted by fluorine, chlorine, bromine, nitro, cyano, $C_1$-$C_3$-alkoxy, $C_1$-$C_3$-halogenoalkoxy, $C_1$-$C_3$-alkylthio, $C_1$-$C_3$-halogenoalkylthio, $C_1$-$C_3$-alkyl or trifluoromethyl, R[5] especially preferably represents $C_1$-$C_6$-alkoxy or $C_1$-$C_6$-alkylthio, R[6] especially preferably represents hydrogen, $C_1$-$C_6$-alkyl, $C_3$-$C_6$-Cycloalkyl, $C_1$-$C_6$-alkoxy, $C_3$-$C_6$-alkenyl, $C_1$-$C_6$-alkoxy-$C_1$-$C_4$-alkyl, or represents phenyl which is optionally monosubstituted by fluorine, chlorine, bromine, trifluoromethyl, $C_1$-$C_4$-alkyl or $C_1$-$C_4$-alkoxy, or represents benzyl which is optionally monosubstituted by fluorine, chlorine, bromine, $C_1$-$C_4$-alkyl, trifluoromethyl or $C_1$-$C_4$-alkoxy, R[7] especially preferably represents $C_1$-$C_6$-alkyl, $C_3$-$C_6$-alkenyl or $C_1$-$C_6$-alkoxy-$C_1$-$C_4$-alkyl, R[6] and R[7] together especially preferably represent a $C_4$-$C_5$-alkylene radical which is optionally substituted by methyl or ethyl and in which one methylene group is optionally replaced by oxygen or sulphur.

In the definitions of radicals mentioned as being especially preferred, halogen represents fluorine, chlorine and bromine, in particular fluorine and chlorine.

W very especially preferably represents methoxy, ethoxy, n-propoxy, iso-propoxy, n-butoxy, iso-butoxy, sec-butoxy, methoxy-ethyloxy, ethoxy-ethyloxy, cyclopropyl-methoxy, cyclopentyl-methoxy or cyclohexyl-methoxy, X very especially preferably represents methyl or ethyl, Y very especially preferably represents chlorine or bromine, CKE very particularly preferably represents one of the groups

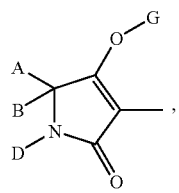
(1)

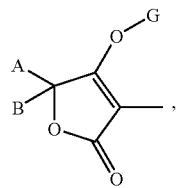
(2)

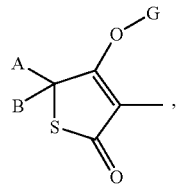
(3)

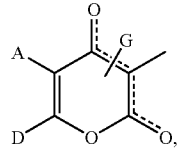
(4)

-continued

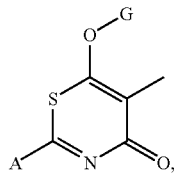
(5)

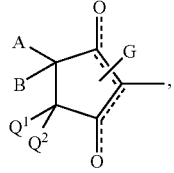
(6)

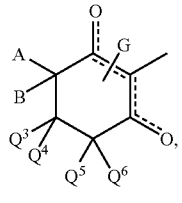
(7)

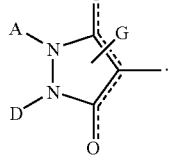
(8)

A very especially preferably represents hydrogen, or represents $C_1$-$C_4$-alkyl or $C_1$-$C_2$-alkoxy-$C_1$-$C_2$-alkyl, each of which is monosubstituted to trisubstituted by fluorine, or represents cyclopropyl, cyclopentyl or cyclohexyl, and only in the case of the compounds of the formula (I-5) represents phenyl which is optionally in each case substituted by fluorine, chlorine, bromine, methyl, ethyl, n-propyl, iso-propyl, methoxy, ethoxy, trifluoromethyl, trifluoromethoxy, cyano or nitro, B very especially preferably represents hydrogen, methyl or ethyl, or A, B and the carbon atom to which they are bonded very especially preferably represent saturated $C_5$-$C_6$-cycloalkyl in which one ring member is optionally replaced by oxygen or sulphur and which is optionally monosubstituted by methyl, ethyl, propyl, isopropyl, trifluoromethyl, methoxy, ethoxy, propoxy or butoxy, with the proviso that, in this case, $Q^3$ very especially preferably represents hydrogen, or A, B and the carbon atom to which they are bonded very especially preferably represent $C_6$-cycloalkyl which is optionally substituted by an alkylenedioxyl group containing two oxygen atoms which are not directly adjacent, with the proviso that, in this case, $Q^3$ very especially preferably represents hydrogen, or A, B and the carbon atom to which they are bonded very especially preferably represent $C_5$-$C_6$-cycloalkyl or $C_5$-$C_6$-cycloalkenyl in which two substituents together with the carbon atoms to which they are bonded represent $C_2$-$C_4$-alkanediyl or $C_2$-$C_4$-alkenediyl or butadienediyl, with the proviso that, in this case, $Q^3$ very especially preferably represents hydrogen, D very especially preferably represents hydrogen, or represents $C_1$-$C_4$-alkyl, $C_3$-$C_4$-alkenyl, $C_1$-$C_4$-alkoxy-$C_2$-$C_3$-alkyl, each of which is optionally monosubstituted to trisubstituted by fluorine, or represents cyclopropyl, cyclopentyl or cyclohexyl, or (but not in the case of compounds of the formulae (I-1)) represents phenyl or pyridyl, each of which is optionally monosubstituted by fluorine, chlorine, methyl, ethyl, n-propyl, iso-propyl, methoxy, ethoxy or trifluoromethyl, or A and D together very especially preferably represent $C_3$-$C_5$-alkanediyl which is optionally monosubstituted by methyl or methoxy and in which one carbon atom is optionally replaced by oxygen or sulphur, or represent the group AD-1

A and $Q^1$ together very especially preferably represent $C_3$-$C_4$-alkanediyl which is optionally monosubstituted or disubstituted by methyl or methoxy or $Q^1$ very especially preferably represents hydrogen, $Q^2$ very especially preferably represents hydrogen, $Q^4$, $Q^5$ and $Q^6$ very especially preferably independently of one another represent hydrogen or methyl, $Q^3$ very especially preferably represents hydrogen, methyl, ethyl or propyl, or $Q^3$ and $Q^4$ together with the carbon atom to which they are bonded very especially preferably represent a saturated $C_5$-$C_6$ ring which is optionally monosubstituted by methyl or methoxy, with the proviso that, in this case, A very especially preferably represents hydrogen, G very especially preferably represents hydrogen (a) or one of the groups

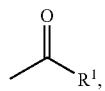  (b)

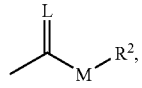  (c)

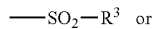  (d)

  (f)

E, in which

L represents oxygen or sulphur,

M represents oxygen or sulphur and

E represents an ammonium ion, $R^1$ very especially preferably represents $C_1$-$C_6$-alkyl, $C_2$-$C_{17}$-alkenyl, $C_1$-$C_2$-alkoxy-$C_1$-alkyl, $C_1$-$C_2$-alkylthio-$C_1$-alkyl or represents cyclopropyl or cyclohexyl, each of which is optionally monosubstituted by fluorine, chlorine, methyl or methoxy, or represents phenyl which is optionally monosubstituted by fluorine, chlorine, bromine, cyano, nitro, methyl, methoxy, trifluoromethyl or trifluoromethoxy, $R^2$ very especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, $R^3$ very especially preferably represents $C_1$-$C_8$-alkyl.

W especially represents methoxy, ethoxy, n-propoxy, iso-propoxy, n-butoxy, iso-butoxy, sec-butoxy, methoxy-ethyloxy, ethoxy-ethyloxy or cyclopropylmethoxy, X especially represents methyl or ethyl, Y especially represents chlorine, CKE especially represents one of the groups

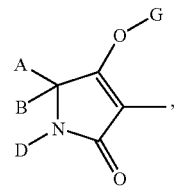  (1)

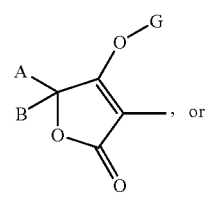  (2)

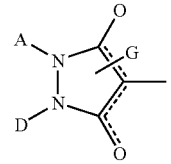  (8)

A especially represents hydrogen, methyl, ethyl, cyclopropyl, isopropyl, n-propyl, isobutyl, n-butyl, t-butyl or s-butyl (in particular hydrogen, methyl or ethyl), B especially represents hydrogen, methyl or ethyl, A, B and the carbon atom to which they are bonded especially represent saturated $C_5$-$C_6$-cycloalkyl in which one ring member is optionally replaced by oxygen and which is optionally monosubstituted by methyl, methoxy, ethoxy, n-propoxy, n-butoxy or trifluoromethyl (in particular methyl or methoxy), D especially represents hydrogen, methyl, ethyl, isopropyl, cyclopropyl or cyclohexyl, or A and D together especially represent $C_3$-$C_5$-alkanediyl or the group AD-1, G especially represents hydrogen (a) or one of the groups

  (b)

  (c)

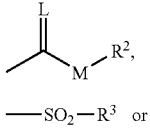  (d)

  (f)

E, in which

L represents oxygen,

M represents oxygen and

E represents an ammonium ion ($N^+(C_6H_{13})_4$), $R^1$ especially represents $C_1$-$C_8$-alkyl, $C_1$-$C_2$-alkoxy-$C_1$-alkyl, or $C_2$-$C_{17}$-alkenyl, $R^2$ especially represents $C_1$-$C_8$-alkyl or $C_2$-$C_6$-alkenyl, $R^3$ especially represents $C_1$-$C_4$-alkyl.

The abovementioned definitions of radicals or illustrations, in general or where preferred ranges have been mentioned, can be combined with each other as desired, that is to say combinations between the respective ranges and preferred ranges are also possible. They apply to the end products and, analogously, to the precursors and intermediates.

Preferred according to the invention are the compounds of the formula (I) which contain a combination of the meanings mentioned above as being preferred (preferable).

Particularly preferred according to the invention are the compounds of the formula (I) which contain a combination of the meanings mentioned above as being especially preferred.

Very particularly preferred according to the invention are the compounds of the formula (I) which contain a combination of the meanings mentioned above as being very especially preferred.

The compounds of the formula (I) with a combination of the meanings mentioned above preceded by "especially" are especially preferred in accordance with the invention.

Saturated or unsaturated hydrocarbon radicals, such as alkyl, alkanediyl or alkenyl, also in connection with hetero atoms, such as, for example, in alkoxy, can be in each case straight-chain or branched as far as this is possible.

Unless stated otherwise, optionally substituted radicals can be monosubstituted or polysubstituted, it being possible for the substituents to be identical or different in the case of the polysubstituted radicals.

Compounds of the formula (I-1-a) which may be mentioned individually in addition to the compounds mentioned in the preparation examples are those which follow:

TABLE 1

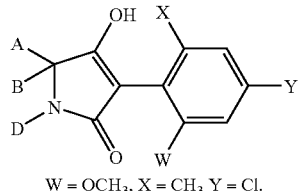

W = OCH$_3$, X = CH$_3$ Y = Cl.

| A | B | D |
|---|---|---|
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |

TABLE 1-continued

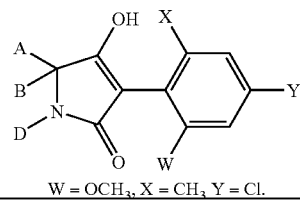

W = OCH$_3$, X = CH$_3$ Y = Cl.

| A | B | D |
|---|---|---|
| | —(CH$_2$)$_2$— | H |
| | —(CH$_2$)$_4$— | H |
| | —(CH$_2$)$_5$— | H |
| | —(CH$_2$)$_6$— | H |
| | —(CH$_2$)$_7$— | H |
| | —(CH$_2$)$_2$—O—(CH$_2$)$_2$— | H |
| | —CH$_2$—O—(CH$_2$)$_3$— | H |
| | —(CH$_2$)$_2$—S—(CH$_2$)$_2$— | H |
| | —CH$_2$—CHCH$_3$—(CH$_2$)$_3$— | H |
| | —(CH$_2$)$_2$—CHCH$_3$—(CH$_2$)$_2$— | H |
| | —(CH$_2$)$_2$—CHC$_2$H$_5$—(CH$_2$)$_2$— | H |
| | —(CH$_2$)$_2$—CHC$_3$H$_7$—(CH$_2$)$_2$— | H |
| | —(CH$_2$)$_2$—CHi-C$_3$H$_7$—(CH$_2$)$_2$— | H |
| | —(CH$_2$)$_2$—CHOCH$_3$—(CH$_2$)$_2$— | H |
| | —(CH$_2$)$_2$—CHOC$_2$H$_5$—(CH$_2$)$_2$— | H |
| | —(CH$_2$)$_2$—CHOC$_3$H$_7$—(CH$_2$)$_2$— | H |
| | —(CH$_2$)$_2$—CHO-i-C$_3$H$_7$—(CH$_2$)$_2$— | H |
| | —(CH$_2$)$_2$—C(CH$_3$)$_2$—(CH$_2$)$_2$— | H |
| | —CH$_2$—(CHCH$_3$)$_2$—(CH$_2$)$_2$— | H |
| | —CH$_2$—CH—(CH$_2$)$_2$—CH— with bridging CH$_2$ | H |
| | —CH$_2$—CH—CH—CH$_2$— with (CH$_2$)$_4$ bridge | H |
| | —CH$_2$—CH—CH—(CH$_2$)$_2$— with (CH$_2$)$_3$ bridge | H |
| | indane ring | H |
| | tetralin ring | H |
| | —(CH$_2$)$_3$— | H |
| | —(CH$_2$)$_4$— | H |
| | —CH$_2$—CHCH$_3$—CH$_2$— | H |
| | —CH$_2$—CH$_2$—CHCH$_3$— | H |
| | —CH$_2$—CHCH$_3$—CHCH$_3$— | H |
| | —CH$_2$—CH(OCH$_3$)—CH$_2$— | H |
| | —CH$_2$—CH=CH—CH$_2$— | H |
| | —CH$_2$—CH—CH— with CH$_2$—O—CH$_2$ bridge | H |
| | —CH$_2$—S—CH$_2$— | H |
| | —CH$_2$—S—(CH$_2$)$_2$— | H |
| | —(CH$_2$)$_2$—S—CH$_2$— | H |
| | —CH$_2$—CH—CH— with (CH$_2$)$_3$ bridge | H |

TABLE 1-continued

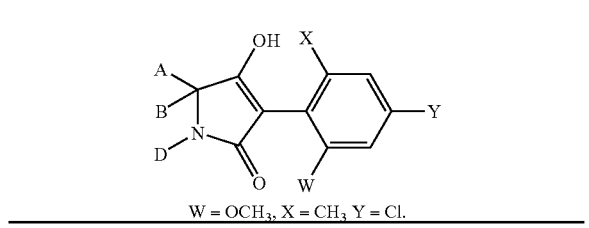

W = OCH₃, X = CH₃, Y = Cl.

| A | B | D |
|---|---|---|
| H | CH₃ | H |
| H | C₂H₅ | H |
| H | C₃H₇ | H |
| H | i-C₃H₇ | H |
| H | cyclopropyl | H |
| H | cyclopentylmethyl | H |
| H | cyclohexylmethyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentylmethyl | H |
| CH₃ | cyclohexylmethyl | H |
| —CH₂—CH—(CH₂—O—CH₂)—CH— | | H |
| C₂H₅ | CH₃ | H |
| C₂H₅ | C₂H₅ | H |

Table 2: A, B and D as shown in Table 1
  W=OCH₃; X=CH₃; Y=Br

Table 3: A, B and D as shown in Table 1
  W=OCH₃; X=C₂H₅; Y=Cl.

Table 4: A, B and D as shown in Table 1
  W=OCH₃; X=C₂H₅; Y=Br.

Table 5: A, B and D as shown in Table 1
  W=OC₂H₅; X=CH₃; Y=Cl.

Table 6: A, B and D as shown in Table 1
  W=OC₂H₅; X=C₂H₅; Y=Cl.

Compounds of the formula (I-2-a) which may be mentioned individually in addition to the compounds mentioned in the preparation examples are those which follow:

TABLE 7

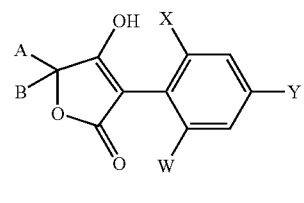

W = OCH₃, X = CH₃, Y = Cl.

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | C₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentylmethyl | CH₃ |
| cyclohexylmethyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —CH₂—O—(CH₂)₃— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHO-i-C₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with bridging CH₂ | |
| —CH₂—CH—CH—CH₂— with (CH₂)₄ bridge | |
| —CH₂—CH—CH—(CH₂)₂— with (CH₂)₃ bridge | |

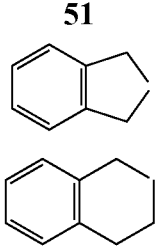

Table 8: A and B as shown in Table 7
 W=OCH$_3$; X=CH$_3$; Y=Br.
Table 9: A and B as shown in Table 7
 W=OCH$_3$; X=C$_2$H$_5$; Y=Cl.
Table 10: A and B as shown in Table 7
 W=OCH$_3$; X=C$_2$H$_5$; Y=Br.
Table 11: A and B as shown in Table 7
 W=OC$_2$H$_5$; X=CH$_3$; Y=Cl.
Table 12: A and B as shown in Table 7
 W=OC$_2$H$_5$; X=C$_2$H$_5$; Y=Cl.

The following compounds of the formula (I-8-a) may be mentioned individually in addition to compounds mentioned in the preparation examples:

TABLE 13

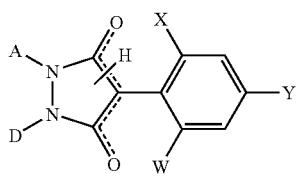

W = OCH$_3$, X = CH$_3$, Y = Cl.

| A | D |
|---|---|
| CH$_3$ | CH$_3$ |
| CH$_3$ | —(CH$_2$)$_2$OH— |
| CH$_3$ | —(CH$_2$)$_2$OCH$_3$— |
| CH$_3$ | —(CH$_2$)$_2$—O—(CH$_2$)$_2$—OCH$_3$— |
| —(CH$_2$)$_2$—O—CH$_3$— | —(CH$_2$)$_2$—O—CH$_3$— |
| —(CH$_2$)$_2$—O—(CH$_2$)$_2$—OCH$_3$— | —(CH$_2$)$_2$—O—(CH$_2$)$_2$—OCH$_3$— |
|  | —(CH$_2$)$_3$— |
|  | —(CH$_2$)$_4$— |
|  | —(CH2)$_2$—O—(CH$_2$)$_2$— |

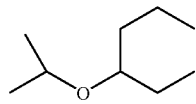
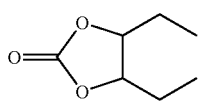
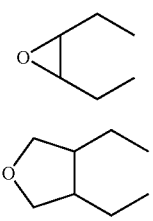

TABLE 13-continued

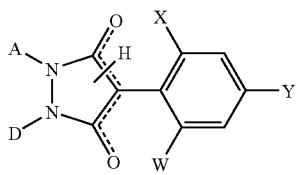

W = OCH$_3$, X = CH$_3$, Y = Cl.

| A | D |
|---|---|
|  | (structures shown) |

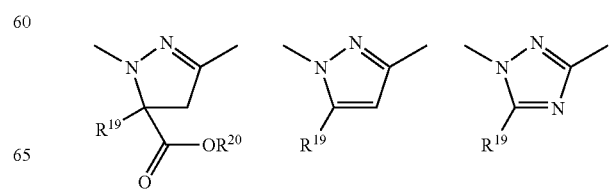

Table 14: A and D as shown in Table 13
 W=OCH$_3$; X=CH$_3$; Y=Br.
Table 15: A and D as shown in Table 13
 W=OCH$_3$; X=C$_2$H$_5$; Y=Cl.
Table 16: A and D as shown in Table 13
 W=OCH$_3$; X=C$_2$H$_5$; Y=Br.
Table 17: A and D as shown in Table 13
 W=OC$_2$H$_5$; X=CH$_3$; Y=Cl.
Table 18: A and D as shown in Table 13
 W=OC$_2$H$_5$; X=C$_2$H$_5$; Y=Cl.

Preferred meanings of the groups mentioned above in connection with the compounds improving crop plant tolerance ("herbicide safeners") of the formulae (IIa), (IIb), (IIc), (IId) and (IIe) are defined hereinbelow.

n preferably represents the numbers 0, 1, 2, 3 or 4.

A$^1$ preferably represents one of the divalent heterocyclic groups outlined hereinbelow -continued

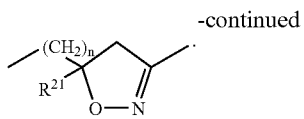

A² preferably represents methylene or ethylene, each of which is optionally substituted by methyl, ethyl, methoxycarbonyl or ethoxycarbonyl.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- oder i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents methyl, ethyl, n- or i-propyl, each of which is optionally substituted by fluorine, chlorine and/or bromine.

$R^{17}$ preferably represents hydrogen, or represents methyl, ethyl, n- or i-propyl, n-, i-, s- or t-butyl, propenyl, butenyl, propinyl or butinyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl.

$R^{18}$ preferably represents hydrogen, or represents methyl, ethyl, n- or i-propyl, n-, i-, s- or t-butyl, propenyl, butenyl, propinyl or butinyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl or together with $R^{17}$ represents one of the radicals —CH₂—O—CH₂—CH₂— and —CH₂—CH₂—O—CH₂—CH₂— which are optionally substituted by methyl, ethyl, furyl, phenyl, a fused benzene ring or by two substituents which, together with the carbon atom to which they are bonded, form a 5- or 6-membered carbocycle.

$R^{19}$ preferably represents hydrogen, cyano, fluorine, chlorine, bromine, or represents methyl, ethyl, n- or i-propyl, cyclopropyl, cyclobutyl, cyclopentyl, cyclohexyl or phenyl, each of which is optionally substituted by fluorine, chlorine and/or bromine.

$R^{20}$ preferably represents hydrogen, or represents methyl, ethyl, n- or i-propyl, n-, i-, s- or t-butyl, in each case optionally substituted by hydroxyl, cyano, fluorine, chlorine, methoxy, ethoxy, n- or i-propoxy.

$R^{21}$ preferably represents hydrogen, cyano, fluorine, chlorine, bromine, or represents methyl, ethyl, n- or i-propyl, n-, i-, s- or t-butyl, cyclopropyl, cyclobutyl, cyclopentyl, cyclohexyl or phenyl, each of which is optionally substituted by fluorine, chlorine and/or bromine.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, or represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, each of which is optionally substituted by cyano, fluorine, chlorine, methoxy, ethoxy, n- or i-propoxy, or represents cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, each of which is optionally substituted by cyano, fluorine, chlorine, bromine, methyl, ethyl, n- or i-propyl.

$R^{25}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propinyl or butinyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl.

$R^{26}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propinyl or butinyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl, or represents phenyl which is optionally substituted by nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, or together with $R^{25}$ represents butane-1,4-diyl (trimethylene), pentane-1,5-diyl, 1-oxabutane-1,4-diyl or 3-oxapentane-1,5-diyl, each of which is optionally substituted by methyl or ethyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very especially preferred as herbicide safeners according to the invention are listed in the table which follows.

TABLE

Examples of the compounds of the formula (IIa)

| Example No | (Positions) $(X^1)_n$ | $A^1$ | $R^{14}$ |
|---|---|---|---|
| IIa-1 | (2) Cl, (4) Cl | 1,3-dimethyl-pyrazoline with H3C and C(=O)OCH3 substituent | OCH$_3$ |
| IIa-2 | (2) Cl, (4) Cl | 1,3-dimethyl-pyrazoline with H3C and C(=O)OC2H5 substituent | OCH$_3$ |
| IIa-3 | (2) Cl, (4) Cl | 1,3-dimethyl-pyrazoline with H3C and C(=O)OCH3 substituent | OC$_2$H$_5$ |
| IIa-4 | (2) Cl, (4) Cl | 1,3-dimethyl-pyrazoline with H3C and C(=O)OC2H5 substituent | OC$_2$H$_5$ |
| IIa-5 | (2) Cl | 1,3-dimethyl-5-phenyl-pyrazole | OCH$_3$ |
| IIa-6 | (2) Cl, (4) Cl | 1,3-dimethyl-5-phenyl-pyrazole | OCH$_3$ |
| IIa-7 | (2) F | 1,3-dimethyl-5-phenyl-pyrazole | OCH$_3$ |
| IIa-8 | (2) F | 1,3-dimethyl-5-(2-chlorophenyl)-pyrazole | OCH$_3$ |
| IIa-9 | (2) Cl, (4) Cl | 1,3-dimethyl-5-trichloromethyl-1,2,4-triazole | OC$_2$H$_5$ |
| IIa-10 | (2) Cl, (4) CF$_3$ | 1,3-dimethyl-5-phenyl-1,2,4-triazole | OCH$_3$ |
| IIa-11 | (2) Cl | 1,3-dimethyl-5-(2-fluorophenyl)-pyrazole | OCH$_3$ |
| IIa-12 | — | 3,5-dimethyl-5-phenyl-isoxazoline | OC$_2$H$_5$ |
| IIa-13 | (2) Cl, (4) Cl | 1,3-dimethyl-5-methyl-pyrazole | OC$_2$H$_5$ |

TABLE-continued

Examples of the compounds of the formula (IIa)

(IIa)

| Example No | (Positions) $(X^1)_n$ | $A^1$ | $R^{14}$ |
|---|---|---|---|
| IIa-14 | (2) Cl, (4) Cl | 1-methyl-3-methyl-5-(iso-propyl)pyrazol-5-yl | $OC_2H_5$ |
| IIa-15 | (2) Cl, (4) Cl | 1-methyl-3-methyl-5-(tert-butyl)pyrazol-5-yl | $OC_2H_5$ |
| IIa-16 | (2) Cl, (4) Cl | 5-ethyl-3-methyl-4,5-dihydroisoxazol-5-yl | $OC_2H_5$ |
| IIa-17 | (2) Cl, (4) Cl | 3,5-dimethyl-4,5-dihydroisoxazol-5-yl | $OC_2H_5$ |
| IIa-18 | — | 3-methyl-5-phenyl-4,5-dihydroisoxazol-5-yl | OH |

Examples of the compounds of the formula (IIb) which are very especially preferred as herbicide safeners according to the invention are listed in the table which follows.

TABLE
Examples of the compounds of the formula (IIb)

(IIb)

| Example No. | (Position) $X^2$ | (Position) $X^3$ | $A^2$ | $R^{15}$ |
|---|---|---|---|---|
| IIb-1 | (5) Cl | — | $CH_3$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_3$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | $OCH_2CH(CH_2OCH_2CH=CH_2)OCH_3$ |
| IIb-13 | (5) Cl | — | $CH(CH_2OCH_2CH=CH_2)$ | $OCH_2CH=CH_2$ |
| IIb-14 | (5) Cl | — | $CH(C_2H_5)$ | $OC_2H_5$ |
| IIb-15 | (5) Cl | — | $CH(CH_3)$ | $OCH_3$ |

Examples of the compounds of the formula (IIc) which are very especially preferred as herbicide safeners according to the invention are listed in the table which follows.

TABLE

Examples of the compounds of the formula (IIc)

(IIc)

$$R^{16}-C(=O)-N(R^{17})(R^{18})$$

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 2,2-dimethyl-3-methyl-oxazolidine (N-methyl-2,2-dimethyloxazolidine) |
| IIc-3 | $CHCl_2$ | N-methyl-2,2-dimethyl-4-methyl-oxazolidine |
| IIc-4 | $CHCl_2$ | N-methyl-spiro[oxazolidine-cyclohexane] |
| IIc-5 | $CHCl_2$ | N-methyl-2,2-dimethyl-5-phenyl-oxazolidine |
| IIc-6 | $CHCl_2$ | N,3-dimethyl-benzo[1,4]oxazine |
| IIc-7 | $CHCl_2$ | N-methyl-2,2-dimethyl-5-(furan-2-yl)-oxazolidine |

TABELLE

Examples of the compounds of the formula (IId)

(IId)

| Example No. | $R^{22}$ | $R^{23}$ | $R^{24}$ | (Positions) $(X^4)_n$ | (Positions) $(X^5)_n$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2-O-CH_3$ | (2) $OCH_3$ | — |

Examples of the compounds of the formula (IId) which are very especially preferred as herbicide safeners according to the invention are listed in the table which follows.

Examples of the compounds of the formula (IIe) which are very especially preferred as herbicide safeners according to the invention are listed in the table which follows.

TABLE

Examples of the compounds of the formula (IIe)

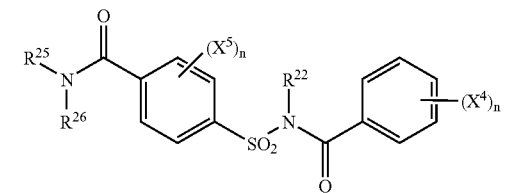

(IIe)

| Example No. | $R^{22}$ | $R^{25}$ | $R^{26}$ | (Positions) $(X^4)_n$ | (Positions) $(X^5)_n$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | △ | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | △ | (2) $OCH_3$ (5) $CH_3$ | — |
| IIe-12 | H | $CH_3$ | $CH_3$ | (2) $OCH_3$ (5) $CH_3$ | — |

Cloquintocet-mexyl, fenchlorazol-ethyl, isoxadifen-ethyl, mefenpyr-diethyl, furilazole, fenclorim, cumyluron, dymron, dimepiperate and the compounds IIe-5 and IIe-11 are most preferred as the compound which improves crop plant tolerance [component (b')], with cloquintocet-mexyl and mefenpyr-diethyl being especially preferred.

The compounds of the general formula (IIa) to be used in accordance with the invention as safeners are known and/or can be prepared by methods known per se (cf. WO-A-91/07874, WO-A-95/07897).

The compounds of the general formula (IIb) to be used in accordance with the invention as safeners are known and/or can be prepared by methods known per se (cf. EP-A-191736).

The compounds of the general formula (IIc) to be used in accordance with the invention as safeners are known and/or can be prepared by methods known per se (cf. DE-A-2218097, DE-A-2350547).

The compounds of the general formula (IId) to be used in accordance with the invention as safeners are known and/or can be prepared by methods known per se (cf. DE-A-19621522/U.S. Pat. No. 6,235,680).

The compounds of the general formula (IIe) to be used in accordance with the invention as safeners are known and/or can be prepared by methods known per se (cf. WO-A-99/66795/U.S. Pat. No. 6,251,827).

Examples of the selectively herbicidal combinations according to the invention of in each case one active compound of the formula (I) and in each case one of the above-defined safeners are listed in the table which follows.

TABLE

Examples of the combinations according to the invention

| Active compounds of the formula (I) | Safener |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-1 | IIe-5 |
| I-2 | cloquintocet-mexyl |
| I-2 | fenchlorazole-ethyl |
| I-2 | isoxadifen-ethyl |
| I-2 | mefenpyr-diethyl |
| I-2 | furilazole |
| I-2 | fenclorim |
| I-2 | cumyluron |
| I-2 | daimuron/dymron |
| I-2 | dimepiperate |
| I-2 | IIe-11 |
| I-2 | IIe-5 |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-5 |
| I-3 | IIe-11 |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-4 | IIe-5 |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-5 |
| I-5 | IIe-11 |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-5 |
| I-6 | IIe-11 |
| I-7 | cloquintocet-mexyl |
| I-7 | fenchlorazole-ethyl |
| I-7 | isoxadifen-ethyl |
| I-7 | mefenpyr-diethyl |
| I-7 | furilazole |
| I-7 | fenclorim |

TABLE-continued

Examples of the combinations according to the invention

| Active compounds of the formula (I) | Safener |
|---|---|
| I-7 | cumyluron |
| I-7 | daimuron/dymron |
| I-7 | dimepiperate |
| I-7 | IIe-5 |
| I-7 | IIe-11 |
| I-8 | cloquintocet-mexyl |
| I-8 | fenchlorazole-ethyl |
| I-8 | isoxadifen-ethyl |
| I-8 | mefenpyr-diethyl |
| I-8 | furilazole |
| I-8 | fenclorim |
| I-8 | cumyluron |
| I-8 | daimuron/dymron |
| I-8 | dimepiperate |
| I-8 | IIe-5 |
| I-8 | IIe-11 |

Surprisingly, it has now been found that the above-defined active compound combinations of substituted cyclic ketoenols of the general formula (I) and safeners (antidotes) from the above group (b') are not only very well tolerated by useful plants, but also have a particularly high herbicidal activity and can be used in a variety of crops, in particular in cereals (mainly wheat), but also in soybeans, potatoes, maize and rice, for the selective control of weeds.

It must be considered as surprising that, from a multiplicity of known safeners or antidotes which are capable of antagonizing the damaging effect of a herbicide on the crop plants, it is precisely the abovementioned compounds of group (b') which are capable of virtually completely compensating for the harmful effect of substituted cyclic ketoenols on the crop plants without adversely affecting the herbicidal activity towards the weeds to a substantial degree.

What must be emphasized in this context is the particularly advantageous activity of the particularly and most preferred components from group (b'), in particular with regard to leaving cereal plants, such as, for example, wheat, barley and rye, but also maize and rice, as crop plants unharmed.

If, for example, in accordance with process (A) ethyl N-(2-methyl-4-chloro-6-methoxyphenylacetyl)-1-aminocyclohexanecarboxylate is used as starting material, the course of the process according to the invention can be represented by the following equation:

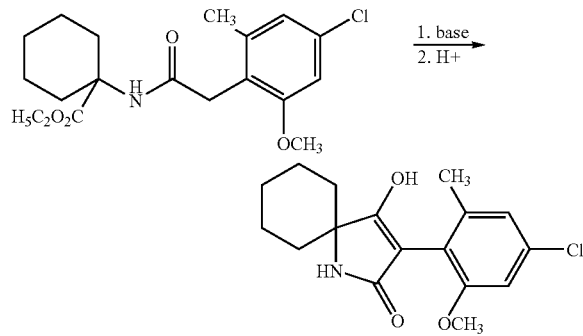

If for example, in accordance with process (B) ethyl O-(2-ethyl-4-chloro-6-methoxyphenylacetyl)-2-hydroxyisobutyrate is used, the course of the process according to the invention can be represented by the following equation:

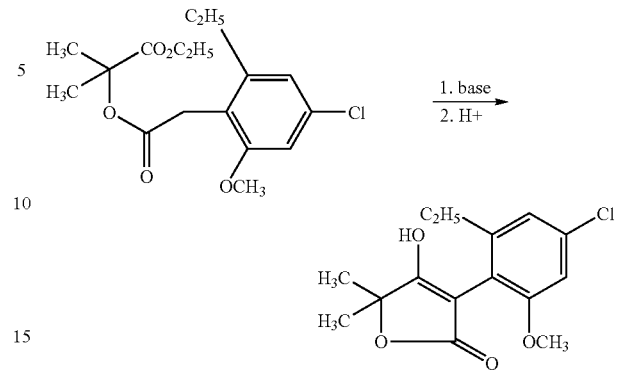

If, for example, in accordance with process (C) ethyl 2-(2-methyl-4-chloro-6-methoxy-phenyl)-4-(4-methoxy)benzyhnercapto-4-methyl-3-oxovalerate is used, the course of the process according to the invention can be represented by the following equation:

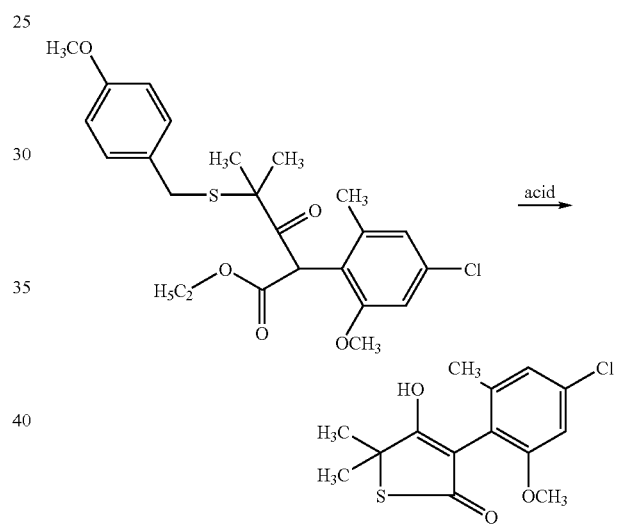

If, for example, in accordance with process (D) chlorocarbonyl 2-(2-ethyl-4-chloro-6-methoxy)phenyl) ketene and acetone are used as starting compounds, the course of the process according to the invention can be represented by the following equation:

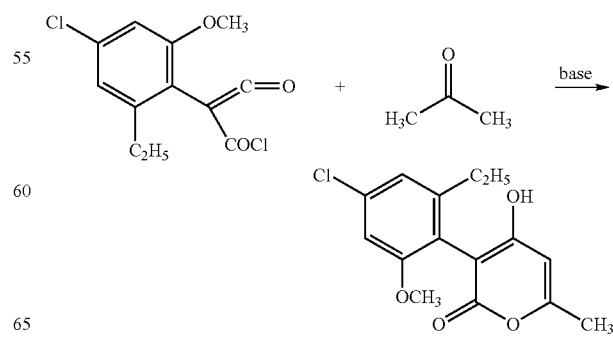

If, for example, in accordance with process (E) chlorocarbonyl 2-(2-ethyl-4-chloro-6-methoxy)phenyl) ketene and thiobenzamide are used as starting compounds, the course of the process according to the invention can be represented by the following equation:

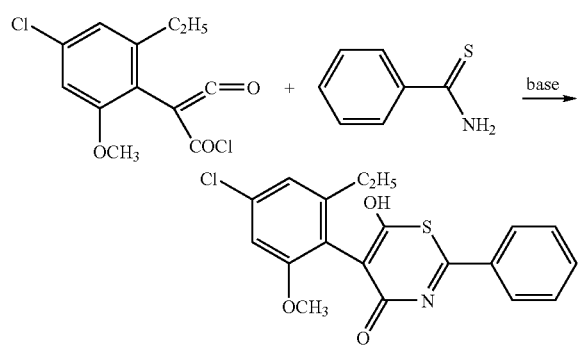

If, for example, in accordance with process (F) ethyl 5-(2-ethyl-4-chloro-6-methoxyphenyl)-2,3-trimethylene-4-oxovalerate is used, the course of the process according to the invention can be represented by the following equation:

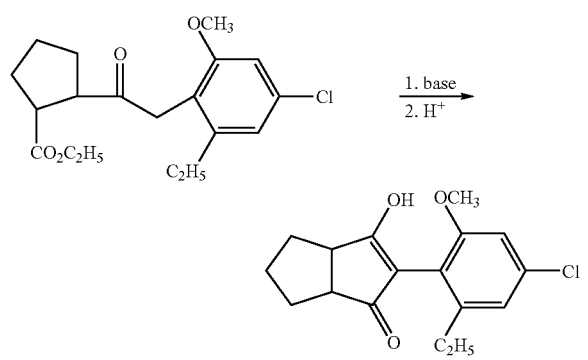

If, for example, in accordance with process (G) ethyl 5-[(2-ethyl-4-chloro-6-methoxy)phenyl]-2-methyl-5-oxo-hexanoate is used as starting material, the course of the process according to the invention can be represented by the following equation:

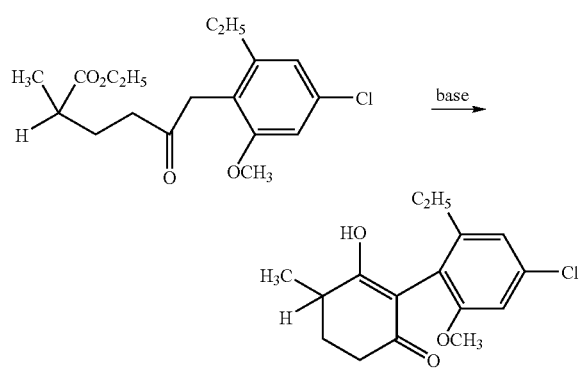

If, for example, in accordance with process (Hα) hexahydropyridazine and chlorocarbonyl 2-(2-ethyl-4-chloro-6-methoxy)phenyl ketene are used as starting compounds, the course of the process according to the invention can be represented by the following equation:

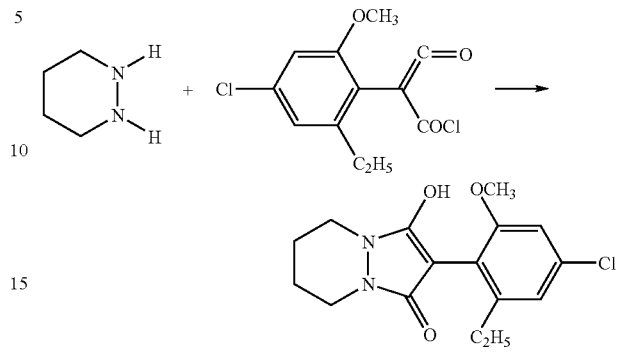

If, for example, in accordance with process (H) hexahydropyridazine and dimethyl (2-ethyl-4-chloro-6-methoxy)phenylmalonate are used as starting materials, the course of the process according to the invention can be represented by the following equation:

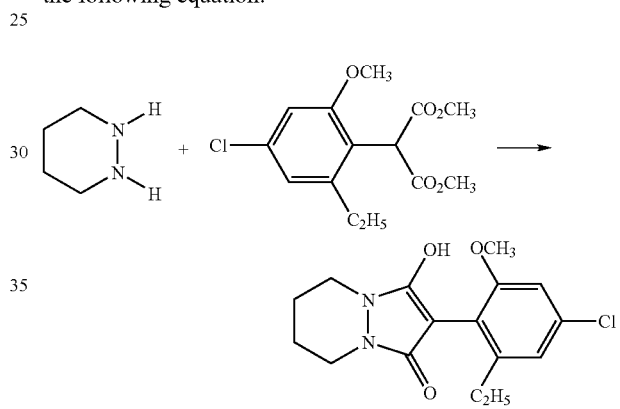

If, for example, in accordance with process (Hγ) 1-ethoxycarbonyl-2-[(2-methyl-4-bromo-6-methoxy)phenylacetyl] hexahydropyridazine is used as starting material, the course of the reaction can be represented by the following equation:

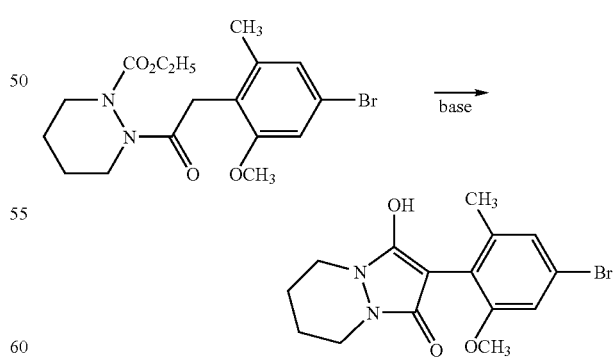

If, for example, in accordance with process (Iα) 3-(2-methyl-4-chloro-6-methoxyphenyl)-5,5-dimethylpyrrolidine-2,4-dione and pivaloyl chloride are used as starting materials, the course of the process according to the invention can be represented by the following equation:

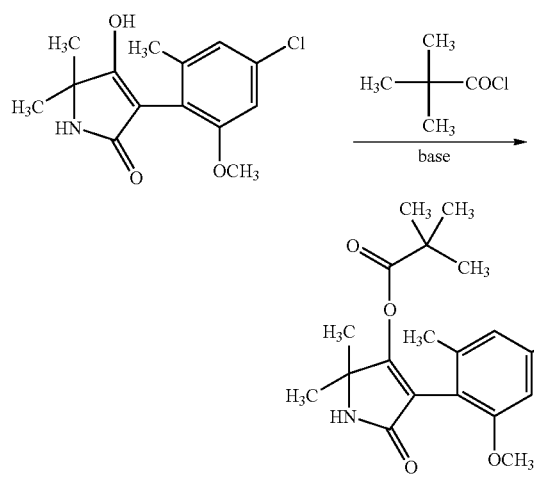

If, for example, in accordance with process (Iβ) 3-(2-ethyl-4-chloro-6-methoxyphenyl)-4-hydroxy-5-phenyl-Δ³-dihydrofuran-2-one and acetic anhydride are used as starting materials, the course of the process according to the invention can be represented by the following equation:

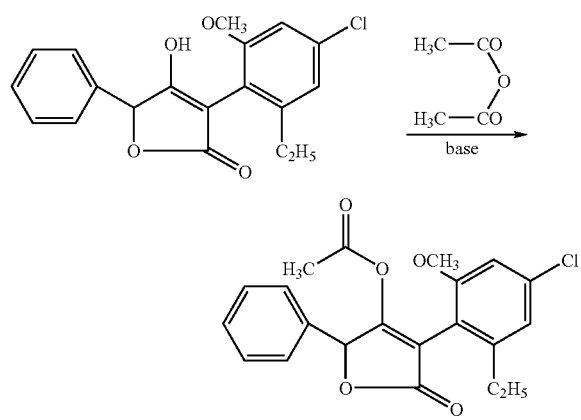

If, for example, in accordance with process (J) 8-[(2-ethyl-4-chloro-6-methoxy)phenyl]-1-azabicyclo-[4.3.0¹,⁶]-nonane-7,9-dione and ethoxyethyl chloroformate are used as starting materials, the course of the process according to the invention can be represented by the following equation:

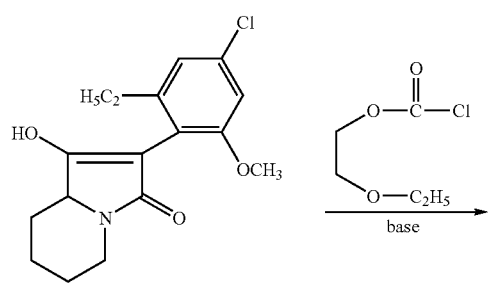

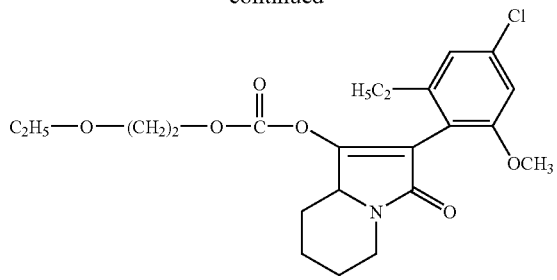

If, for example, in accordance with process (K), 3-(2-ethyl-4-chloro-6-methoxyphenyl)-4hydroxy-5-methyl-6-(3-pyridyl)pyrone and methyl chloromonothioformate are used as starting materials, the course of the reaction can be represented by the following equation:

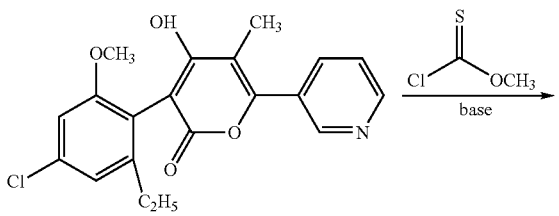

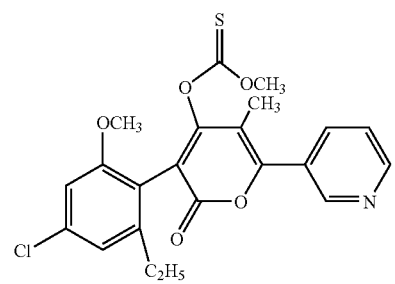

If, for example, in accordance with process (L) 3-(2-methyl-4-chloro-6-methoxyphenyl)-5,5-pentamethylenepyrrolidine-2,4-dione and methanesulphonyl chloride are used as starting materials, the course of the reaction can be represented by the following equation:

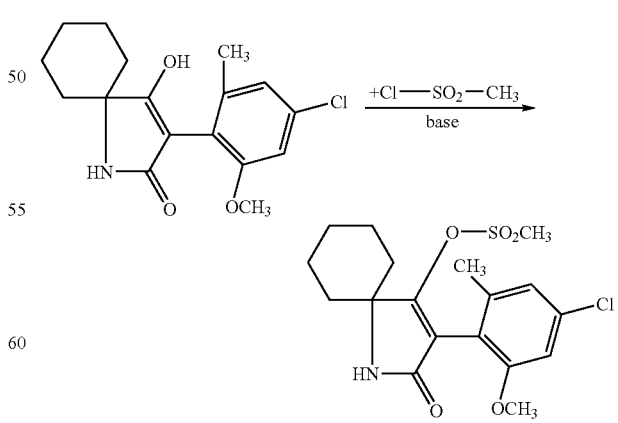

If, for example, in accordance with process (M) 3-(2-ethyl-4-chloro-6-methoxyphenyl)-4-hydroxy-5,5-dimethyl-Δ³-dihydrofuran-2-one and 2,2,2-trifluoroethyl methanechlorothiophosphonate are used as starting materials, the course of the reaction can be represented by the following equation:

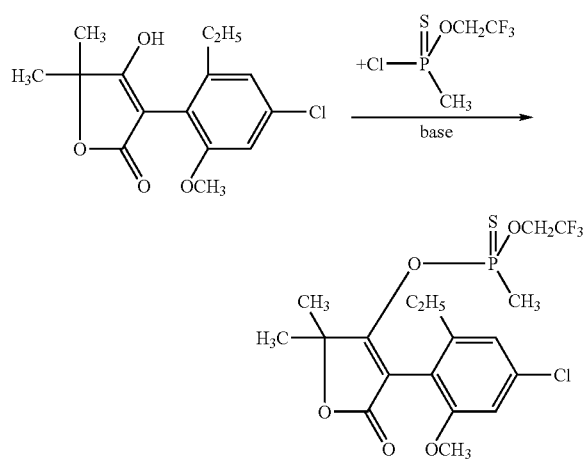

If, for example, in accordance with process (N), 3-(2-ethyl-4-chloro-6-methoxyphenyl)-5-cyclopropyl-5-methylpyrrolidine-2,4-dione and NaOH are used as components, the course of the process according to the invention can be represented by the following equation:

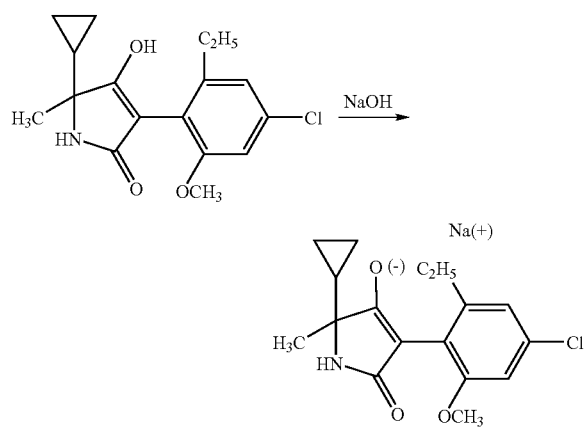

If, for example, in accordance with process (O), variant α, 3-(2-ethyl-4-chloro-6-methoxyphenyl)-4-hydroxy-5-tetramethylene-Δ³-dihydrofuran-2-one and ethyl isocyanate are used as starting materials, the course of the reaction can be represented by the following equation:

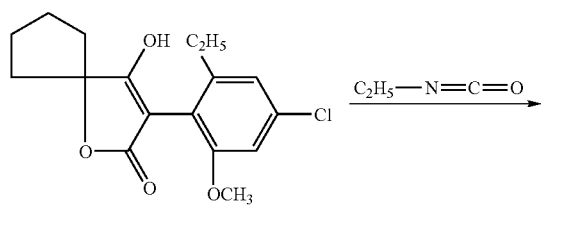

-continued

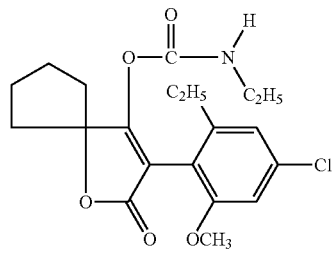

If, for example, in accordance with process (O), variant β, 3-(2-methyl-4-chloro-6-methoxyphenyl)-5-methylpyrrolidine-2,4-dione and dimethylcarbamoyl chloride are used as starting materials, the course of the reaction can be represented by the following equation:

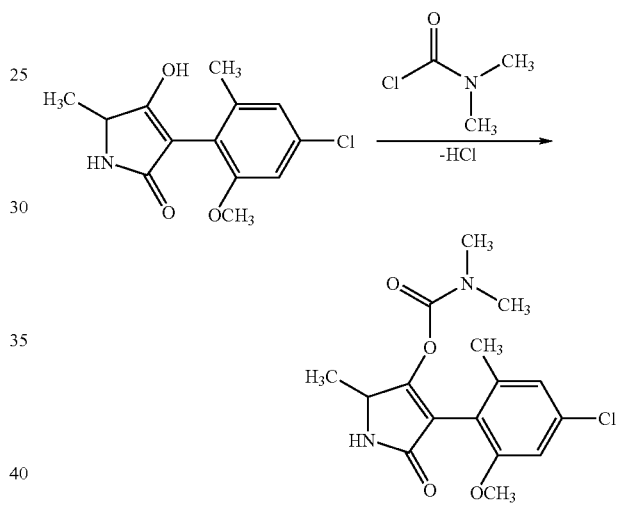

If, for example, in accordance with proess (P), 3-(2-bromo-4-chloro-6-ethylphenyl)-5,5-dimethylpyrrolidine-2,4-dione and sodium methoxide are used as starting materials, the course of the reaction can be represented by the following scheme:

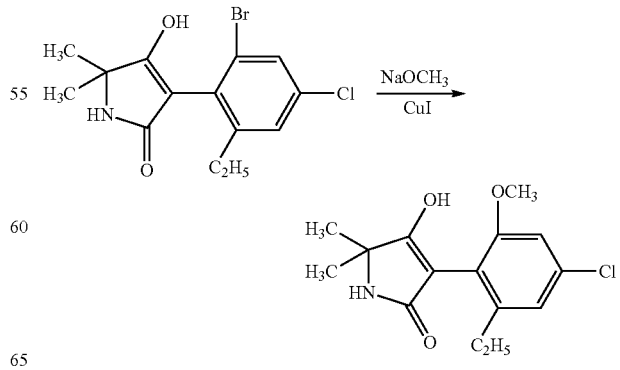

The compounds of the formula (II)

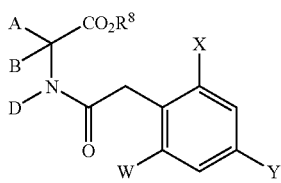
(II)

in which
A, B, D, W, X, Y and $R^8$ have the abovementioned meanings
and which are required as starting materials in process (a) according to the invention
are new.

The acylamino acid esters of the formula (II) are obtained, for example, when amino acid derivatives of the formula (XXIII)

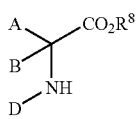
(XXIII)

in which
A, B, $R^8$ and D have the abovementioned meanings
are acylated with substituted phenylacetic acid derivatives of the formula (XXIV)

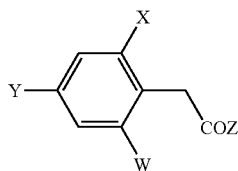
(XXIV)

in which
W, X and Y have the above-mentioned meanings and
Z represents a leaving group introduced by reagents for the activation of carboxylic acids, such as carbonyldiimidazole, carbonyldiimides (such as, for example, dicyclohexylcarbodiimide), phosphorylating reagents (such as, for example, $POCl_3$, BOP—Cl), halogenating agents, for example thionyl chloride, oxalyl chloride, phosgene or chloroformic esters,
(Chem. Reviews 52, 237-416 (1953); Bhattacharya, Indian J. Chem. 6, 341-5, 1968) or when acylamino acids of the formula (XXV)

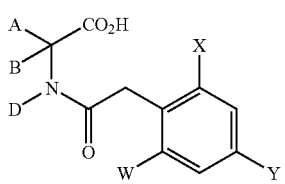

in which
A, B, D, W, X and Y have the abovementioned meanings
are esterified (Chem. Ind. (London) 1568 (1968)).

The compounds of the formula (XXV)

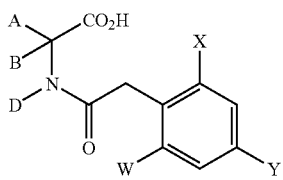

in which
A, B, D, W, X and Y have the abovementioned meanings
are new.

The compounds of the formula (XXV) are obtained when amino acids of the formula (XXVI)

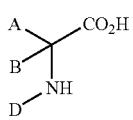
(XXVI)

in which
A, B and D have the abovementioned meanings
are acylated with substituted phenylacetic acid derivatives of the formula (XXIV)

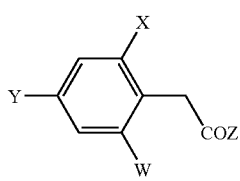
(XXIV)

in which
W, X and Y have the abovementioned meanings and
Z has the abovementioned meaning
for example in a Schotten-Baumann reaction (Organikum [Laboratory Practical in Organic Chemistry], VEB Deutscher Verlag der Wissenschaften, Berlin 1977, p. 505).

The compounds of the formula (XXIV) are new. They can be prepared by processes known in principle and as can be seen from the examples (see, for example, H. Henecka, Houben-Weyl, Methoden der Organischen Chemie [Methods in Organic Chemistry], Vol. 8, pp. 467-$469$ (1952)).

The compounds of the formula (XXIV) are obtained, for example, by reacting substituted phenylacetic acids of the formula (XXVII)

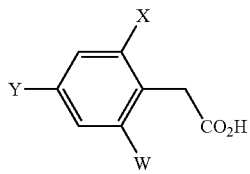

(XXVII)

in which
W, X and Y have the abovementioned meanings
with halogenating agents (for example thionyl chloride, thionyl bromide, oxalyl chloride, phosgene, phosphorus trichloride, phosphorus tribromide or phosphorus pentachloride), phosphonylating reagents (such as, for example, $POCl_3$, BOP—Cl), carbonyldiimidazole, carbonyldiimides (for example dicyclohexylcarbodiimide), if appropriate in the presence of a diluent (for example optionally chlorinated aliphatic or aromatic hydrocarbons such as toluene or methylene chloride or ethers, for example tetrahydrofuran, dioxane, methyl tert-butyl ether) at temperatures of from −20° C. to 150° C., preferably from −10° C. to 100° C.

Some of the compounds of the formulae (XXI) and (XXVI) are known and/or can be synthesized by known processes (see, for example, Compagnon, Miocque Ann. Chim. (Paris) [14] 5, pp. 11-22, 23-27 (1970)).

The substituted cyclic amino carboxylic acids of the formula (XXVI) in which A and B form a ring are generally obtained by means of a Bucherer-Bergs synthesis or a Strecker synthesis, where they are obtained in each case in various isomeric forms. Thus, the conditions of the Bucherer-Bergs synthesis preferentially give the isomers (for simplicity's sake termed β hereinbelow) in which the radicals R and the carboxyl group are in the equatorial position, while the conditions of the Strecker synthesis preferentially give the isomers (for simplicity's sake termed α hereinbelow) where the amino group and the radicals R are in the equatorial position.

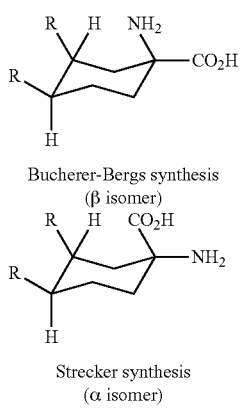

Bucherer-Bergs synthesis
(β isomer)

Strecker synthesis
(α isomer)

(L. Munday, J. Chem. Soc. 4372 (1961); J. T. Eward, C. Jitrangeri, Can. J. Chem. 53, 3339 (1975).

Furthermore, the starting substances of the formula (II)

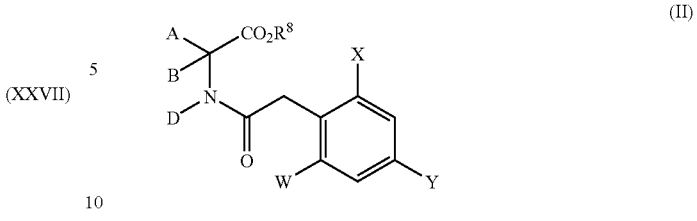

(II)

where
A, B, D, W, X, Y and $R^8$ have the abovementioned meanings
and which are used in the above process (A)
can be prepared when amino nitrites of the formula (XXVIII)

(XXVIII)

in which
A, B and D have the abovementioned meanings
are reacted with substituted phenylacetic acid derivatives of the formula (XXIV)

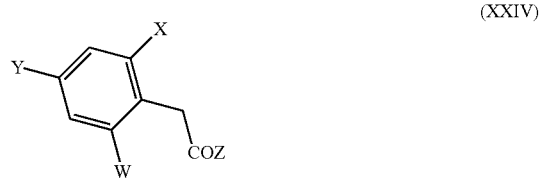

(XXIV)

in which
W, X, Y and Z have the abovementioned meanings
to give compounds of the formula (XXIX)

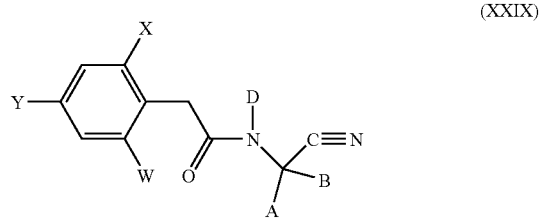

(XXIX)

in which
A, B, D, W, X and Y have the abovementioned meanings
and these are subsequently subjected to alcoholysis under acidic conditions.

The compounds of the formula (XXIX) are also new.

The compounds of the formula (III)

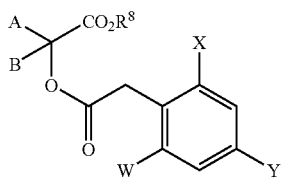
(III)

in which
A, B, W, X, Y and $R^8$ have the abovementioned meanings
and which are required as starting substances in process (B) according to the invention
are new.

They can be prepared by methods known in principle.

Thus, the compounds of the formula (III) are obtained, for example, when 2-hydroxy carboxylic esters of the formula (XXX-A)

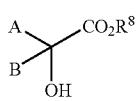
(XXX-A)

in which
A, B and $R^8$ have the abovementioned meanings
are acylated with substituted phenylacetic acid derivatives of the formula (XXIV)

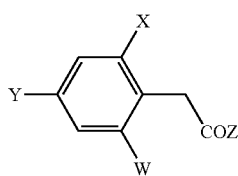
(XXIV)

in which
W, X and Y have the abovementioned meanings
(Chem. Reviews 52, 237-416 (1953)).

Furthermore, compounds of the formula (III) are obtained when substituted phenylacetic acids of the formula (XXVII)

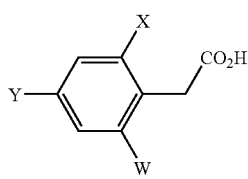
(XXVII)

in which
W, X and Y have the abovementioned meanings
are alkylated with -halogeno carboxylic esters of the formula (XXX-B)

(XXX-B)

in which
A, B and $R^8$ have the abovementioned meanings and
Hal represents chlorine or bromine.

The compounds of the formula (XXVII) are new.

The compounds of the formula (XXX-B) are commercially available.

For example, the compounds of the formula (XXV)

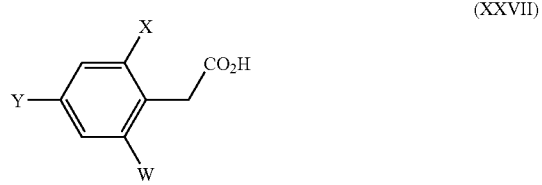
(XXVII)

in which
W, X and Y have the abovementioned meanings,
are obtained when phenylacetic esters of the formula (XXXI)

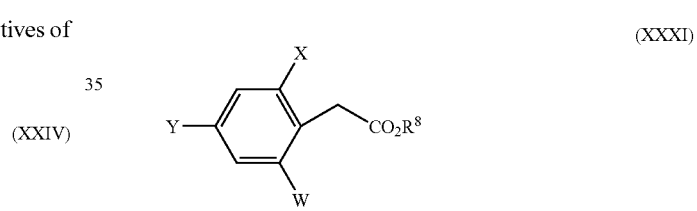
(XXXI)

in which
W, X Y and $R^8$ have the abovementioned meanings
are hydrolysed under generally known standard conditions in the presence of acids or bases, in the presence of a solvent.

Furthermore, phenylacetic acids of the formula (XXVII) are obtained in accordance with process (Q).

The compounds of the fonnula (XXXI) are new.

The compounds of the formula (XXXI)

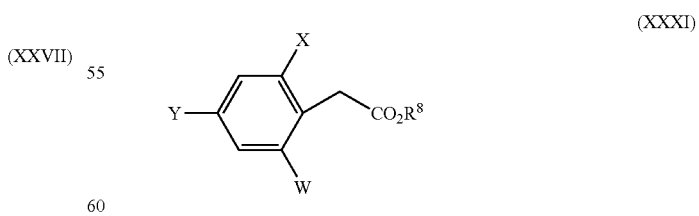
(XXXI)

in which
W, X, Y and $R^8$ have the abovementioned meanings
are obtained for example by process (R), which is described in the examples,
when phenylacetic esters of the formula (XXXI-a)

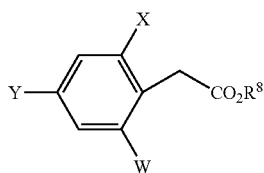
(XXXI-a)

in which
$R^8$, X and Y have the abovementioned meanings and
W represents halogen (in particular bromine)
are reacted in the presence of an alcohol, in the presence of a base and if appropriate in the presence of a catalyst (preferably copper salts such as, for example, copper(I) bromide).

The phenylacetic esters of the formula (XXXI-a) are known in principle from the application WO 96/35 664 and DE-A-10 301 804 and can be prepared by the methods described therein.

Moreover, phenylacetic esters of the formula (XXXI) are obtained by process (Q), which is described further below, by esterifying, by standard methods, the phenylacetic acids of the formula (XXVII) obtained in this process.

The compounds of the formula (IV)

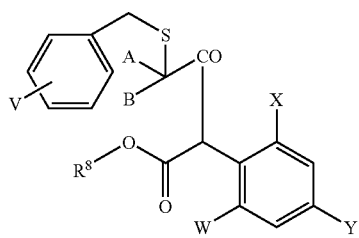
(IV)

in which
A, B, V, W, X, Y and $R^8$ have the abovementioned meanings and which are required as starting substances in the above process (C) are new.

They can be prepared by methods known in principle.

The compounds of the formula (IV) are obtained, for example, when substituted phenylacetic esters of the formula (XXXI)

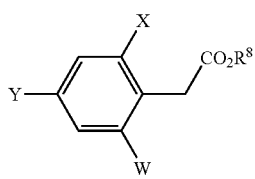
(XXXI)

in which
W, X, Y and $R^8$ have the abovementioned meanings
are acylated with 2-benzylthio-carboxylic halides of the formula (XXXII)

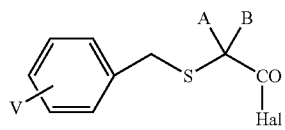
(XXXII)

in which
A, B and V have the abovementioned meanings and
Hal represents halogen (in particular chlorine or bromine)
in the presence of strong bases (see, for example, M. S. Chambers, E. J. Thomas, D. J. Williams, J. Chem. Soc. Chem. Commun., (1987), 1228).

Some of the benzylthio-carboxylic halides of the formula (XXXII) are known and/or can be prepared by known processes (J. Antibiotics (1983),26, 1589).

The halogenocarbonyl ketenes of the formula(VI) which are required as starting substances in the above processes (D), (E) and (H-α) are new. They can be prepared by methods known in principle (cf., for example, Org. Prep. Proced. Int. 7, (4), 155-158, 1975 and DE 1 945 703). Thus, for example, the compounds of the formula (VI)

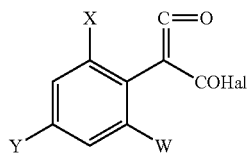
(VI)

in which
W, X and Y have the abovementioned meanings and
Hal represents chlorine or bromine
are obtained when
substituted phenylmalonic acids of the formula (XXXIII)

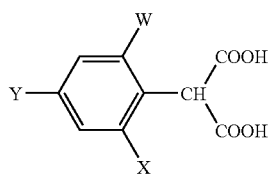
(XXXIII)

in which
W, X and Y have the abovementioned meanings
are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, dimethylformamide, methyl-sterylformamide or triphenylphosphine, and, if appropriate, in the presence of bases, such as, for example, pyridine or triethylamine.

The substituted phenylmalonic acids of the formula (XXXII) are new. They can be prepared in a simple manner by known processes (cf., for example, Organikum [Laboratory Practical in Organic Chemistry], VEB Deutscher Verlag der Wissenschaften, Berlin 1977, p. 517 et seq., EP-A-528 156, WO 96/35 664, WO 97/02 243, WO 97/01535, WO 97/36868 and WO 98/05638).

Thus, phenylmalonic acids of the formula (XXXIII)

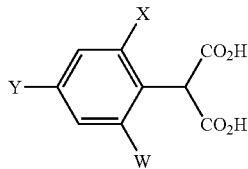
(XXXIII)

in which
W, X and Y have the abovementioned meanings are obtained when phenylmalonic esters of the formula (XI)

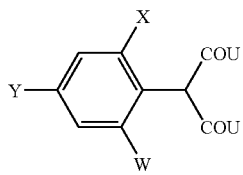
(XI)

in which
W, X and Y have the abovementioned meanings
and U represents OR$^8$ or NH$_2$,
where R$^8$ has the abovementioned meaning,
are initially hydrolysed in the presence of a base and a solvent and subsequently acidified carefully (EP-A-528 156, WO 96/35 664, WO 97/02 243).

The malonic esters of the formula (XI)

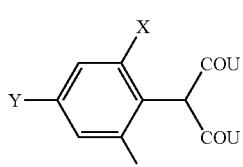
(XI)

in which
W, X and Y have the abovementioned meanings
and U represents OR$^8$ or NH$_2$,
where R$^8$ has the abovementioned meaning,
are new.

They can be synthesized by generally known methods of organic chemistry (cf., for example, Tetrahedron Lett. 27, 2763 (1986), Organikum VEB Deutscher Verlag der Wissenschaften, Berlin 1977, p. 587 et seq., WO 96/35664, WO 97/02243, WO 97/01535, WO 97/36868, WO 98/05638 and WO 99/47525).

The carbonyl compounds of the formula (V)

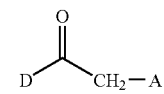
(V)

in which
A and D have the abovementioned meanings
or their silyl enol ethers of the formula (Va)

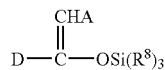
(Va)

in which
A, D and R$^8$ have the abovementioned meanings
and which are required as starting substances for process (D) according to the invention
are compounds which are commercially available, generally known or accessible by
known processes.

The preparation of the ketene acid chlorides of the formula (VI) which are required as starting substances for carrying out process (E) according to the invention have already been described above. The thioamides of the formula (VII)

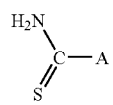
(VII)

in which
A has the abovementioned meaning
and which are required for carrying out process (E) according to the invention
are compounds generally known in organic chemistry.

The compounds of the formula (VIII)

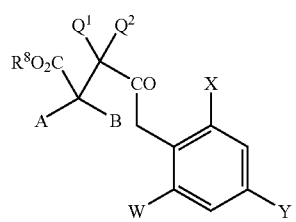
(VIII)

in which
A, B, Q$^1$, Q$^2$, W, X, Y and R$^8$ have the abovementioned meanings
and which are required as starting materials in the above process (F) are new.

They can be prepared by methods which are known in principle.

For example, the 5-aryl-4-ketocarboxylic esters of the formula (VIII) are obtained when 5-aryl-4-ketocarboxylic acids of the formula (XXXIV)

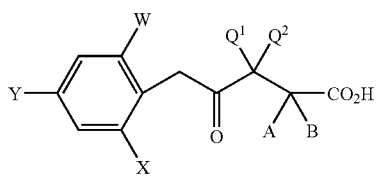
(XXXIV)

in which
W, X, Y, A, B, $Q^1$ and $Q^2$ have the abovementioned meanings
are esterified (cf., for example, Organikum, 15th edition, Berlin, 1977, page 499) or alkylated (see Preparation Example).

The 5-aryl-4-ketocarboxylic acids of the formula (XXXIV)

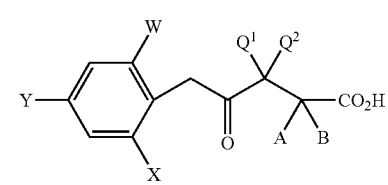
(XXXIV)

in which
A, B, $Q^1$, $Q^2$, W, X and Y have the abovementioned meanings
are new, but can be prepared by methods which are known in principle (WO 96/01 798, WO 97/14667, WO 98/39281).

For example, the 5-arylketocarboxylic acids of the formula (XXXIV) are obtained when 2-phenyl-3-oxoadipic esters of the formula (XXXV)

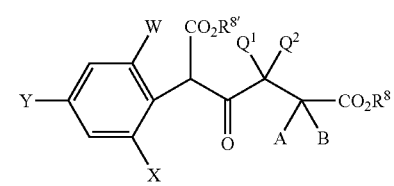
(XXXV)

in which
A, B, $Q^1$, $Q^2$, W, X and Y have the abovementioned meanings and
$R^8$ and $R^{8'}$ represent alkyl (in particular $C_1$-$C_8$-alkyl) and,
when the compound of the formula (XXXVII-a) is employed, $R^8$ represents hydrogen,
are decarboxylated, if appropriate in the presence of a diluent and if appropriate in the presence of a base or acid (cf., for example, Organikum, 15th edition, Berlin, 1977, pages 519 to 521).

The compounds of the formula (XXXV)

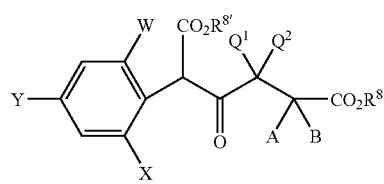
(XXXV)

in which
A, B, $Q^1$, $Q^2$, W, X, Y, $R^8$, $R^{8'}$ have the abovementioned meanings and,
when the compound of the formula (XXXVII-a) is employed, $R^8$ represents hydrogen
are new.

The compounds of the formula (XXXXV) are obtained, for example,
when dicarboxylic semiester chlorides of the formula (XXXVI)

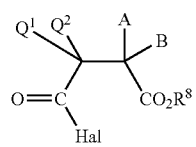
(XXXVI)

in which
A, B, $Q^1$, $Q^2$ and $R^8$ have the abovementioned meanings and
Hal represents chlorine or bromine
or carboxylic anhydrides of the formula (XXXVII-a)

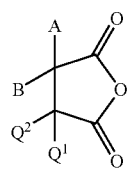
(XXXVII-a)

in which
A, B, $Q^1$ and $Q^2$ have the abovementioned meanings
are acylated with a phenylacetic ester of the formula (XXXI)

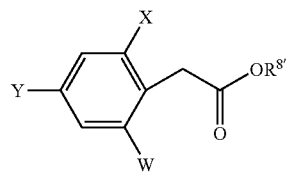
(XXXI)

in which
W, X, Y and $R^{8'}$ have the abovementioned meanings
in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XXXVI) and (XXXVII-a) are known compounds of organic chemistry; alternatively, they can be prepared in a simple manner by methods which are known in principle.

The compounds of the formula (IX)

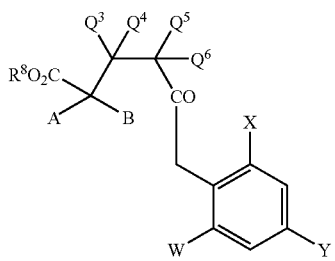

(IX)

in which
A, B, $Q^3$, $Q^4$, $Q^5$, $Q^6$, W, X, Y and $R^8$ have the abovementioned meanings
and which are required as starting materials in the above process (G)
are new.

They can be prepared by methods which are known in principle.

For example, the 6-aryl-5-ketocarboxylic esters of the formula (IX) are obtained when 6-aryl-5-ketocarboxylic acids of the formula (XXXVIII)

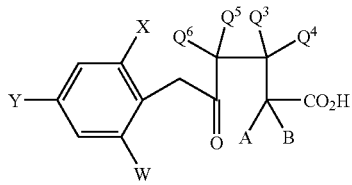

(XXXVIII)

in which
A, B, $Q^3$, $Q^4$, $Q^5$, $Q^6$, W, X and Y have the abovementioned meanings
are esterified (cf, for example, Organikum, 15th edition, Berlin, 1977, page 499).

The 6-aryl-5-ketocarboxylic acids of the formula (XXXVIII)

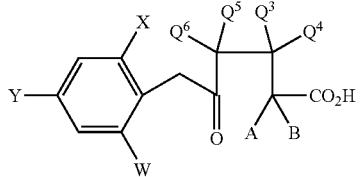

(XXXVIII)

in which
A, B, $Q^3$, $Q^4$, $Q^5$, $Q^6$, W, X and Y have the abovementioned meanings
are new. They can be prepared by methods which are known in principle (WO 99/43649, WO 99/48869), for example when substituted 2-phenyl-3-oxoheptanedioic esters of the formula (XXXIX)

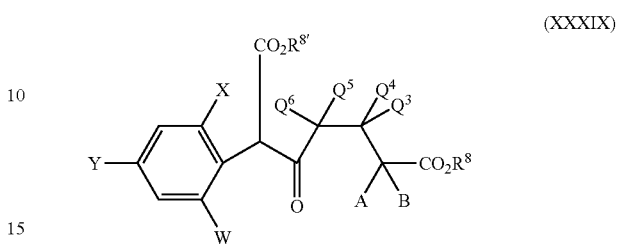

(XXXIX)

in which
A, B, $Q^3$, $Q^4$, $Q^5$, $Q^6$, W, X and Y have the abovementioned meanings and
$R^8$ and $R^{8'}$ represent alkyl (preferably $C_1$-$C_6$-alkyl), and,
when the compound of the formula (XXXVII-b) is employed, $R^8$ represents hydrogen,
are hydrolysed and decarboxylated, if appropriate in the presence of a diluent and if appropriate in the presence of a base or acid (cf., for example, Organikum, 15th edition, Berlin, 1977, pages 519 to 521).

The compounds of the formula (XXXIX)

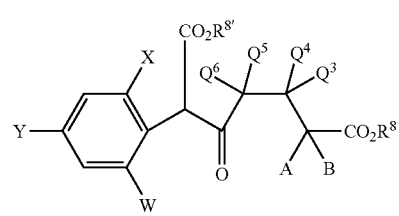

(XXXIX)

in which
A, B, $Q^3$, $Q^4$, $Q^5$, $Q^6$, W, X, Y, $R^8$ and $R^{8'}$ have the abovementioned meanings
are new and can be obtained
when dicarboxylic esters of the formula (XL)

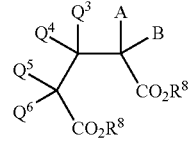

(XL)

in which
A, B, $Q^3$, $Q^4$, $Q^5$, $Q^6$ and $R^8$ have the abovementioned meanings
or carboxylic anhydrides of the formula (XXXVII-b)

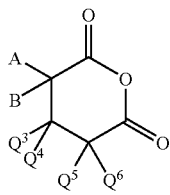

(XXXVII-b)

in which
A, B, $Q^3$, $Q^4$, $Q^5$, $Q^6$ have the abovementioned meanings
are subjected to a condensation reaction with a substituted phenylacetic ester of the formula (XXXI)

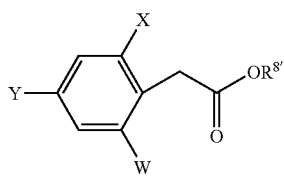

(XXXI)

in which
W, X, Y and $R^{8'}$ have the abovementioned meanings
in the presence of a diluent and in the presence of a base.

Some of the compounds of the formula (XL) are known; alternatively, they can be synthesized by known processes.

Some of the hydrazines of the formula (X)

(X)

in which
A and D have the abovementioned meanings
and which are required as starting materials for processes (H-α) and (H-β) according to the invention are known; alternatively, they can be prepared by methods known from the literature (cf., for example, Liebigs Ann. Chem. 585, 6 (1954); Reaktionen der organischen Synthese [Reactions in organic synthesis], C. Ferri, pages 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds of the formula (XII)

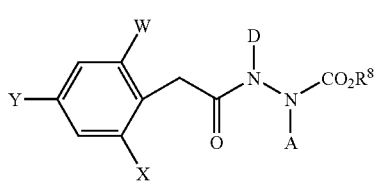

(XII)

in which
A, D, W, X, Y and $R^8$ have the abovementioned meanings
and which are required for process (H-γ) according to the invention are new.

The acylcarbazates of the formula (XII) are obtained for example when carbazates of the formula (XLI)

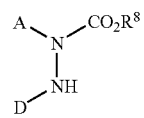

(XLI)

in which
A, $R^8$ and D have the abovementioned meanings
are acylated with substituted phenylacetic acid derivatives of the formula (XXIV)

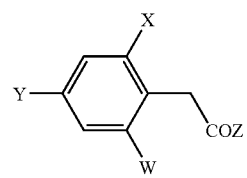

(XXIV)

in which
W, X, Y and Z have the abovementioned meanings
(Chem. Reviews 52, 237-416 (1953); Bhattacharya, Indian J. Chem. 6, 341-5, 1968).

Some of the carbazates of the formula (XLI) are commercially available compounds, others are known compounds, or they can be prepared by methods of organic chemistry which are known in principle.

The compounds of the formula (XXIV) have already been described in context with the precursors for processes (A) and (B). (Q) Moreover, phenylacetic acids of the formula (XXVII)

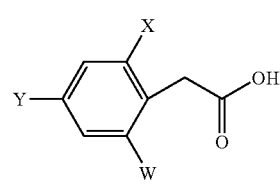

(XXVII)

in which
W, X and Y have the abovementioned meanings
are obtained when phenylacetaldehydes of the formula (XL)

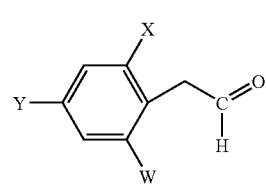

(XLII)

in which
W, X and Y have the abovementioned meanings
are oxidized with suitable oxidants (such as, for example, NaOCl), if appropriate in the presence of a solvent.

The compounds of the formula (XLII) are new.

Compounds of the formula (XLII)

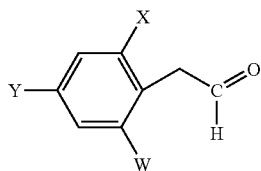

(XLII)

in which
W, X and Y have the abovementioned meanings
are obtained when 3-phenylpropenes of the formula (XLIII)

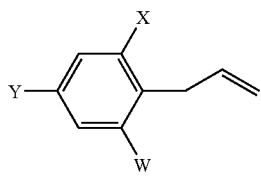

(XLIII)

in which
W, X and Y have the abovementioned meanings
are subjected to ozonolysis in the presence of a solvent and the resulting ozonide is subjected to reductive work-up, for example using dimethyl sulphide.

The 2-alkoxy-substituted 3-phenylpropenes of the formula (XLIII) which are required for the preparation of the compounds of the formula (XLII) are compounds of organic chemistry which are known in principle and which can be prepared by standard methods by alkylating phenols with allyl halides, followed by Claisen rearrangement and subsequent alkylation (WO 96/25 395).

The acid halides of the formula (XIII), carboxylic anhydrides of the formula (XIV), chloroformic esters or chloroformic thioesters of the formula (XV), chloromonothioformic esters or chlorodithioformic esters of the formula (XVI), sulphonyl chlorides of the formula (XVII), phosphorus compounds of the formula (XVIII), metal hydroxides, metal alkoxides or amines of the formulae (XIX) and (XX), isocyanates of the formula (XXI) and carbamoyl chlorides of the formula (XXII) which are furthermore required as starting substances for carrying out processes (I), (J), (K), (L), (M), (N) and (O) according to the invention are generally known compounds of organic or inorganic chemistry.

The compounds of the formulae (V), (VII), (XIII) to (XXII), (XXIII), (XXVI), (XXVIII), (XXX-A), (XXX-B), (XXXII), (XXXVI), (XXXVII-a), (XXXVII-b), (XL) and (XLI) have futhermore been disclosed in the patent applications cited at the outset and/or can be prepared by the methods given therein.

Process (A) is characterized in that compounds of the formula (II) in which A, B, D, W, X, Y and $R^8$ have the abovementioned meanings are subjected to an intramolecular condensation in the presence of a base.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and also alcohols, such as methanol, ethanol, propanol, isopropanol, butanol, iso-butanol and tert-butanol.

Bases (deprotonating agents) which can be employed when carrying out process (A) according to the invention are all customary proton acceptors. The following can preferably be used: oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). Alkali metals, such as sodium or potassium, can furthermore be used. Other substances which can be employed are amides and hydrides of alkali metals and alkaline earth metals, such as sodium amide, sodium hydride and calcium hydride, and furthermore also alkali metal alcoholates, such as sodium methoxide, sodium ethoxide and potassium tert-butoxide.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formula (II) and the deprotonating bases are generally employed in approximately twice the equimolar amounts. However, it is also possible to use one or the other component in a larger excess (up to 3 mol).

Process (B) is characterized in that compounds of the formula (III) in which A, B, W, X, Y and $R^8$ have the abovementioned meanings are subjected to an intramolecular condensation in the presence of a diluent and in the presence of a base.

Diluents which can be employed in process (B) according to the invention are all inert organic solvents. The following can preferably be used: hydrocarbons, such as toluene and xylene, furthermore ethers, such as dibutyl ether, tetrahydrofiran, dioxane, glycol dimethyl ether and diglycol dimethyl ether, furthermore polar solvents, such as dimethyl sulphoxide, sulpholane, dimethylformamide and N-methyl-pyrrolidone. Other substances which can be employed are alcohols, such as methanol, ethanol, propanol, iso-propanol, butanol, iso-butanol and tert-butanol.

Bases (deprotonating agents) which can be employed when carrying out process (B) according to the invention are all customary proton acceptors. The following can preferably be used: oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). Alkali metals, such as sodium or potassium, can furthermore be used. Other substances which can be employed are amides and hydrides of alkali metals and alkaline earth metals, such as sodium amide, sodium hydride and calcium hydride, and furthermore also alkali metal alcoholates, such as sodium methoxide, sodium ethoxide and potassium tert-butoxide.

When carrying out process (B) according to the invention, the reaction temperatures can be varied within a substantial range. In general, the process is carried out at temperatures between 0° C. and 250° C., preferably between 50° C. and 150° C.

Process (B) according to the invention is generally carried out under atmospheric pressure.

When carrying out process (B) according to the invention, the reactants of the formula (III) and the deprotonating bases are generally employed in approximately equimolar amounts. However, it is also possible to use one or the other component in a larger excess (up to 3 mol).

Process (C) is characterized in that compounds of the formula (IV) in which A, B,V, W, X, Y and $R^8$ have the abovementioned meanings are subjected to an intramolecular cyclization in the presence of an acid and, if appropriate, in the presence of a diluent.

Diluents which can be employed in process (C) according to the invention are all inert organic solvents. The following can preferably be used: hydrocarbons, such as toluene and xylene, fturthermore halogenated hydrocarbons, such as dichloromethane, chloroform, ethylene chloride, chlorobenzene, dichlorobenzene, moreover polar solvents, such as dimethyl sulphoxide, sulpholane, dirnethylformamide and N-methyl-pyrrolidone. Other substances which can be employed are alcohols, such as methanol, ethanol, propanol, iso-propanol, butanol, isobutanol or tert-butanol.

If appropriate, the acid employed may also act as the diluent.

Acids which can be employed in process (C) according to the invention are all customary inorganic and organic acids, such as, for example, hydrohalic acids, sulphuric acid, alkyl-, aryl-and haloalkylsulphonic acids, in particular halogenated alkylcarboxylic acids, such as, for example, trifluoroacetic acid.

When carrying out process (C) according to the invention, the reaction temperatures can be varied within a substantial range. In general, the process is carried out at temperatures between 0° C. and 250° C., preferably between 50° C. and 150° C.

Process (C) according to the invention is generally carried out under atmospheric pressure.

When carrying out process (C) according to the invention, the reactants of the formula (IV) and the acid are employed, for example, in equimolar amounts. If appropriate, however, it is also possible to use the acid as the solvent and the catalyst.

Process (D) according to the invention is characterized in that carbonyl compounds of the formula (V) or their enol ethers of the formula (V-a) are reacted with ketene acid halides of the formula (VI), in the presence of a diluent and if appropriate in the presence of an acid acceptor.

Diluents which can be employed in process (D) according to the invention are all inert organic solvents. The following can preferably be used: optionally halogenated hydrocarbons, such as toluene, xylene, mesitylene, chlorobenzene and dichlorobenzene, furthermore ethers, such as dibutyl ether, glycol dimethyl ether, diglycol dimethyl ether and diphenyl ether, furthermore polar solvents, such as dimethyl sulphoxide, sulpholane, dimethylformamide or N-methyl-pyrrolidone.

Acid acceptors which can be used for carrying out the process variant (D) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline.

When carrying out process variant (D) according to the invention, the reaction temperatures can be varied within a substantial range. The process is expediently carried out at temperatures between 0° C. and 250° C., preferably between 50° C. and 220° C.

Process (D) according to the invention is expediently carried out under atmospheric pressure.

When carrying out process (D) according to the invention, the reactants of the formulae (V) and (VI) in which A, D, W, X and Y have the abovementioned meanings and Hal represents halogen and, if appropriate, the acid acceptors are generally employed in approximately equimolar amounts. However, it is also possible to use one or another component in a larger excess (up to 5 mol).

Process (E) according to the invention is characterized in that thioamides of the formula (VII) are reacted with ketene acid halides of the formula (VI), in the presence of a diluent and if appropriate in the presence of an acid acceptor.

Diluents which can be employed in process variant (E) according to the invention are all inert organic solvents. The following can preferably be used: hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Acid acceptors which can be used for carrying out process (E) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline.

When carrying out process (E) according to the invention, the reaction temperatures can be varied within a substantial range. The process is expediently carried out at temperatures between 0° C. and 250° C., preferably between 20° C. and 220° C.

Process (E) according to the invention is expediently carried out under atmospheric pressure.

When carrying out process (E) according to the invention, the reactants of the formulae (VII) and (VI) in which A, W, X and Y have the abovementioned meanings and Hal represents halogen, and, if appropriate, the acid acceptors, are generally employed in approximately equimolar amounts. However, it is also possible to use one or the other component in a larger excess (up to 5 mol).

Process (F) is characterized in that compounds of the formula (VIII) in which A, B, $Q^1$, $Q^2$, W, X, Y and $R^8$ have the abovementioned meanings are subjected to an intramolecular condensation reaction in the presence of a base.

Diluents which can be employed in process (F) according to the invention are all organic solvents which are inert towards the reactants. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methylpyrrolidone. Alcohols such as methanol, ethanol, propanol, isopropanol, butanol, isobutanol, tert-butanol can also be employed.

Bases (deprotonating agents) which can be employed when carrying out process (F) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, Adogen 464 (methyltrialkyl($C_8$-$C_{10}$)ammonium chloride) or TDA 1 (tris (methoxyethoxyethyl)-amine). Alkali metals such as sodium or potassium may also be employed. Others which can be employed are amides and hydrides of alkali metals and alkaline earth metals, such as sodium amide, sodium hydride and calcium hydride, and furthermore also alkali metal alcoholates such as sodium methoxide, sodium ethoxide and potassium tert-butoxide.

When carrying out process (F) according to the invention, the reaction temperatures can be varied within a substantial range. The process is generally carried out at temperatures between −75° C. and 250° C., preferably between −50° C. and 150° C.

Process (F) according to the invention is generally carried out under atmospheric pressure.

When carrying out process (F) according to the invention, the reactants of the formula (VIII) and the deprotonating bases are generally employed in approximately equimolar amounts. However, it is also possible to use one or the other component in a larger excess (up to 3 mol).

Process (G) is characterized in that compounds of the formula (IX) in which A, B, $Q^3$, $Q^4$, $Q^5$, $Q^6$, W, X, Y and $R^8$ have the abovementioned meanings are subjected to an intramolecular condensation reaction in the presence of bases.

Diluents which can be employed in process (G) according to the invention are all organic solvents which are inert towards the reactants. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methylpyrrolidone. Alcohols such as methanol, ethanol, propanol, iso-propanol, butanol, iso-butanol, tert-butanol can also be employed.

Bases (deprotonating agents) which can be employed when carrying out process (G) according to the invention are all customary proton acceptors.

The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, Adogen 464 (methyltrialkyl($C_8$-$C_{10}$)ammonium chloride) or TDA 1 (tris(methoxy-ethoxyethyl) amine). Alkali metals such as sodium or potassium may also be employed. Others which can be employed are amides and hydrides of alkali metals and alkaline earth metals, such as sodium amide, sodium hydride and calcium hydride, and furthermore also alkali metal alcoholates such as sodium methoxide, sodium ethoxide and potassium tert-butoxide.

When carrying out process (G) according to the invention, the reaction temperatures can be varied within a substantial range. The process is generally carried out at temperatures between 0° C. and 250° C., preferably between 50° C. and 150° C.

Process (G) according to the invention is generally carried out under atmospheric pressure.

When carrying out process (G) according to the invention, the reactants of the formula (IX) and the deprotonating bases are generally employed in approximately equimolar amounts. However, it is also possible to use one or the other component in a larger excess (up to 3 mol).

Process H-α) according to the invention is characterized in that hydrazines of the formula (X) or salts of these compounds are reacted with ketene acid halides of the formula (VI) in the presence of a diluent and if appropriate in the presence of an acid acceptor.

Diluents which can be employed in process H-α) according to the invention are all inert organic solvents. The following can preferably be used: optionally chlorinated hydrocarbons such as, for example, mesitylene, chlorobenzene and dichlorobenzene, toluene, xylene, furthermore ethers such as dibutyl ether, glycol dimethyl ether, diglycol dimethyl ether and diphenylethane, moreover polar solvents such as dimethyl sulphoxide, sulpholane, dimethylformamide or N-methylpyrrolidone.

Acid acceptors which can be used for carrying out process variant H-α) according to the invention are all customary acid acceptors.

The following can preferably be used: tertiary amines such as triethylamine, pyridine, diazabicyclooctane (DABCO), diazabicycloundecane (DBU), diazabicyclononene (DBN), Hünig base and N,N-dimethylaniline.

When carrying out the process variant H-α) according to the invention, the reaction temperatures can be varied within a substantial range. The process is expediently carried out at temperatures between 0° C. and 250° C., preferably between 50° C. and 220° C.

Process H-α) according to the invention is expediently carried out under atmospheric pressure.

When carrying out process H-α) according to the invention, the reactants of the formulae (VI) and (X) in which A, D, W, X and Y have the abovementioned meanings and Hal represents halogen, and, if appropriate, the acid acceptors, are generally employed in approximately equimolar amounts. However, it is also possible to use one or the other component in a larger excess (up to 5 mol).

Process (H-β) is characterized in that hydrazines of the formula (X) or salts of this compound in which A and D have the abovementioned meanings are subjected to a condensation reaction with malonic esters or malonamides of the formula (XI) in which U, W, X, Y and $R^8$ have the abovementioned meanings in the presence of a base.

Diluents which can be employed in process (H-β) according to the invention are all inert organic solvents. The following can preferably be used: optionally halogenated hydrocarbons such as toluene, xylene, mesitylene, chlorobenzene and dichlorobenzene, furthermore ethers such as dibutyl ether, tetrahydrofuran, dioxane, diphenyl ether, glycol dimethyl ether and diglycol dimethyl ether, moreover polar solvents such as dimethyl sulphoxide, sulpholane, dimethylformamide, dimethylacetamide and N-methyl-pyrrolidone, and alcohols such as methanol, ethanol, propanol, iso-propanol, butanol, iso-butanol and tert-butanol.

Bases (deprotonating agents) which can be employed when carrying out process (H-β) according to the invention are all customary proton acceptors. The following can preferably be used: oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts such as, for example, tri-ethylbenzylammonium chloride, tetrabutylammonium bromide, Adogen 464 (=methyl-trialkyl($C_8$-$C_{10}$)ammonium chloride) or TDA 1 (=tris(methoxyethoxyethyl)amine). Others which can be used are alkali metals such as sodium or potassium. Amides and hydrides of alkali metals and alkaline earth metals, such as sodium amide, sodium hydride and calcium hydride, and moreover also alkali metal alcoholates, such as sodium methoxide, sodium ethoxide and potassium tert-butoxide, can also be employed.

Others which can be employed are tertiary amines such as triethylamine, pyridine, diazabicyclooctane (DABCO), diazabicycloundecane (DBU), diazabicyclononene (DBN), Hünig base and N,N-dimethylaniline.

When carrying out process (H-β) according to the invention, the reaction temperatures can be varied within a substantial range. In general, the process is carried out at temperatures between 0° C. and 280° C., preferably between 50° C. and 180° C.

Process (H-β) according to the invention is generally carried out under atmospheric pressure.

When carrying out process (H-β) according to the invention, the reactants of the formulae (XI) and (X) are generally employed in approximately equimolar amounts. However, it is also possible to use one or the other component in a larger excess (up to 3 mol).

Process (H-γ) is characterized in that compounds of the formula (XII) in which A, D, W, X, Y and $R^8$ have the abovementioned meanings are subjected to an intramolecular condensation reaction in the presence of a base.

Diluents which can be employed in process (H-γ) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methylpyrrolidone, and alcohols such as methanol, ethanol, propanol, iso-propanol, butanol, iso-butanol and tert-butanol.

Bases (deprotonating agents) which can be employed when carrying out process (H-γ) according to the invention are all customary proton acceptors. The following can preferably be used: oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, Adogen 464 (=methyl-trialkyl($C_8$-$C_{10}$)ammonium chloride) or TDA 1 (=tris(methoxyethoxyethyl)amine). Others which can be used are alkali metals such as sodium or potassium. Amides and hydrides of alkali metals and alkaline earth metals, such as sodium amide, sodium hydride and calcium hydride, and moreover also alkali metal alcoholates, such as sodium methoxide, sodium ethoxide and potassium tert-butoxide, can also be employed.

When carrying out process (H-γ) according to the invention, the reaction temperatures can be varied within a substantial range. In general, the process is carried out at temperatures between 0° C. and 250° C., preferably between 50° C. and 150° C.

Process (H-γ) according to the invention is generally carried out under atmospheric pressure.

When carrying out process (H-γ) according to the invention, the reactants of the formula (XII) and the deprotonating bases are generally employed in approximately twice the molar amounts. However, it is also possible to employ one or the other component in a larger excess (up to 3 mol).

Process (I-α) is characterized in that compounds of the formulae (I-1-a) to (I-8-a) are reacted in each case with carboxylic acid halides of the formula (XIII), if appropriate in the presence of a diluent and if appropriate in the presence of an acid-binding agent.

Diluents which can be employed in process (I-α) according to the invention are all solvents which are inert to the acid halides. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents, such as dimethyl sulphoxide and sulpholane. If the acid halide is sufficiently stable to hydrolysis, the reaction can also be carried out in the presence of water. Suitable acid-binding agents in the reaction in accordance with process (I-α) according to the invention are all customary acid acceptors. The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperatures in process (I-α) according to the invention can be varied within a substantial range. In general, the process is carried out at temperatures between −20° C. and +150° C., preferably between 0° C. and 100° C.

When carrying out process (I-α) according to the invention, the starting substances of the formulae (I-1-a) to (I-8-a) and the carboxylic acid halide of the formula (XIII) are generally used in approximately equivalent amounts in each case. However, it is also possible to employ the carboxylic acid halide in a larger excess (up to 5 mol). Working-up is carried out by customary methods.

Process (I-β) is characterized in that compounds of the formulae (1-1-a) to (1-8-a) are reacted with carboxylic anhydrides of the formula (XIV), if appropriate in the presence of a diluent and if appropriate in the presence of an acid-binding agent.

Diluents which can preferably be used in process (I-β) according to the invention are those which are also preferably suitable when using acid halides. Besides, a carboxylic anhydride employed in excess may also simultaneously act as the diluent.

Optionally added acid-binding agents in process (I-β) are preferably those acid-binding agents which are also preferably suitable when using acid halides.

The reaction temperatures in process (I-β) according to the invention can be varied within a substantial range. In general, the process is carried out at temperatures between −20° C. and +150° C., preferably between 0° C. and 100° C.

When carrying out process (I-β) according to the invention, the starting substances of the formulae (I-1-a) to (1-8-a) and the carboxylic anhydride of the formula (XIV) are generally employed in each case in approximately equivalent amounts. However, it is also possible to employ the carboxylic anhydride in a larger excess (up to 5 mol). Working-up is carried out by customary methods.

In general, a procedure is followed in which diluent and carboxylic anhydride which is present in excess and the carboxylic acid which forms are removed by distillation or by washing with an organic solvent or with water.

Process (J) is characterized in that compounds of the formulae (I-1-a) to (I-8-a) are reacted in each case with chloroformic esters or chloroformic thioesters of the formula (XV), if appropriate in the presence of a diluent and if appropriate in the presence of an acid-binding agent.

Suitable acid-binding agents for the reaction in accordance with process (J) according to the invention are all customary acid acceptors. The following can preferably be used: tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Diluents which can be employed in process (J) according to the invention are all solvents which are inert to the chloroformic esters or chloroformic thioesters. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out process (J) according to the invention, the reaction temperatures can be varied within a substantial range. If the process is carried out in the presence of a diluent and of an acid-binding agent, the reaction temperatures are generally between −20° C. and +100° C., preferably between 0° C. and 50° C.

Process (J) according to the invention is generally carried out under atmospheric pressure.

When carrying out process (J) according to the invention, the starting substances of the formulae (I-1-a) to (I-8-a) and the respective chloroformic ester or chloroformic thioester of the formula (XM) are generally used in in each case approximately equivalent amounts. However, it is also possible to employ one or the other component in a larger excess (up to 2 mol). Working-up is carried out by customary methods. In general, a procedure is followed in which salts which have precipitated are removed and the reaction mixture which remains is concentrated by stripping off the diluent.

Process (K) according to the invention is characterized in that compounds of the formulae (I-1-a) to (I-8-a) are reacted in each case with compounds of the formula (XVI) in the presence of a diluent and, if appropriate, in the presence of an acid-binding agent.

In preparation process (K), approximately 1 mol of chloromonothioformic ester or chlorodithioformic ester of the formula (XVI) is reacted per mole of starting compound of the formulae (I-1-a) to (I-8-a) at 0 to 120° C., preferably at 20 to 60° C.

Suitable diluents which are optionally added are all inert polar organic solvents, such as ethers, amides, sulphones, sulphoxides, but also halogenoalkanes.

Dimethyl sulphoxide, tetrahydrofuran, dimethylformamide or methylene chloride are preferably employed.

If, in a preferred embodiment, the enolate salt of the compounds (I-1-a) to (I-8-a) is prepared by adding strong deprotonating agents, such as, for example, sodium hydride or potassium tertiary-butoxide, the further addition of acid-binding agents can be dispensed with.

If acid-binding agents are employed, then suitable substances are customary inorganic or organic bases, examples which may be mentioned being sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods.

Process (L) according to the invention is characterized in that compounds of the formulae (I-1-a) to (I-8-a) are reacted in each case with sulphonyl chlorides of the formula (XVI), if appropriate in the presence of a diluent and if appropriate in the presence of an acid-binding agent.

In preparation process (L), approximately 1 mol of sulphonyl chloride of the formula (XVII) is reacted per mole of starting compound of the formulae (I-1-a) to (I-8-a) at −20 to 150° C., preferably at 20 to 70° C.

Suitable diluents which are optionally added are all inert polar organic solvents, such as ethers, amides, nitriles, sulphones, sulphoxides, or halogenated hydrocarbons, such as methylene chloride.

Dimethyl sulphoxide, tetrahydrofuran, dimethylformamide or methylene chloride are preferably employed.

If, in a preferred embodiment, the enolate salt of the compounds (I-1-a) to (I-8-a) is prepared by adding strong deprotonating agents (such as, for example, sodium hydride or potassium tertiary-butoxide), the further addition of acid-binding agents can be dispensed with.

If acid-binding agents are employed, then suitable substances are customary inorganic or organic bases, examples which may be mentioned being sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods.

Process (M) according to the invention is characterized in that compounds of the formulae (I-1-a) to (I-8-a) are reacted in each case with phosphorus compounds of the formula (XVII), if appropriate in the presence of a diluent and if appropriate in the presence of an acid-binding agent.

In preparation process (M), 1 to 2, preferably 1 to 1.3, mol of the phosphorus compound of the formula (XVII) are reacted per mole of the compounds (I-1-a) to (I-8-a) at temperatures between −40° C. and 150° C., preferably between −10 and 110° C., to obtain compounds of the formulae (I-1-e) to (I-8-e).

Suitable diluents which are optionally added are all inert, polar organic solvents, such as ethers, amides, nitriles, alcohols, sulphides, sulphones, sulphoxides and the like.

Acetonitrile, dimethyl sulphoxide, tetrahydrofuran, dimethylformamide or methylene chloride are preferably employed.

Suitable acid-binding agents which are optionally added are customary inorganic or organic bases, such as hydroxides, carbonates or amines. Examples which may be mentioned are sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods of organic chemistry. The end products obtained are preferably purified by crystallization, chromatography or by so-called "incipient distillation", i.e. removal of the volatile components in vacuo.

Process (N) is characterized in that compounds of the formulae (I-1-a) to (I-8-a) are reacted with metal hydroxides or metal alkoxides of the formula (XIX) or amines of the formula (XX), if appropriate in the presence of a diluent.

Diluents which can be employed in process (N) according to the invention are, preferably, ethers, such as tetrahydrofuran, dioxane, diethyl ether, or else alcohols, such as methanol, ethanol, isopropanol, but also water.

Process (N) according to the invention is generally carried out under atmospheric pressure.

The reaction temperatures are generally between −20° C. and 100° C., preferably between 0° C. and 50° C.

Process (O) according to the invention is characterized in that compounds of the formulae (I-1-a) to (I-8-a) are reacted in each case with (O-α) compounds of the formula (XXI), if appropriate in the presence of a diluent and if appropriate in the presence of a catalyst, or (O-β) with compounds of the formula (XXII), if appropriate in the presence of a diluent and if appropriate in the presence of an acid-binding agent.

In preparation process (O-α), approximately 1 mol of isocyanate of the formula (XXI) is reacted per mole of starting compound of the formulae (I-1-a) to (I-8-a) at 0 to 100° C., preferably at 20 to 50° C.

Suitable diluents which are optionally added are all inert organic solvents, such as ethers, amides, nitriles, sulphones or sulphoxides.

If appropriate, catalysts may be added to accelerate the reaction. Catalysts which can be employed very advantageously are organotin compounds, such as, for example, dibutyltin dilaurate. The process is preferably carried out under atmospheric pressure.

In preparation process (O-β), approximately 1 mol of carbamoyl chloride of the formula (XXII) is reacted per mole of starting compound of the formulae (I-1-a) to (I-8-a) at −20 to 150° C., preferably at 0 to 70° C.

The diluents which are optionally added are all inert polar organic solvents, such as ethers, amides, sulphones, sulphoxides or halogenated hydrocarbons.

Dimethyl sulphoxide, tetrahydrofuran, dimethylformamide or methylene chloride are preferably employed.

If, in a preferred embodiment, the enolate salt of the compound (I-1-a) to (I-8-a) is prepared by adding strong deprotonating agents (such as, for example, sodium hydride or potassium tertiary-butoxide), the further addition of acid-binding agents can be dispensed with.

If acid-binding agents are employed, then suitable substances are customary inorganic or organic bases, examples which may be mentioned being sodium hydroxide, sodium carbonate, potassium carbonate, triethylamine or pyridine.

The reaction can be carried out under atmospheric pressure or under elevated pressure, it is preferably carried out under atrmospheric pressure. Working-up is carried out by customary methods.

Process (P) is characterized in that compounds of the formulae (I-1-a') to (I-8-a') in which A, B, D, $Q^1$, $Q^2$, $Q^3$, $Q^4$, $Q^5$, $Q^6$, X and Y have the abovementioned meanings and W' preferably represents bromine are reacted with alcohols of the formula WOH in which W has the abovementioned meaning, in the presence of a base and of a Cu(I) salt (for example CuBr or CuI).

Diluents which can be employed in process (P) according to the invention are all organic solvents which are inert to the reactants. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide, dimethylacetamide and N-methylpyrrolidone, esters such as methyl acetate, ethyl acetate, propyl acetate, and alcohols of the formula WOH such as, for example, methanol, ethanol, propanol, iso-propanol, butanol and iso-butanol.

Bases (deprotonating agents) which can be employed for carrying out process (P) according to the invention are all customary proton acceptors. Alkali metals such as sodium or potassium can preferably be used. Others which can be employed are amides and hydrides of alkali metals and alkaline earth metals, such as sodium amide, sodium hydride and calcium hydride, and preferably also alkali metal alcoholates such as sodium methoxide, sodium ethoxide, sodium isopropoxide, sodium tert-butoxide and potassium tert-butoxide.

When carrying out process (P) according to the invention, the reaction temperature can be varied within a substantial range. In general, the process is carried out at temperatures between 0° C. and 250° C., preferably between 50° C. and 150° C.

Process (P) according to the invention is generally carried out under atmospheric pressure.

When carrying out process (P) according to the invention, the reactants of the formulae (I-1-a') to (I-8-a') are generally reacted with an excess of the alcohols WOH and of the bases of up to 20 mol, preferably 3 to 5 mol. As a rule, the copper(I) salts are employed in catalytic amounts of 0.001 to 0.5 mol, preferably 0.01 to 0.2 mol. However, they may also be employed in equimolar amounts.

The active compounds are well tolerated by plants, have advantageous toxicity to warm-blooded species and are environmentally friendly, they can be employed for protecting plants and plant organs, for increasing yields, improving crop quality and for controlling animal pests, in particular insects, arachnids and nematodes found in agriculture, forests, gardens and leisure grounds, in the protection of stored products and materials and in the hygiene sector. They can be used with preference to protect plants. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculate.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp.,

*Locusta migratoria* migratorioides, *Melanoplus* spp. and *Schistocerca gregaria.*

From the order of the Blattaria, for example, *Blatta orientalis, Periplaneta americana, Leucophaea maderae* and *Blattella germanica*

From the order of the Dennaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis*

*fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla spp.*

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusiani, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coteoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorphoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus, Latrodectus mactans, Acarus siro, Argas* spp., *Ornithodoros* spp., *Dermanyssus gallinae, Eriophyes ribis, Phyllocoptrta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds according to the invention may also be used in certain concentrations or application rates to act as herbicides and microbicides, for example as fungicides, antimycotics and bactericides. If appropriate, they can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on or injection and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as components in the mixtures are, for example, the following:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris (albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; pro-cymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrroinitrin; quinconazole; quinoxyfen; quintozene; simeconazole; spiroxanine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2[(methylsulphonyl)amino]-butanamide; 1-(1-naphthalenyl)-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decan-3-amine; sodium tetrathiocarbonate;

and copper salts and preparations such as Bordeaux mixture; copper hydroxide; copper naphthenate; copper oxychloride; copper sulfate; cufraneb; cuprous oxide; mancopper; oxmecopper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetainiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin S-cyclopentyl isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusate-sodium, dofenapyn, DOWCO-439, eflusilanate, emamectin, emamectin benzoate, empenthrin (1R isomer), endosulfan, Entomophthora spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, Metarhizium anisopliae, Metarhizium flavoviride, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, Paecilomyces fumosoroseus, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, Temivinphos, Terbam, Terbufos, Tetrachlorvinphos, Tetradifon, Tetra-methrin, Tetramethrin (1R isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, Trichoderma atroviride, triflumuron, trimethacarb, vamidothion, vaniliprole, verbutin, Verticillium lecanii, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds, such as herbicides, or with fertilizers and growth regulators, safeners or semichemicals is also possible.

When used as insecticides in their commercially available formulations and in the use forms prepared with these formulations, the active compounds according to the invention can furthermore exist in the form of a mixture with synergists. Synergists are compounds by which the activity of the active compounds is increased without it being necessary for the synergist added to be active itself.

When employed as insecticides, the active compounds can be present, in their commercially available formulations and in the use forms prepared from these formulations, as a mixture with inhibitors, which reduce the degradation of the active compound post-application in the plant's environment, on the surface of plant parts or in plant tissues.

The active compound content of the use forms prepared from the commercially available formulations can vary within broad ranges. The active compound concentration of the use forms can be from 0.0000001 up to 95% by weight of active compound, preferably between 0.001 and 1% by weight.

They are applied in a customary manner adapted to suit the use forms.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defence of the plants against animal and microbial pests, such as against insects, mites, phytopathogenic fiugi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, tobacco, oilseed rape and fruit plants (with the fruits apples, pears, citrus fruits and grapes), with particular emphasis on maize, soybeans, potatoes, cotton, tobacco and oilseed rape. Traits which are especially emphasized are the increased defence of the plants against insects, arachnids, nematodes and slugs owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defence of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "TAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize) Bollgard® (cotton), Nucoton® (cotton) and NewLeaf® (potato). Examples of herbicide-tolerant plants which may be mentioned are maize cultivars, cotton cultivars and. soybean cultivars which are commercially available under the trade names Roundup Ready® (tolerance to glyphosate, for example maize, cotton, soybean) Liberty Link® (tolerance to phosphinothricin, for example oilseed rape IMI® (tolerance to imidazolinones) and STS® (tolerance to sulphonylureas, for example maize). Herbicide-resistant plants (plants bred in a conventional manner for herbicide tolerance) which may be mentioned include also the varieties commercially available under then name Clearfield® (for example maize). Naturally, these statements also apply to plant cultivars having these genetic traits or genetic traits still to be developed, which plant cultivars will be developed and/or marketed in the future.

The plants listed can be treated particularly advantageously in accordance with the invention with the compounds of the general formula I or the active compound mixtures according to the invention. The preferred ranges stated above for the active compounds and mixtures also apply to the treatment of these plants. Particularly emphasis may be given to the treatment of plants with the compounds or mixtures specifically mentioned in the present text.

The active compounds according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp..

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp..

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp..

From the order of the Heteropterida, for example, *Cimex* spp., *Triatoma* spp., *Rhodnius* spp. and *Panstrongylus* spp..

From the order of the Blattarida, for example, *Blatta orientalis, Periplaneta americana, Blattella germanica* and *Supella* spp..

From the sub-class of the Acari (Acarida) and the orders of the Meta-and Mesostigmata, for example, *Argas* spp., *Ornithodorus* spp., *Otobius* spp., *Ixodes* spp., *Amblyomma* spp., *Boophilus* spp., *Dermacentor* spp., *Haemaphysalis* spp., *Hyalomma* spp., *Rhipicephalus* spp., *Dermanyssus* spp., *Raillietia* spp., *Pneumonyssus* spp., *Sternostoma* spp. and *Varroa* spp..

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp..

The active compounds of the formula (I) according to the invention are also suitable for combating arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80%, either directly or after dilution by a factor of 100 to 10 000, or they may be used in the form of a chemical bath.

Furthermore, it has been found that the compounds according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fingicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid, triflumuron, chlothianidin, spinosad, tefluthrin, and fungicides, such as epoxyconazole, hexaconazole, azaconazole, propiconazole, tebuconazole, cyproconazole, metconazole, imazalil, dichlofluanid, tolylfluanid, 3-iodo-2-propinylbutyl carbamate, N-octyl-isothiazolin-3-one and 4,5-dichloro-N-octylisothiazolin-3-one.

The compounds according to the invention can at the same time be employed for protecting objects which come into contact with salt water or brackish water, in particular hulls, screens, nets, buildings, moorings and signalling systems, against fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term *Cirripedia (cirriped crustaceans)*, is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin) sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thio-cyanate, copper naphthenate and tributyltin halides to be dispensed with, or the concentration of these compounds to be substantially reduced.

If appropriate, the ready-to-use antifouling paints can additionally comprise other active compounds, preferably algicides, fingicides, herbicides, molluscicides, or other antifouling active compounds.

Preferably suitable components in combination with the antifouling compositions according to the invention are:

algicides such as 2-tert-butylarnino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butyl-carbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacrb; Fe chelates;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenyhnaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coloptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Brassica, Cucumis, Cucurbita, Helianthus, Daucus, Glycine, Gossypium, Ipomoea, Lactuca, Linum, Lycopersicon, Nicotiana, Phaseolus, Pisum, Solanurn, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyl-octenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre-and post-emergence.

At certain concentrations or application rates, the active compounds according to the invention can also be employed for controlling animal pests and fingal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water.

Suitable solid carriers are: for example ammonium salts and ground natural minerals, such as kaolins, clays, talc, chalk, quartz, attapulgite, montmorillonite or diatomaceous earth, ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compounds, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example
acetochlor, acifluorfen(-sodium), aclonifen, alachlor, alloxydim(-sodium), ametryne, amicarbazone, amidochlor, amidosulftiron, anilofos, asulam, atrazine, azafenidin, azimsulfuron, beflubutamid, benazolin(-ethyl), benfuresate, bensulfuron(-methyl), bent-azone, benzfendizone, benzobicyclon, benzofenap, benzoylprop (-ethyl), bialaphos, bifenox, bispyribac(-sodium), bromobutide, bromofenoxim, bromoxynil, butachlor, buta-fenacil(allyl), butroxydim, butylate, cafenstrole, caloxydim, carbetamide, carfen-trazone(ethyl), chlomethoxyfen, chloramben, chloridazon, chlorimuron (-ethyl), chlornitrofen, chlorsulfuron, chlortoluron, cinidon(-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicambna, dichlorprop (-P), diclofop (-methyl), diclosulam, diethatyl (ethyl), difenzoquat, diflufenican, diflufenzopyr, dimefuron, dimepiperate, dimetha-chlor, dimethametryn, dimethenamid, dimexyflam, dinitramine, diphenamid, diquat, dithiopyr, diuron, dymron, epropodan, EPTC, esprocarb, ethalfluralin, ethametsulf-uron(-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, flora-sulam, fluazifop (-P-butyl), fluazolate, flucarbazone (-sodium), flufenacet, flumetsulam, flumiclorac (-pentyl), flumioxazin, flumipropyn, flumetsulam, fluometuron, fluoro-chloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flur-primidol, flurtamone, fluthiacet (-methyl), fluthiamide, fomesafen, foramsulfuron, glu-fosinate (-ammonium), glyphosate (-isopropylammonium), halosafen, haloxyfop (-ethoxyethyl, -P-methyl), -hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobrom-uron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalide, pyriminobac (-rnethyl), pyrithiobac (-sodium), quinchlorac, quinmerac, quinoclamine, quizalofop (-P-ethyl, -P-tefuryl), rimsulfuron, sethoxydim, sim-azine, simetryn, sulcotrione, sulfentrazone, sulfometuron (-methyl), sulfosate, sulfosulf-uron, tebutam, tebuthiuron, tepraloxydim, terbuthylazine, terbutryn, thenylchlor, thia-fluamide, thiazopyr, thidiazimin, thifensulfuron (-methyl), thiobencarb, tiocarbazil, tralkoxydim, triallate, triasulfuron, tribenuron (-methyl), triclopyr, tridiphane, tri-fluralin, trifloxysulfuron, triflusulfuron (-methyl), tritosulfuron.

Others which are suitable for mixtures are known safeners, for example:

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and soil conditioners, is also possible.

The active compounds can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The preparation and use of the active compounds according to the invention can be seen from the examples which follow.

PREPARATION EXAMPLES

Process A

Example I-1-a-1

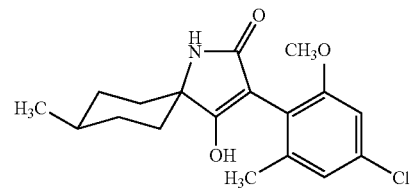

6.7 g of the compound of Preparation Example II-1 in 40 ml of anhydrous toluene are added dropwise to 5.43 g (0.047 mol) of potassium tert-butoxide in 18 ml of anhydrous tetrahydrofuran at reflux temperature.

The reaction mixture is stirred under reflux for 1.5 h. Then, 60 ml of water are added, the aqueous phase is separated off and the organic phase is extracted with water. The aqueous phases are washed once more with toluene and brought to pH 1 with concentrated hydrochloric acid at 0-20° C. The precipitate is filtered off with suction, washed and dried. Purification is by column chromatography on silica gel (dichloromethane:ethyl acetate, 5:1).

Yield: 3.2 g/52% of theory). M.p.: >220° C.

Process P

Example No. I-1-a-18

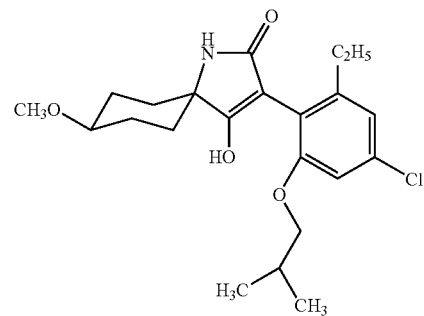

At 0° C. to 5° C., add 3.54 g of potassium tert-butoxide (95%) to 12.12 g of iso-butanol; heat briefly. Then add the copper(I) iodide (0.571 g; 3 mmol) and 1.34 g of the compound of Example I-a-10 (DE-A-10301804); then heat at 110° C. The mixture is stirred for 24 hours at 100° C. to 110° C. The mixture is filtered with suction over Celite, the solids are discarded and the filtrate is acidified and evaporated on a rotary evaporator.

A separation by flash column chromatography on silica gel is carried out, using ethyl acetate. The fractions which, according to LC/MS, contained the product were subjected to RP column chromatography with a gradient programme. The column was preconditioned with a 50:50 mixture of water and methanol.

Yield: 190 mg of white powder=15% of theory.

M.p. =117° C.

The following compounds of the formula (I-1-a) are obtained analogously to Example (I-1-a-1) and in accordance with the general preparation instructions

(I-1-a)

| Ex. No. | W | X | Y | D | A | B | M.p. ° C. | Isomer |
|---|---|---|---|---|---|---|---|---|
| I-1-a-2 | OCH$_3$ | CH$_3$ | Cl | H | —(CH$_2$)$_2$—O—(CH$_2$)$_2$— | | >220 | — |
| I-1-a-3 | OCH$_3$ | C$_2$H$_5$ | Cl | H | —(CH$_2$)$_2$—CHOCH$_3$—(CH$_2$)$_2$— | | 223 | β |
| I-1-a-4 | OCH$_3$ | C$_2$H$_5$ | Cl | H | —(CH$_2$)$_2$—CHCH$_3$—(CH$_2$)$_2$— | | 232 | β |
| I-1-a-5 | OCH$_3$ | C$_2$H$_5$ | Cl | H | CH$_3$ | CH$_3$ | 141 | — |
| I-1-a-6 | OCH$_3$ | C$_2$H$_5$ | Cl | H | —(CH$_2$)$_5$— | | 236 | — |
| I-1-a-7 | OCH$_3$ | C$_2$H$_5$ | Cl | —CH—CH—CH$_2$— (with (CH$_2$)$_3$) | | H | 169 | Isomer mixture |
| I-1-a-8 | OCH$_3$ | CH$_3$ | Cl | H | —(CH$_2$)$_2$—CHOCH$_3$—(CH$_2$)$_2$— | | 318 | β |
| I-1-a-9 | OC$_2$H$_5$ | C$_2$H$_5$ | Cl | H | —(CH$_2$)$_2$—CHOCH$_3$—(CH$_2$)$_2$— | | 96 | β |
| I-1-a-10 | OCH$_3$ | CH$_3$ | Cl | H | CH$_3$ | CH$_3$ | 206 | — |
| I-1-a-11 | OC$_2$H$_5$ | C$_2$H$_5$ | Cl | H | CH$_3$ | CH$_3$ | 207 | — |
| I-1-a-12 | OCH$_3$ | C$_2$H$_5$ | Cl | C$_2$H$_5$ | CH$_3$ | H | 176-178 | — |
| I-1-a-13 | OCH$_3$ | C$_2$H$_5$ | Cl | c-C$_6$H$_{11}$ | CH$_3$ | H | 184 | — |
| I-1-a-14 | OCH$_3$ | C$_2$H$_5$ | Cl | | cyclopropyl | H | 154-157 | — |
| I-1-a-15 | OCH$_3$ | C$_2$H$_5$ | Cl | CH$_3$ | C$_2$H$_5$ | H | *1) | — |
| I-1-a-16 | OCH$_3$ | C$_2$H$_5$ | Cl | —(CH$_2$)$_3$— | | H | Decomp. | — |
| I-1-a-17 | OC$_2$H$_5$ | CH$_3$ | Cl | H | —(CH$_2$)$_2$—CHOCH$_3$—(CH$_2$)$_2$— | | 202 | β |
| I-1-a-18[1)] | O-i-C$_4$H$_9$ | C$_2$H$_5$ | Cl | H | —(CH$_2$)$_2$—CHOCH$_3$—(CH$_2$)$_2$— | | 117 | β |
| I-1-a-19[1)] | O—CH$_2$—cyclopropyl | C$_2$H$_5$ | Cl | H | —(CH$_2$)$_2$—CHOCH$_3$—(CH$_2$)$_2$— | | Wax*2) | β |
| I-1-a-20[1)] | O—CH$_2$—CH$_2$—OCH$_3$ | C$_2$H$_5$ | Cl | H | —(CH$_2$)$_2$—CHOCH$_3$—(CH$_2$)$_2$— | | 61 | β |
| I-1-a-21[1)] | OC$_3$H$_7$ | C$_2$H$_5$ | Cl | H | —(CH$_2$)$_2$—CHOCH$_3$—(CH$_2$)$_2$— | | Wax*3) | β |

*1) $^1$H-NMR (400 MHz, d$_6$-DMSO): δ = 2.43 (m, 2-H, Ar—C$\underline{H}_2$—CH$_3$), 2.77 (s, 3H, N—C$\underline{H}_3$) ppm

*2) $^1$H-NMR (400 MHz, d$_6$-DMSO): δ = 2.42(m, 2-H, Ar—C$\underline{H}_2$—CH$_3$), 3.82 (m, 2H, O—C$\underline{H}_2$—CH$_2$) ppm

*3) $^1$H-NMR (400 MHz, d$_6$-DMSO): δ = 0.27-0.3, 0.42-0.45 (2m, 4H, cyclopropyl-C$\underline{H}_2$), 1.02 (t, 3H, ArCH$_2$—C$\underline{H}_3$) ppm 1) Process P

Example No. I-1-b-1

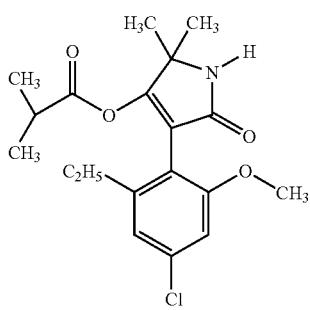

200 mg (0.57 mol) of the compound of Example I-1l-a-5 are introduced into 5 ml of anhydrous ethyl acetate and treated with 0.94 ml (0.57 mmol) of triethylamine. 0.71 ml (0.57 mmol) of isobutyryl chloride in 1 ml of ethyl acetate are added under reflux and the mixture is heated for 2.5 h under reflux.

The reaction solution is cooled and concentrated and the residue is chromatographed on silica gel with a heptane/ethyl acetate gradient of from 100/0 to 0/100.

Yield: 90 mg (43% of theory) M.p. 131° C. The following compounds of the formula (I-1-b) are obtained analogously to Example (I-1 -b-1) and following the general preparation instructions

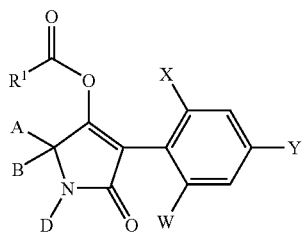

(I-1-b)

| Ex. No. | W | X | Y | D | A | B | $R^1$ | M.p. ° C. | Isomer |
|---|---|---|---|---|---|---|---|---|---|
| I-1-b-2 | $OCH_3$ | $C_2H_5$ | Cl | H | —$(CH_2)_5$— | | i-$C_3H_7$ | 221 | — |
| I-1-b-3 | $OCH_3$ | $C_2H_5$ | Cl | H | —$(CH_2)_2$—$CHCH_3$—$(CH_2)_2$— | | i-$C_3H_7$ | 161 | β |
| I-1-b-4 | $OCH_3$ | $C_2H_5$ | Cl | H | —$(CH_2)_2$—$CHCH_3$—$(CH_2)_2$— | | t-$C_4H_9$ | 169 | β |
| I-1-b-5 | $OCH_3$ | $C_2H_5$ | Cl | H | $CH_3$ | $CH_3$ | t-$C_4H_9$ | 148 | — |
| I-1-b-6 | $OCH_3$ | $C_2H_5$ | Cl | H | —$(CH_2)_2$—$CHOCH_3$—$(CH_2)_2$— | | i-$C_3H_7$ | 201 | β |
| I-1-b-7 | $OC_2H_5$ | $C_2H_5$ | Cl | H | $CH_3$ | $CH_3$ | $H_3C$—O—$CH_2$ | 130 | — |
| I-1-b-8 | $OCH_3$ | $CH_3$ | Cl | H | $CH_3$ | $CH_3$ | $H_3C$—O—$CH_2$ | 149–153 | — |
| I-1-b-9 | $OCH_3$ | $C_2H_5$ | Cl | ▷ | H | H | t-$C_4H_9$' | *1.07(s, 9H, t-Bu)-<br>2.40(m, 2H, C$\underline{H}_2$—Ar) | — |
| I-1-b-10 | $OCH_3$ | $C_2H_5$ | Cl | $CH_3$ | $C_2H_5$ | H | t-$C_4H_9$— | Oil | — |
| I-1-b-11 | $OC_2H_5$ | $C_2H_5$ | Cl | H | —$(CH_2)_2$—$CHOCH_3$—$(CH_2)_2$— | | i-$C_3H_7$— | 226–229 | β |
| I-1-b-12 | $OCH_3$ | $C_2H_5$ | Cl | H | —$(CH_2)_2$—$CHOCH_3$—$(CH_2)_2$— | | $C_4H_9$—CH($C_2H_5$)— | 138 | β |
| I-1-b-13 | $OC_2H_5$ | $C_2H_5$ | Cl | H | —$(CH_2)_2$—$CHOCH_3$—$(CH_2)_2$— | | $C_4H_9$—CH($C_2H_5$)— | 171 | β |
| I-1-b-14 | $OCH_3$ | $C_2H_5$ | Cl | H | —$(CH_2)_2$—$CHOCH_3$—$(CH_2)_2$— | | $C_2H_5$—C$(CH_3)_2$— | 216–218 | β |
| I-1-b-15 | $OC_2H_5$ | $C_2H_5$ | Cl | H | —$(CH_2)_2$—$CHOCH_3$—$(CH_2)_2$— | | $C_2H_5$—C$(CH_3)_2$— | 237–239 | β |
| I-1-b-16 | $OCH_3$ | $C_2H_5$ | Cl | H | —$(CH_2)_2$—$CHOCH_3$—$(CH_2)_2$— | | $H_5C_2$—O—$CH_2$ | 154–159 | β |
| I-1-b-17 | $OCH_3$ | $C_2H_5$ | Cl | H | —$(CH_2)_2$—$CHOCH_3$—$(CH_2)_2$— | | $(C_8H_{17}$—CH=CH—$C_7H_{14}$— | *3.21(m, 1H, C$\underline{H}$OCH$_3$)<br>5.35(m, 2H, C$\underline{H}$=C$\underline{H}$) | β |

*$^1$H-NMR (400 MHz, CDCl$_3$); shifts δ in ppm

Example No. I-1-c-1

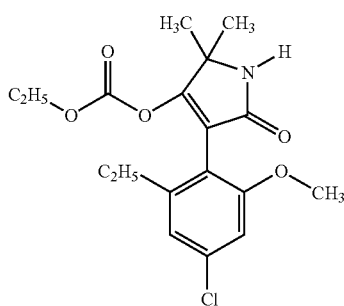

200 mg (0.57 mmol) of the compound of Example I-1-a-5 are introduced into 5 ml of anhydrous $CH_2Cl_2$ and treated with 0.94 ml (0.57 mmol) of triethylamine. 0.64 ml (0.57 mmol) of ethyl chloroformate in 1 ml of $CH_2Cl_2$ are added at 10 to 20° C. and the mixture is stirred for 1.5 h at room temperature. The reaction solution was concentrated and the residue was chromatographed on silica gel with a heptane/ethyl acetate gradient of from 100/0 to 0/100.

Yield: 0.19 g (95 % of theory) M.p. 222° C.

The following compounds of the formula (I-1-c) are obtained analogously to Example (I-1-c-1) and following the general preparation instructions

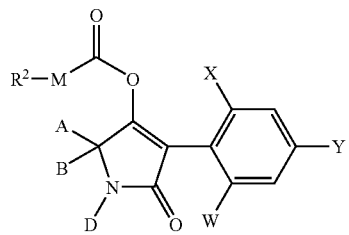

(I-1-c)

| Ex. No. | W | X | Y | D | A | B | M | R² | M.p. °C. | Isomer |
|---|---|---|---|---|---|---|---|---|---|---|
| I-1-c-2 | OCH₃ | C₂H₅ | Cl | H | —(CH₂)₅— | | O | C₂H₅ | 208 | — |
| I-1-c-3 | OCH₃ | C₂H₅ | Cl | H | —(CH₂)₂—CHCH₃—(CH₂)₂— | | O | C₂H₅ | 187 | β |
| I-1-c-4 | OCH₃ | C₂H₅ | Cl | H | —(CH₂)₂—CHOCH₃—(CH₂)₂— | | O | C₂H₅ | 161 | β |
| I-1-c-5 | OCH₃ | C₂H₅ | Cl | CH₃ | C₂H₅ | H | O | C₂H₅ | *2.98(s, 3H, N<u>CH₃</u>)— 3.71 (s, 3H, O<u>CH₃</u>) | — |
| I-1-c-6 | OCH₃ | C₂H₅ | Cl | c-C₆H₁₁ | CH₃ | H | O | C₂H₅ | *4.2 (m, 2H, O<u>CH₂</u>) | — |
| I-1-c-7 | OCH₃ | C₂H₅ | Cl | C₂H₅ | CH₃ | H | O | C₂H₅ | *4.2 (m, 2H, O<u>CH₂</u>) | — |
| I-1-c-8 | OCH₃ | C₂H₅ | Cl | ▷ | H | H | O | C₂H₅ | *2.8 (m,1H,H) | — |
| I-1-c-9 | OCH₃ | CH₃ | Cl | H | CH₃ | CH₃ | O | C₂H₅ | 141-145 | — |
| I-1-c-10 | OC₂H₅ | C₂H₅ | Cl | H | CH₃ | CH₃ | O | C₂H₅ | *1.46 (d, 6H, C(CH₃)₂) | — |
| I-1-c-11 | OC₂H₅ | C₂H₅ | Cl | H | —(CH₂)₂—CHOCH₃—(CH₂)₂— | | O | C₂H₅ | 188-191 | β |
| I-1-c-12 | OC₂H₅ | C₂H₅ | Cl | H | —(CH₂)₂—CHOCH₃—(CH₂)₂— | | O | CH₂=CH—CH₂— | 159-161 | β |
| I-1-c-13 | OCH₃ | C₂H₅ | Cl | H | —(CH₂)₂—CHOCH₃—(CH₂)₂— | | O | CH₂=CH—CH₂— | 138-140 | β |
| I-1-c-14 | OCH₃ | CH₃ | Cl | H | —(CH₂)₂—CHOCH₃—(CH₂)₂— | | O | C₂H₅ | 170 | β |
| I-1-c-15 | OCH₃ | C₂H₅ | Cl | H | —(CH₂)₂—CHOCH₃—(CH₂)₂— | | O | C₄H₉—CH(C₂H₅)—CH₂— | 98-101 | β |
| I-1-c-16 | OC₂H₅ | C₂H₅ | Cl | H | —(CH₂)₂—CHOCH₃—(CH₂)₂— | | O | C₄H₉—CH(C₂H₅)—CH₂— | 114 | β |
| I-1-c-17 | OCH₃ | C₂H₅ | Cl | | —(CH₂)₃— | H | O | C₂H₅ | *4.2 (m, 2H, O<u>CH₂</u>)— | — |

*¹H-NMR (400 MHz, CDCl₃); shifts δ in ppm

Example I-d-1

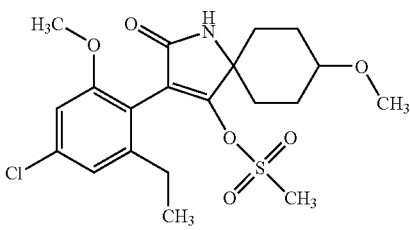

First, 0.09 ml of triethylamine and then 0.069 g (0.601 mmol) of methanesulphonyl chloride are added to a solution of 0.2 g (0.547 mmol) of the compound of Example I-1-a-3 in anhydrous $CH_2Cl_2$. After the mixture has been stirred overnight at room temperature, it is treated with 10 ml of sodium hydrogen carbonate solution, the phases are separated and the organic phase is subsequently dried with sodium sulphate and then freed from solvent in vacuo. The residue thus obtained is chromatographed on silica gel with an n-heptane/ethyl acetate gradient of from 100/0 to 0/100.

Yield: 0.14 g (58% of theory) M.p.: 210-214° C.

Example I-1-f-1

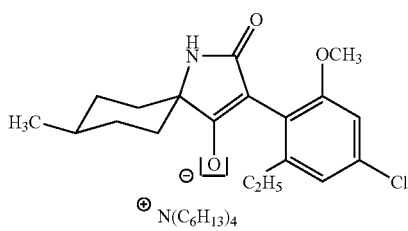

9 ml of a 10% strength solution of tetrahexylammonium hydroxide in methanol are added to a solution of 0.75 g of the compound of Example I-1 -a-3 (1.95 mmol) in 20 ml of anhydrous methanol and stirring is continued for 30 minutes at room temperature. The mixture is freed in vacuo from solvent and treated with a total of three more portions of 50 ml of methanol and the solvent is removed, which gives 1.44 g (yield 97%) in the form of a waxy solid.

$^1$H NMR (400 MHz, $d_6$-DMSO): δ=0.88 (t, 12, 4 $CH_3$), 3.56 (s, 3H, $OCH_3$) ppm In Example I-1-f-2,

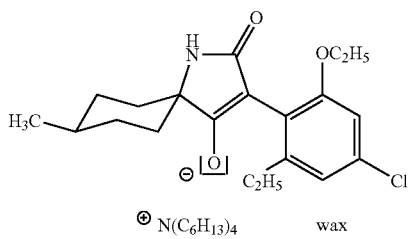

is obtained analogously to Example I-1-f-1.

$^1$H NMR (400 MHz, $d_6$-DMSO): δ=0.88 (t, 12, 4 CH3), 3.83 (s, 2H, OCH2) ppm

Example No. II-1

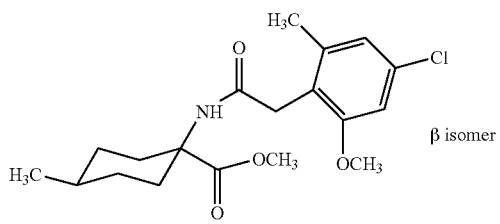

β isomer 5.2 g of 4-chloro-2-methoxy-6-methylphenylacetic acid and 5.4 ml (0.073 mol) of thionyl chloride are stirred at 50° C. until the evolution of gas has ceased.

Excess thionyl chloride is evaporated on a rotary evaporator at 50° C., the residue is taken up in 50 ml of anhydrous toluene, and excess thionyl chloride is again evaporated on a rotary evaporator. The residue is taken up in 30 ml of anhydrous tetrahydrofuran (solution 1). 5.1 g of methyl 1-amino-4-methylcyclohexanecarboxylate hydrochloride are introduced into 50 ml of anhydrous tetrahydrofuran, and 7.5 ml (0.053 mol) of triethylamine are added. Then, solution 1 is added dropwise at 0-10° C.

Stirring is continued for 1 h at room temperature.

The solvent is evaporated on a rotary evaporator, the residue is taken up in a 0.5 N solution of hydrochloric acid in dichloromethane, the mixture is extracted, the extract is dried and the solvent is distilled off. The residue is recrystallized from MTB ether/n-hexane.

Yield: 6.7 g (68% of theory), m.p.: 166° C.

Example No. II-2

6.4 g of the compound of Preparation Example No. XXIX-1 in 60 ml of methylene chloride are added to 9.8 g (0.1 mol) of concentrated sulphuric acid at an internal temperature of 30-40° C. The mixture is stirred for 2 h at 30-40° C. Then, 13.5 ml of anhydrous methanol are added in such a way that an internal temperature of 40° C. is established. Stirring is continued for 6 h at 40-70° C.

The reaction solution is poured onto 0.1 kg of ice, extracted with dichloromethane and washed with $NaHCO_3$ solution. The mixture is then dried, the solvent is distilled off and the residue is recrystallized from MTB ether/n-hexane.

Yield: 5.9 g (83% of theory), m.p.: 156° C.

The following compounds of the formula II are obtained analogously to Examples II-1 and II-2 and following the general preparation instructions

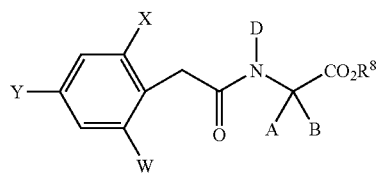

(II)

| Ex. No. | W | X | Y | D | A | B | R[8] | Isomer | M.p. °C. |
|---|---|---|---|---|---|---|---|---|---|
| II-3 | OCH$_3$ | C$_2$H$_5$ | Cl | H | —(CH$_2$)$_2$—CHOCH$_3$—(CH$_2$)$_2$— | | CH$_3$ | β | 105 |
| II-4 | OCH$_3$ | C$_2$H$_5$ | Cl | H | —(CH$_2$)$_2$—CH CH$_3$—(CH$_2$)$_2$— | | CH$_3$ | β | 131 |
| II-5 | OCH$_3$ | C$_2$H$_5$ | Cl | H | CH$_3$ | CH$_3$ | CH$_3$ | — | 163 |
| II-6 | OCh$_3$ | C$_2$H$_5$ | Cl | H | —(CH$_2$)$_5$— | | CH$_3$ | — | 124 |
| II-7 | OCH$_3$ | C$_2$H$_5$ | Cl | —CH—CH—CH$_2$— (CH$_2$)$_3$ | | H | C$_2$H$_5$ | Isomer mixture | Oil |
| II-8 | OCH$_3$ | CH$_3$ | Cl | H | —(CH$_2$)$_2$—CHOCH$_3$—(CH$_2$)$_2$ | | CH$_3$ | β | 127 |
| II-9 | OC$_2$H$_5$ | C$_2$H$_5$ | Cl | H | —(CH$_2$)$_2$—CHOCH$_3$—(CH$_2$)$_2$ | | CH$_3$ | β | 100 |
| II-10 | OCH$_3$ | CH$_3$ | Cl | H | CH$_3$ | CH$_3$ | CH$_3$ | — | 157 |
| II-11 | OC$_2$H$_5$ | C$_2$H$_5$ | Cl | H | CH$_3$ | CH$_3$ | CH$_3$ | — | 118 |
| II-12 | OCH$_3$ | C$_2$H$_5$ | Cl | C$_2$H$_5$ | CH$_3$ | H | C$_2$H$_5$ | — | *1.47 (d, 3H, CH(CH$_3$)) |
| II-13 | OCH$_3$ | C$_2$H$_5$ | Cl | c-C$_6$H$_{11}$ | CH$_3$ | H | C$_2$H$_5$ | — | *1.44 (d, 3H, CH(CH$_3$)) |
| II-14 | OCH$_3$ | C$_2$H$_5$ | Cl | ▷ | H | H | C$_2$H$_5$ | — | *3.03 (m, 1H, N—◁ H) |
| II-15 | OCH$_3$ | C$_2$H$_5$ | Cl | CH$_3$ | C$_2$H$_5$ | H | C$_2$H$_5$ | — | *2.59 (q, 2H, Ar—CH$_2$) |
| II-16 | OCH$_3$ | C$_2$H$_5$ | Cl | | —(CH$_2$)$_3$— | H | CH$_3$ | — | **1.13 (t, 3H, ArCH$_2$—CH$_3$), 3.76 (s, 3H, ArOCH$_3$) |
| II-17 | OC$_2$H$_5$ | CH$_3$ | Cl | H | —(CH$_2$)$_2$—CHOCH$_3$—(CH$_2$)$_2$— | | CH$_3$ | β | ***1.31 (t, 3H, Ar—O—CH$_2$—CH$_3$), 4.00 (q, 2H, Ar—O—CH$_2$—CH$_3$) |

*$^1$H NMR (400 MHz, CDCl$_3$): shifts δ in ppm
**$^1$H NMR (400 MHz, d$_6$-DMSO): shifts δ in ppm
***$^1$H NMR (400 MHz, CD$_3$CN): shifts δ in ppm Example No. XXIX-1

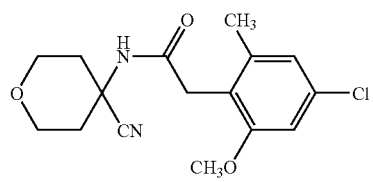

5.2 g of 4-chloro-2-methoxy-6-methylphenylacetic acid and 5.4 ml (0.073 mol) of thionyl chloride are stirred at 50° C. until the evolution of gas has ceased.

Excess thionyl chloride is evaporated on a rotary evaporator at 50° C., the residue is taken up in 50 ml of anhydrous toluene and excess thionyl chloride is again evaporated on a rotary evaporator. The residue is taken up in 30 ml of anhydrous tetrahydrofuran (solution 1). 6.11 g of 4-aminotetrahydropyran-4-carbonitrile are introduced into 50 ml of anhydrous tetrahydrofuran, 3.4 ml of triethylamine are added and solution 1 is added dropwise at 0-10° C.

Stirring is continued for 1 h at room temperature.

The solvent is evaporated on a rotary evaporator and the residue is taken up in a 0.5 N strength solution of hydrochloric acid in dichloromethane, the mixture is extracted, the extract is dried and the solvent is distilled off. The residue is recrystallized from MTB ether/n-hexane.

Yield: 6.4 g (82% of theory), m.p.: 149° C.

Example I-2-a-1

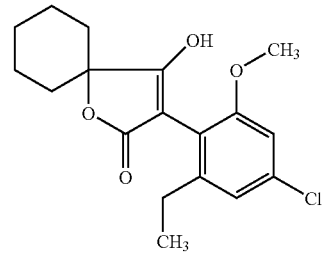

4.2 g of the compound of Example III-1, dissolved in DMF (5 ml), are added dropwise at 0 to 10° C. to 1.84 g of KOtBu in 5 ml of DMF at 0° C. The mixture is stirred overnight at room temperature and the DMF is removed by vacuum distillation. The residue is stirred with water, acidified with HCl, and the precipitate is filtered off with suction and dried.

Yield: 2.8 g (59% of theory), m.p. 90° C.

The following compounds of the formula (I-2-a) are obtained analogously to Example (I-2-a-1) and following the general preparation instructions (I-2-a)

| Ex. No. | W | X | Y | A | B | M.p. °C. |
|---|---|---|---|---|---|---|
| I-2-a-2 | OCH$_3$ | C$_2$H$_5$ | Cl | | —(CH$_2$)$_2$—CHOCH$_3$—(CH$_2$)$_2$— | 90-95 |

Example I-2-b-1

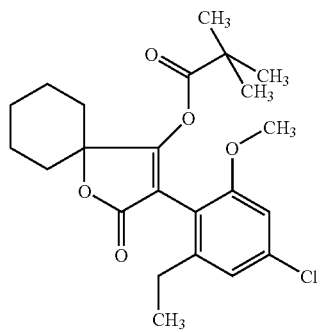

0.34 g of the compound of Example I-2-a-1 are introduced into dichloromethane (10 ml) and triethylamine (0.15 ml), and 0.13 g of pivaloyl chloride is added, with ice-cooling. The mixture is stirred overnight at room temperature and the solution is washed with 10% citric acid and 10% NaOH, separated, dried and concentrated.

Yield 0.3 g (57% of theory).

$^1$H-NMR (400 MHz, CD$_3$CN): δ=1.11 (s, 9H, C(H$_3$)$_3$), 3.72 (s, 3H, ArOCH$_3$) ppm.

The following compounds of the formula (I-2-b) are obtained analogously to Example (I-2-b-1) and following the general preparation instructions (I-2-b)

| Ex. No. | W | X | Y | A | B | R$^1$ | M.p. °C. |
|---|---|---|---|---|---|---|---|
| I-2-b-2 | OCH$_3$ | C$_2$H$_5$ | Cl | | —(CH$_2$)$_5$— | H$_5$C$_2$—C(CH$_3$)$_2$ | *1.07, 1.19 (2s, 6H, C(CH$_3$)$_2$), 3.72, (s, 3H, OCH$_3$) |
| I-2-b-3 | OCH$_3$ | C$_2$H$_5$ | Cl | | —(CH$_2$)$_5$— | i-C$_3$H$_7$ | *2.66 (m, 1H, —CH(CH$_3$)$_2$, 3.72 (s, 3H, OCH$_3$ |
| I-2-b-4 | OCH$_3$ | C$_2$H$_5$ | Cl | —(CH$_2$)$_2$—CHOCH$_3$—(CH$_2$)$_2$— | | H$_5$C$_2$—C(CH$_3$)$_2$— | *3.28, 3.33 (2s, 3H, CH—OCH$_3$) |
| I-2-b-5 | OCH$_3$ | C$_2$H$_5$ | Cl | —(CH$_2$)$_2$—CHOCH$_3$—(CH$_2$)$_2$— | | i-C$_3$H$_7$ | *3.30, 3.32 (2s, 3H, CH—OCH$_3$) |
| I-2-b-6 | OCH$_3$ | C$_2$H$_5$ | Cl | —(CH$_2$)$_2$—CHOCH$_3$—(CH$_2$)$_2$— | | t-C$_4$H$_9$ | *3.29, 3.33 (2s, 3H, CHOCH$_3$), 1.11, 1.12 (2s, 9H, C(CH$_3$)$_3$) |

Example I-2-c-1

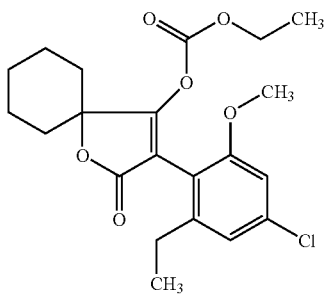

0.67 g of the compound of Example I-2-a-1 are introduced into dichloromethane (10 ml) and triethylamine (0.31 ml), and 0.239 g of ethyl chloroformate is added, with ice-cooling. The mixture is stirred overnight at room temperature and the solution is washed with 10% citric acid and 10% NaOH, separated, dried and concentrated.

Yield: 0.76 g (73% of theory).

$^1$H NMR (400 MHz, CD$_3$CN): δ=3.73 (s, 3H, OCH$_3$), 4.03 (q, 2H, OCH$_2$CH$_3$), 6.87 (d, 1H, Ar—H), 6.95 (d, 1H, Ar—H) ppm.

The following compounds of formula (I-2-c) are obtained analogously to Example (I-2-c-1) and following the general preparation instructions

Example III-1

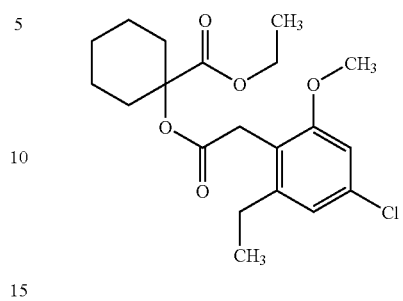

2.09 g of ethyl 1-hydroxycyclohexanecarboxylate and 3 g of the compound of Example XXIV-1 are heated at 120° C. in an oil bath, stirred until the evolution of gas has ceased and then heated briefly at 140° C. Yield: 42 g (59% of theory).

$^1$H NMR (400 MHz, CD$_3$CN): δ=2.58 (q, 2H, CH$_2$—Ar), 3.77 (s, 3H, OCH$_3$), 4.05 (m, 2H, O—CH$_2$—CH$_3$) ppm.

The following compounds of formula (III) are obtained analogously to Example III-1 and following the general preparation instructions

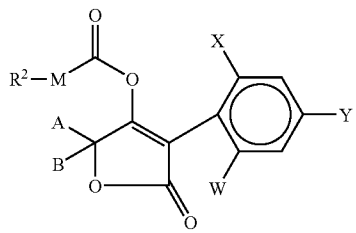

(I-2-c)

| Ex. No. | W | X | Y | A | B | M | R$^2$ | M.p. ° C. |
|---|---|---|---|---|---|---|---|---|
| I-2-c-2 | OCH$_3$ | C$_2$H$_5$ | Cl | —(CH$_2$)—CHOCH$_3$—(CH$_2$)$_2$— | | O | C$_2$H$_5$ | *3.31, 3.33 (2s, 3H, CHOCH$_3$), 3.73 (s, 3H, OCH$_3$ |

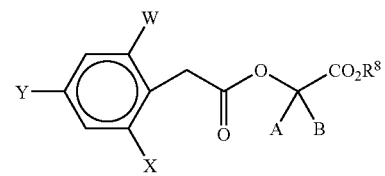

(III)

| Ex. No. | W | X | Y | A | B | R$^8$ | M.p. ° C. |
|---|---|---|---|---|---|---|---|
| III-2 | OCH$_3$ | C$_2$H$_5$ | Cl | —(CH$_2$)$_2$CHOCH$_3$—(CH$_2$)$_2$— | | C$_2$H$_5$ | *2.58 (q, 2H, CH$_2$—Ar), 4.06 (m, 2H, |

-continued

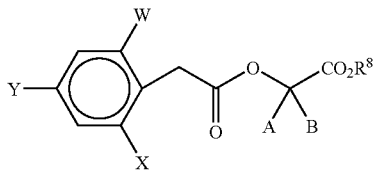

(III)

| Ex. No. | W | X | Y | A | B | R⁸ | M.p. ° C. |
|---|---|---|---|---|---|---|---|
| | | | | | | O—$\underline{CH_2}$—CH₃), 6.88 (d, 1H, Ar—$\underline{H}$), 6.91 (d, 1H, Ar—$\underline{H}$) | |

Example I-8-a-1

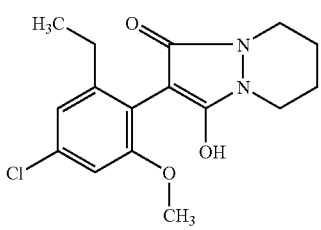

2.5 g (0.007 mol) of the compound of Example XII-1 and 1.673 g (0.015 mol) of potassium tert-butoxide are heated in 100 ml of N,N-dimethylacetamide to 60 to 120° C. The mixture is cooled, acidified, diluted with water and extracted 3 times with toluene. The organic phase is dried, the solvent is removed by vacuum distillation and the residue is filtered through silica gel. This gives 0.9 g of product.

The aqueous phase was reextracted with ethyl acetate and the extract was purified analogously. This gave a further 0.48 g of product.

Total yield: 1.38 g (60% of theory), m.p. 163° C.

Example I-8-b-1

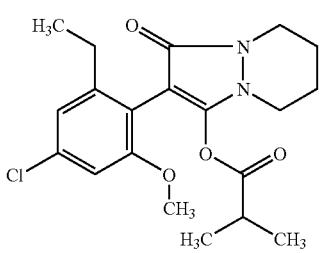

0.14 g of the compound of Example I-8-a-1 and 0.08 ml of triethylamine are introduced into 25 ml of dichloromethane. After 0.05 ml of isobutyryl chloride has been added dropwise, the mixture is stirred for 1 hour at room temperature and then diluted with water, the organic phase is separated off and the solvent is distilled off. The reaction mixture is stirred with n-hexane and a little toluene, and the precipitate is filtered off with suction. Yield: 120 mg (70% of theory), m.p.: 127.5° C.

Example I-8-c-1

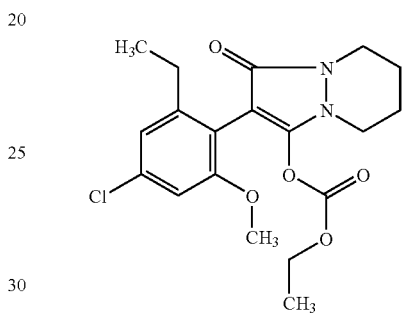

0.15 g of the compound of Example I-8-a-1 and 0.08 ml of triethylamine are introduced into 35 ml of dichloromethane, 0.04 ml of ethyl chloroformate is added dropwise and the mixture is stirred for 1 hour at room temperature. The reaction solution is diluted with water, the organic phase is separated off and dried and the solvent is distilled off. The residue is stirred with n-hexane and a little toluene and the precipitate is filtered off with suction.

Yield: 110 mg (60% of theory), m.p.: 110° C.

Example XII-1

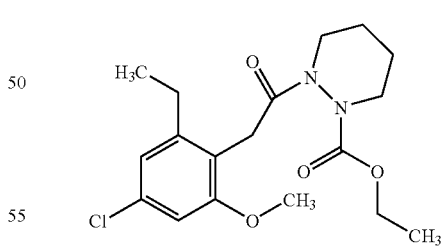

1.9 g of the compound of Example XXVII-2 in 50 ml of dichloromethane are treated with 2.10 g of oxalyl dichloride, the mixture is refluxed for 30 minutes, 1 ml of dimethylformamide is added, the mixture is stirred for a further 30 minutes under reflux, cooled under N₂ atmosphere, the solvent is distilled off and the residue is dissolved in acetonitrile (solution A).

1.31 g of the compound of Example XLI-2 and 1.38 g of potassium carbonate are introduced into 100 ml of acetonitrile, solution A is added dropwise at room temperature and stirring is continued for 4 hours at room temperature. The solids are filtered off, the solvent is evaporated and the residue is filtered through silica gel.

Yield: 2.5 g (83% of theory).

$^1$H NMR (400 MHz, CDCl$_3$): δ=6.85 (d, 1H); 6.70 (d, 1H); 4.50 (ddbr, 1H); 4.30-4.10 (m, 3H); 3.90 (d, 1H); 3.75 (s, 3H); 3.50 (d, 1H); 2.70 (mbr, 2H); 2.60 (q, 2H); 1.65 (mbr, 4H); 1.30 (tr, 3H); 1.20 (tr, 3H) ppm.

Example XLI-1

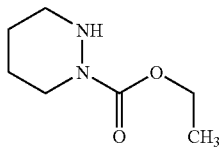

5 g (0.031 mol) of hexahydropyridazine are introduced into 35 ml of dichloromethane, the mixture is treated with 32 ml of water and 0.1 g of tetra-n-butylammonium bromide is added. 4.1 g (0.104 mmol) of sodium hydroxide in 32 ml of water are metered in, while cooling in an ice bath. 3.0 ml of ethyl chloroformate in 30 ml of dichloromethane are added dropwise at 0° C. and the mixture is stirred for 2 hours at 0° C. After the mixture has been stirred for 8 hours at room temperature, the organic phase is separated off, the aqueous phase is extracted with dichloromethane and the organic phase is concentrated by evaporation on a rotary evaporator. The reaction mixture is stirred with water, acidified slightly and washed twice with diethyl ether, and the aqueous phase is basified, extracted with dichloromethane, dried and concentrated by evaporation on a rotary evaporator.

Yield: 3.1 g (63% of theory)

$^1$H NMR (400 MHz, CDCl$_3$): δ=4.20 (q, 2H); 3.55 (tr, br, 2H); 2.90 (tr, br, 2H); 1.65 (m, 4H); 1.30 (tr, 3H) ppm.

Example XIV-1

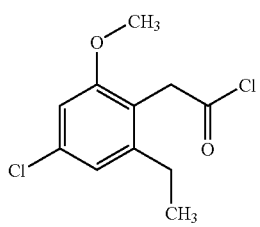

5.78 g of the compound of Example XXVII-2 are introduced into 50 ml of toluene and one drop of DMF. 3.6 g of thionyl chloride are added dropwise at room temperature, and the mixture is stirred overnight under reflux, cooled, concentrated and degassed.

Yield: 6.17 g (98% of theory).

The product was used without further purification, for example for the preparation of Examples III-1 and III-2.

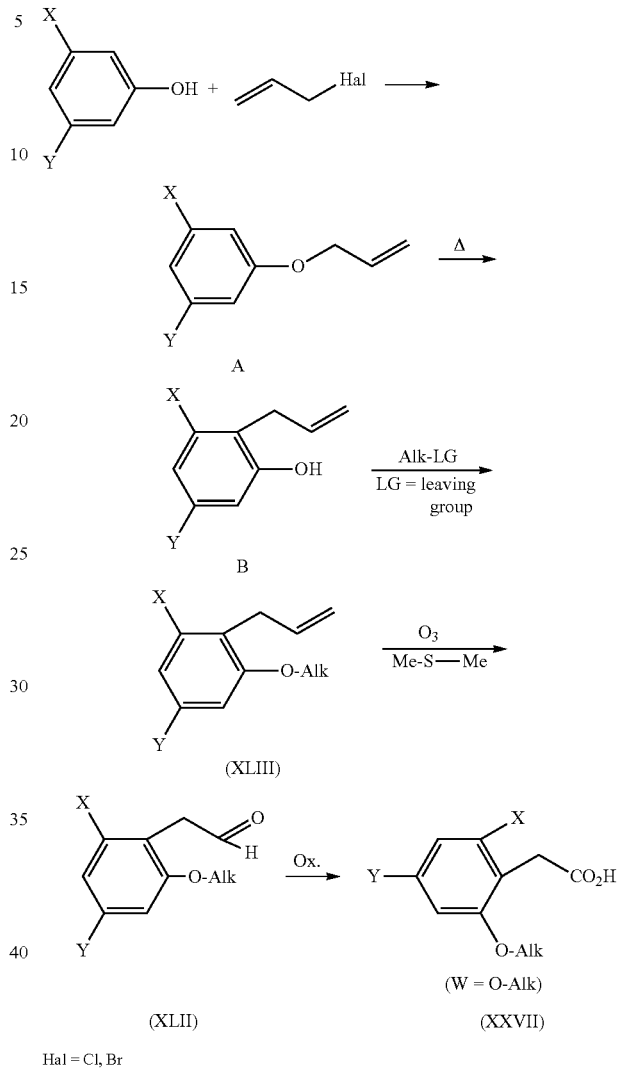

Ex. No. XXVII-1

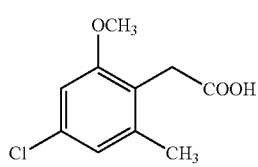

34 g (0.11 mol) of the compound of Preparation Example XLII-1 are introduced, at room temperature, into 350 ml of tert-butanol and 115 g of 2-methyl-2-butene. A solution of 456 ml of water, 155.9 g of NaH$_2$PO$_4$ and 53.9 g of sodium chlorite as a 20% strength solution is then added dropwise at room temperature. Continue stirring for 4 h at room temperature.

The reaction solution is stirred into ethyl acetate, and the organic phase is separated off and extracted twice with ethyl acetate. It is subsequently dried and the solvent is distilled off. The residue is taken up in water, rendered alkaline and extracted. The aqueous phase is acidified and the precipitate is filtered off with suction and dried.

Yield: 11.2 g (47.5% of theory), m.p.: 130-135° C.

Example No. XLII-1

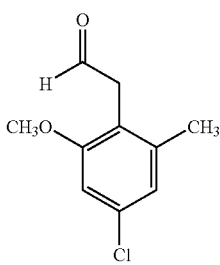

22 g (0.11 mol) of the compound of Preparation Example XLIII-1 is introduced into 60 ml of CH$_2$Cl$_2$ at −70° C. Then, ozone is passed in for 2 hours until uptake is no longer discernible (KI solution turns yellowish-brown). The mixture is flushed with oxygen. When the reaction has ended, 19.4 g of dimethyl sulphide are added dropwise at −70° C. using a pipette, and stirring is continued for 30 minutes. The mixture is allowed to slowly come to room temperature and stirring is continued for 30 minutes at room temperature. The solvent is evaporated in vacuo on a rotary evaporator in a hood.

The residue is now purified by chromatography on silica gel (petroleum ether:ethyl acetate, 15:1).

Yield: 34 g (40% of theory).

Example No. XLIII-1

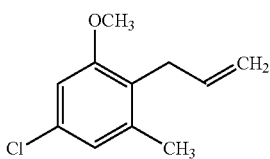

28 g (0.15 mol) of 3-chloro-6-allyl-5-methylphenol of Example B together with 7.4 g (0.18 mol) of NaOH are introduced into 70 ml of H$_2$O. 20.4 g (0.165 mol) of dimethyl sulphate are added dropwise at 20-30° C. and stirring is continued for 7 h at 100° C. The aqueous phase is extracted 3 times with diethyl ether and the organic phase is washed twice with 1N NaOH solution and water. It is dried, the solvent is evaporated on a rotary evaporator and the residue is distilled in vacuo.

Yield: 22 g (b.p.: 65° C.; 0.2 mbar, 76% of theory).

Example A

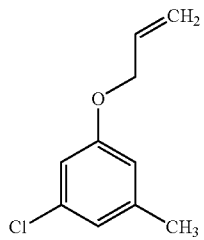

50 g (0.35 mol) of 3-chloro-5-methylphenol, 46.7 g (0.38 mol) of brompropene and 50 g of potassium carbonate are introduced into 80 ml of anhydrous acetone at room temperature. The mixture is refluxed overnight.

The reaction mixture is cooled, treated with 150 ml of water and extracted twice with methyl tert-butyl ether. The organic phase is subsequently washed with 10% strength NaOH solution and dried over potassium carbonate. The solvent is evaporated on a rotary evaporator and the residue is distilled in vacuo.

Yield: 54 g (b.p.: 105° C. at 0.1 mbar; 85% of theory)

Example B

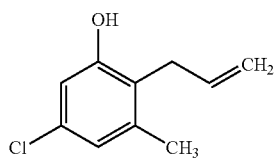

To 53 g (0.29 mol) of the compound of Preparation Example A, add 150 ml of mesitylene at room temperature and reflux for 1-2 days. After the reaction has ended (TLC check), the solvent is evaporated in vacuo on a rotary evaporator. Precision distillation of 110 g of crude product in vacuo gives two isomers, which are introduced into the subsequent reaction for the preparation of Ex. XIII-1 without further purification.

Yield: 28 g (b.p.: 84° C.; 0.12 mbar, 53% of theory) (crude product).

Process R

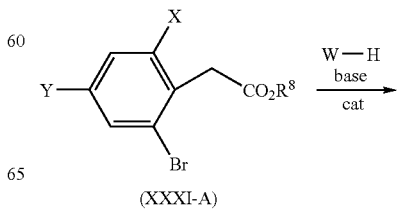

(XXXI-A)

-continued

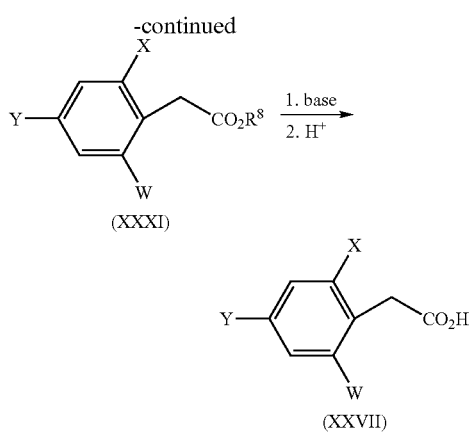

Example No. XXXI-1

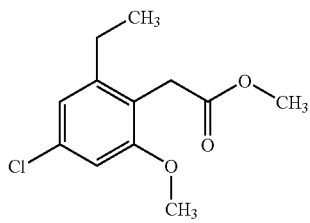

30.1 g (103 mmol) of methyl 2-bromo-4-chloro-6-ethylphenylacetate, 3 g (21 mmol) of copper(I) bromide, 30 ml of ethyl acetate and 210 ml (1105 mmol) of 30 % strength sodium methoxide solution are refluxed overnight. The solvent is subsequently evaporated on a rotary evaporator, the residue is taken up in water/dichloromethane, the mixture is extracted, the extract is dried and the solvent is evaporated on a rotary evaporator.

Yield: 9.4 g (38% of theory)

$^1$H NMR {400 MHz, DMSO-$d_6$}: 1.09 (t, $^3$HH=7 Hz, 3H, CH$_3$); 2.55 (q, $^3$HH=7 Hz, 2H, CH$_2$); 3.58 (s, 3H, OCH$_3$); 3.61 (s, 2H, CH$_2$) 3.78 (s, 3H, OCH$_2$); 6.89 (s, 1H, Ph-H); 6.94 (s, 1H, Ph-H).

MS/CI: 243 (M+1)

Ethyl 2-ethyl-6-ethoxy-4-chlorophenylacetate (XXX-2) is obtained analogously to Example XXX-1

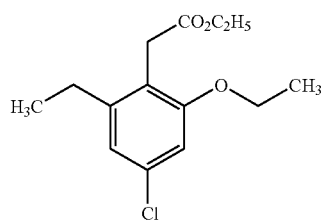

$^1$H NMR {400 MHz, DMSO-$d_6$}: 1.10 (t, $^3$HH =7 Hz, 3H, CH$_3$); 1.18 (t, $^3$HH=7 Hz, 3H, CH$_3$); 1.27 (t, $^3$HH =7 Hz, 3H, CH$_3$); 2.54 (q, $^3$HH=7 Hz, 2H, CH$_2$); 3.58 (s, 2H, CH$_2$); 4.01 (q, $^3$HH=7 Hz, 2H, OCH$_2$) 4.09 (q, $^3$HH=7 Hz, 2H, OCH$_2$); 6.86 (s, 1H, Ph-H); 6.88 (s, 1H, Ph-H) ppm.

MS/Cl 271 (M+1).

Example No. XXVII-2

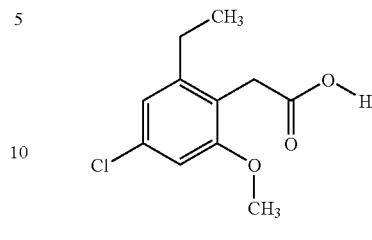

9.4 g (38 mmol) of the compound of Example XXXI-1 are added to 6.5 g (116 mmol) of KOH, 30 ml of water and 40 ml of methanol and the mixture is refluxed overnight. The solvent is then removed in vacuo, and the residue is taken up in water and precipitated with concentrated HCl. The precipitate is filtered, washed with a little water and dried in vacuo.

Yield: 8.6 g (97% of theory)

$^1$H NMR {400 MHz, DMSO-$d_6$}: 1.08 (t, $^3$HH=7 Hz, 3H, CH$_3$); 2.53 (q, $^3$HH=7 Hz, 2H, CH$_2$); 3.51 (s, 3H, CH$_2$); 3.76 (s, 3H, OCH$_3$); 6.86 (s, 1H, Ph-H); 6.89 (s, 1H, Ph-H); 12.2 (s, 1H, CO$_2$H).

MS/CI: 229 (M+1)

2-Ethyl-6-ethoxy-4-chlorophenylacetic acid XXXVII-3 is obtained analogously to Example XXVII-2

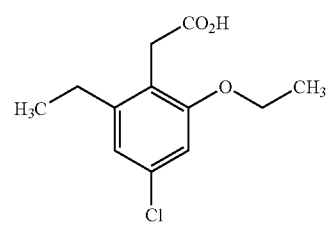

$^1$H NMR {400 MHz, DMSO-$d_6$}: 1.09 (t, $^3$HH=7 Hz, 3H, CH$_3$); 1.28 (t, $^3$HH=7 Hz, 3H, CH$_3$); 2.54 (q, $^3$HH=7 Hz, 2H, CH$_2$); 3.51 (s, 2H, CH$_2$); 4.01 (q, $^3$HH=7 Hz, 2H,OCH$_2$); 6.85 (s, 1H, Ph-H); 6.87 (s, 1H, Ph-H); 12.2 (s 1H, CO$_2$H) ppm.

MS/CI:243 (M+1).

Use Examples:

Example A

| Post-emergence test | |
|---|---|
| Solvent: | 5 parts by weight of acetone |
| Emulsifier: | 1 part by weight of alkylaryl polyglycol ether |

To prepare a suitable active compound preparation, 1 part by weight of active compound is mixed with the stated amount of solvent, the stated amount of emulsifier is added, and the concentrate is diluted with water to the desired concentration.

Test plants with a height of 5-15 cm are sprayed with the active compound preparation in such a way that the amounts of active compound desired in each case are applied per unit area. The concentration of the spray mixture is chosen in such a way that the amounts of active compound desired in each case are applied in 1 000 l of water/ha.

After three weeks, the degree of damage of the plants is scored in % damage in comparison with the development of the untreated control.

| post-emergence | greenhouse | g a.i./ha | sugar beet | *Alopecurus* | *Avena fatua* | *Echinochloa* | *Setaria* | *Abultilon* | *Sinapis* |
|---|---|---|---|---|---|---|---|---|---|
| Ex. I-1-a-3 | | 250 | 0 | 100 | 100 | 100 | 100 | 70 | 80 |

| post-emergence | greenhouse | g a.i./ha | sugar beet | *Alopecurus* | *Avena fatua* | *Echinochloa* | *Setaria* |
|---|---|---|---|---|---|---|---|
| Ex. I-1-a-4 | | 250 | 0 | 100 | 100 | 100 | 100 |

| post-emergence | greenhouse | g a.i./ha | *Alopecurus* | *Avena fatua* | *Echinochloa* | *Setaria* | *Sinapis* |
|---|---|---|---|---|---|---|---|
| Ex. I-1-a-5 | | 250 | 100 | 100 | 100 | 100 | 80 |
| Ex. I-1-a-6 | | 250 | 90 | 100 | 100 | — | 80 |

| post-emergence | greenhouse | g a.i./ha | sugar beet | *Alopecurus* | *Avena fatua* | *Setaria* | *Amaranthus* |
|---|---|---|---|---|---|---|---|
| Ex. I-1-a-1 | | 250 | 0 | 100 | 100 | 100 | — |
| Ex. I-1-a-2 | | 250 | 0 | — | 100 | 100 | 90 |

| pre-emergence | greenhouse | g a.i./ha | *Alopecurus* | *Avena fatua* | *Echinochloa* | *Setaria* | *Abultilon* | *Sinapis* |
|---|---|---|---|---|---|---|---|---|
| Ex. I-1-a-3 | | 250 | 80 | 100 | 100 | 100 | 80 | 80 |
| Ex. I-1-a-4 | | 250 | 90 | 100 | 100 | 100 | — | 90 |

| pre-emergence | greenhouse | g a.i./ha | *Alopecurus* | *Avena fatua* | *Echinochloa* | *Setaria* |
|---|---|---|---|---|---|---|
| Ex. I-1-a-5 | | 250 | 90 | 100 | 100 | 100 |

| pre-emergence | greenhouse | g a.i./ha | sugar beet | *Alopecurus* | *Lolium* | *Setaria* | *Cassia* | *Matricaria* | *Viola* |
|---|---|---|---|---|---|---|---|---|---|
| Ex. I-1-a-1 | | 125 | 0 | 100 | 100 | 100 | 100 | 90 | 90 |

| pre-emergence | greenhouse | g a.i./ha | sugar beet | *Alopecurus* | *Avena fatua* | *Setaria* |
|---|---|---|---|---|---|---|
| Ex. I-1-a-2 | | 250 | 0 | 100 | 80 | 80 |

The figures denote:
0% = no effect (like untreated control)
100% = total destruction After three weeks, the degree of damage of the plants is scored in % damage in comparison with the development of the untreated control.

The figures denote:
0% =no effect (like untreated control)
100% =total destruction Example B

| Pre-emergence test | |
|---|---|
| Solvent: | 5 parts by weight of acetone |
| Emulsifier: | 1 part by weight of alkylaryl polyglycol ether |

To prepare a suitable active compound preparation, 1 part by weight of active compound is mixed with the stated amount of solvent, the stated amount of emulsifier is added, and the concentrate is diluted with water to the desired concentration.

Seeds of the test plant are sown in normal soil. After approximately 24 hours, the soil is sprayed with the active compound preparation in such a way that the amounts of active compound desired in each case are applied per unit area. The concentration of the spray mixture is chosen in such a way that the amounts of active compound desired in each case are applied in 1 000 l of water/ha.

After three weeks, the degree of damage of the plants is scored in % damage in comparison with the development of the untreated control.

Example C

Post-Emergence Crop Plant Tolerance

Seeds of monocotyledonous and dicotyledonous weed and crop plants are placed in sandy loam in wood fibre pots or in plastic pots, covered with soil and grown in the greenhouse or, during the vegetation period, in the open outside the greenhouse, under good growth conditions. 2 to 3 weeks after sowing, the test plants are treated in the one- to three-leaf stage. The test compounds, which are formulated as wettable powder (WP) or as a fluid (EC), are sprayed onto the plants and the soil surface at various dosage rates with a water application rate of 300 l/ha (converted), with added wetter (0.2 to 0.3%). 3 to 4 weeks after the treatment of the test plants, the effect of the preparations is scored visually in comparison with untreated controls (herbicidal activity in per cent (%): 100% activity=plants have died, 0% activity=like control plants).

Use of Safeners

If it is additionally desired to test whether safeners are capable of improving the plant tolerance of test substances with regard to the crop plants, the following options for applying the safeners are used:

Prior to application of the test substances, the crop plants are sprayed with safener at a particular application rate per hectare (usually 1 day prior to application of the test substances).

The safener is applied together with the test substance in the form of a tank mix (the amount of safener being indicated in g/ha or as a safener:herbicide ratio).

The activity of the safener substance can be assessed in comparison with untreated control plants by comparing the effect of test substances on crop plants which have been treated without and with safener.

Results of Greenhouse Experiments With Safener/Pretreatment (Safener Mefenpyr (100 g a.i./ha), One Day Prior to Post-Emergence Treatment With the Herbicide)

TABLE 1'

| | Application rate g a.i./ha | Spring barley observed (%) |
|---|---|---|
| Example I-1-c-7 | 50 | 85 |
| | 25 | 30 |
| | 13 | 15 |
| Example I-1-c-7 + mefenpyr | 500 + 100 | 50 |
| | 25 + 100 | 10 |
| | 13 + 100 | 5 |

TABLE 2'

| | Application rate g a.i./ha | Spring barley observed (%) | Spring wheat observed (%) |
|---|---|---|---|
| Example I-1-c-8 | 100 | | 55 |
| | 50 | 97 | 50 |
| | 25 | 35 | |
| Example I-1-c-8 + mefenpyr | 100 + 100 | | 20 |
| | 50 + 100 | 50 | 15 |
| | 25 + 100 | 15 | |

TABLE 3'

| | Application rate g a.i./ha | Spring barley observed (%) | Spring wheat observed (%) |
|---|---|---|---|
| Example I-2-a-1 | 100 | 20 | 30 |
| | 50 | 15 | 20 |
| | 25 | 10 | 20 |
| Example I-2-a-1 + mefenpyr | 100 + 100 | 10 | 15 |
| | 50 + 100 | 0 | 10 |
| | 25 + 100 | 0 | 5 |

TABLE 4'

| | Application rate g a.i/ha | Spring barley observed (%) |
|---|---|---|
| Example I-2-a-2 | 100 | 97 |
| | 50 | 60 |
| | 25 | 60 |
| Example I-2-a-2 + mefenpyr | 100 + 100 | 40 |
| | 50 + 100 | 30 |
| | 25 + 100 | 20 |

TABLE 5'

| | Application rate g a.i./ha | Spring wheat observed (%) |
|---|---|---|
| Example I-2-c-1 | 100 | 30 |
| | 50 | 20 |

TABLE 5'-continued

| | Application rate g a.i./ha | Spring wheat observed (%) |
|---|---|---|
| Example I-2-c-1 | 100 + 100 | 10 |
| mefenyr | 50 + 100 | 5 |

TABLE 6'

| | Application rate g a.i./ha | Spring barley observed (%) | Spring wheat observed (%) |
|---|---|---|---|
| Example I-2-b-1 | 100 | 20 | 60 |
| | 50 | 10 | 40 |
| | 25 | | 20 |
| Example I-2-b-1 + mefenpyr | 100 + 100 | 10 | 15 |
| | 50 + 100 | 0 | 10 |
| | 25 + 100 | | 5 |

TABLE 7'

| | Application rate g a.i./ha | Spring barley observed (%) |
|---|---|---|
| Example I-2-b-6 | 100 | 98 |
| | 50 | 97 |
| | 25 | 50 |
| Example I-2-b-6 + mefenpyr | 100 + 100 | 20 |
| | 50 + 100 | 15 |
| | 25 + 100 | 10 |

TABLE 8'

| | Application rate g a.i./ha | Spring wheat observed (%) |
|---|---|---|
| Example I-1-c-1 | 100 | 70 |
| | 50 | 20 |
| | 25 | 20 |
| Example + mefenpyr | 100 + 100 | 55 |
| | 50 + 100 | 5 |
| | 25 + 100 | 5 |

TABLE 9'

| | Application rate g a.i./ha | Spring barley observed (%) | Spring wheat observed (%) |
|---|---|---|---|
| Example I-2-b-4 | 100 | 80 | |
| | 25 | | 100 |
| Example I-2-b-4 + mefenpyr | 100 + 100 | 20 | |
| | 25 + 100 | | 20 |

TABLE 10'

| | Application rate g a.i./ha | Spring barley observed (%) | Spring wheat observed (%) |
|---|---|---|---|
| Example I-2-b-5 | 100 | 100 | |
| | 50 | 97 | |
| | 25 | 50 | 99 |
| Example I-2-b-5 + mefenpyr | 100 + 100 | 30 | |
| | 50 + 100 | 20 | |
| | 25 + 100 | 10 | 20 |

Greenhouse Experiment with Cereals with 100 g a.i./ha Mefenpyr, Post-Emergence; Evaluation 21 Days After Application

TABLE 11'

| | Application rate g a.i./ha | Winter barley (%) | Winter wheat (%) |
|---|---|---|---|
| Example I-1-a-6 | 50 | 20 | 10 |
| Example I-1-a-6 + mefenpyr | 50 + 100 | 0 | 3 |

Container Experiments with Cereals Outside the Greenhouse

Herbicide: mefenpyr 1:2 tank mix

TABLE F'-1

| | Application rate g a.i./ha | Spring barley observed (%) | Spring wheat observed (%) |
|---|---|---|---|
| Example I-2-a-2 | 50 | 20 | 95 |
| Example I-2-a-2 + mefenpyr | 50 + 100 | 5 | 15 |

TABLE F'-2

| | Application rate g a.i./ha | Spring barley observed (%) | Spring wheat observed (%) |
|---|---|---|---|
| Example I-2-c-1 | 100 | 15 | 40 |
| Example I-2-c-1 + mefenpyr | 100 + 200 | 0 | 5 |

TABLE F'-3

| | Application rate g a.i./ha | Spring barley observed (%) | Spring wheat observed (%) |
|---|---|---|---|
| Example I-2-c-2 | 100 | 100 | 100 |
| Example I-2-c-2 + mefenpyr | 100 + 200 | 15 | 70 |

TABLE F'-4

| | Application rate g a.i./ha | Spring barley observed (%) | Spring wheat observed (%) |
|---|---|---|---|
| Example I-2-b-1 | 100 | 20 | 30 |
| Example I-2-b-1 + mefenpyr | 100 + 200 | 0 | 0 |

TABLE F'-5

| | Application rate g a.i./ha | Spring barley observed (%) | Spring wheat observed (%) |
|---|---|---|---|
| Example I-2-b-6 | 50 | 40 | 100 |
| Example I-2-b-6 + mefenpyr | 50 + 100 | 10 | 15 |

TABLE F'-6

| | Application rate g a.i./ha | Spring barley observed (%) | Spring wheat observed (%) |
|---|---|---|---|
| Example I-1-c-1 | 100 | 98 | 98 |
| Example I-1-c-1 + mefenpyr | 160 + 200 | 20 | 65 |

TABLE F'-7

| | Application rate g a.i./ha | Spring barley observed (%) |
|---|---|---|
| Example I-1-b-4 | 50 | 60 |
| Example I-1-b-4 + mefenpry | 50 + 100 | 15 |

Container Experiments with Cereals Outside the Greenhouse

Herbicide : mefenpyr g a.i./ha : 50 g a.i./ha

TABLE F'-8

| | Application rate g a.i./ha | Spring barley observed (%) |
|---|---|---|
| Example I-2-c-2 | 100 | 98 |
| Example I-2-c-2 + mefenpyr | 100 + 50 | 25 |

TABLE F'-9

| | Application rate g a.i./ha | Spring barley observed (%) | Spring wheat observed (%) |
|---|---|---|---|
| Example I-2-c-1 | 100 | 50 | 65 |
| Example I-2-c-1 + mefenpyr | 100 + 50 | 5 | 5 |

Example D

| *Aphis* test, contact action | |
|---|---|
| Solvent: | 7 parts by weight of dimethylformamide |
| Emulsifier: | 1 part by weight of alkylaryl polyglycol ether |

To prepare a suitable active compound preparation, 1 part by weight of active compound is mixed with the stated amounts of solvent and emulsifier and the concentrate is diluted with water to the desired concentration.

Shoots of young field bean plants (*Vicia faba*) which are severely infested with black bean aphids (*Aphis fabae*) are treated by being dipped into the active compound preparation of the desired concentration.

After the desired period of time, the destruction is determined in %. 100% means that all of the aphids have been destroyed; 0% means that no aphids have been destroyed.

In this test, for example the following compounds of the Preparation Examples show a good activity:

TABLE D

Plant-injurious insects
*Aphis fabae* contact test

| Active compounds | Active compound concentration in ppm | Destruction in % after 6 d |
|---|---|---|
| Ex. I-1-a-1 | 1000 | 100 |

Example E

*Meloidogyne* test

| | |
|---|---|
| Solvent: | 7 parts by weight of dimethylformamide |
| Emulsifier | 1 part by weight of alkylaryl polyglycol ether |

To prepare a suitable active compound preparation, 1 part by weight of active compound is mixed with the stated amounts of solvent and emulsifier and the concentrate is diluted with water to the desired concentration.

Containers are filled with sand, active compound solution, Meloidogyne incognita egg/larval suspension and lettuce seeds. The lettuce seeds germinate and the plantlets develop. The galls develop on the roots.

After the desired time, the nematicidal efficacy is determined I n % with reference to gall formation. 100% means that no galls were found; 0% means that the number of galls on the treated plants corresponds to that of the untreated control.

In this test, good activity is shown, for example, by the following compounds of the Preparation Examples:

TABLE E

Plant-injurious nematodes
*Meloidogyne* test

| Active compounds | Active compound concentration in ppm | Destruction in % after 14 d |
|---|---|---|
| Ex. I-1-a-3 | 20 | 98 |
| Ex. I-1-a-4 | 20 | 98 |

Example F

*Myzus* test

| | |
|---|---|
| Solvent: | 7 parts by weight of dimethylformamide |
| Emulsifier | 1 part by weight of alkylaryl polyglycol ether |

To prepare a suitable active compound preparation, 1 part by weight of active compound is mixed with the stated amounts of solvent and emulsifier and the concentrate is diluted with emulsifier-containing water to the desired concentration.

Cabbage leaves (*Brassica oleracea*), which are severely infested with the green peach aphid (*Myzus persicae*) are treated by immersing them into the active compound preparation of the desired concentration.

After the desired time, the destruction rate is determined in %. 100% means that all of the aphids have been destroyed; 0% means that none of the aphids have been destroyed.

In this test, good activity is shown, for example, by the following compounds of the Preparation Examples:

TABLE F

Plant-injurious insects
*Myzus* test

| Active compounds | Active compound concentration in ppm | Destruction in % after 6 d |
|---|---|---|
| Ex. I-1-a-1 | 1000 | 95 |
| Ex. I-1-a-2 | 1000 | 100 |
| Ex. I-1-a-3 | 1000 | 90 |

Example G

*Nephotettix* test

| | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by being dipped into the preparation of active compound of the desired concentration and are infested with the green rice leafhopper (*Nephotettix cincticeps*) while the leaves are still moist.

After the desired time, the destruction in % is determined. 100% means that all the leafhoppers have been killed; 0% means that none of the leafhoppers have been killed.

In this test, for example the following compounds of the preparation examples show good effectiveness:

TABLE G

Plant-injurious insects
*Nephotettix* test

| Active compounds | Active compound concentration in ppm | Destruction in % after 6 d |
|---|---|---|
| Ex. I-1-a-1 | 1000 | 100 |
| Ex. I-1-a-2 | 1000 | 100 |

Example H

*Phaedon* larvae test

| | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are infested with the larvae of the mustard beetle (*Phaedon cochleariae*) while the leaves are still moist.

After the desired time, the destruction in % is determined. 100% means that all the beetle larvae have been killed; 0% means that none of the beetle larvae have been killed.

In this test, for example the following compounds of the preparation examples show good effectiveness:

TABLE H

Plant-injurious insects
*Phaedon larvae* test

| Active compounds | Active compound concentration in ppm | Destruction in % after 7 d |
| --- | --- | --- |
| Ex. I-1-a-1 | 1000 | 100 |
| Ex. I-1-a-2 | 1000 | 100 |
| Ex. I-1-a-3 | 1000 | 80 |
| Ex. I-1-a-4 | 1000 | 100 |
| Ex. I-1-a-6 | 1000 | 90 |

Example I

| *Plutella* test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are infested with caterpillars of the diamond-back moth (*Plutella xylostella*) while the leaves are still moist.

After the desired time, the destruction in % is determined. 100% means that all the caterpillars have been killed; 0% means that none of the caterpillars have been killed.

In this test, for example the following compounds of the preparation examples show good effectiveness:

TABLE I

Plant-injurious insects
*Plutella* test

| Active compounds | Active compound concentration in ppm | Destruction in % after 7 d |
| --- | --- | --- |
| Ex. I-1-a-1 | 1000 | 100 |
| Ex. I-1-a-2 | 1000 | 100 |

Example J

| *Spodoptera frugiperda* test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are infested with caterpillars of the armyworm (*Spodoptera frugiperd*) while the leaves are still moist.

After the desired time, the destruction in % is determined. 100% means that all the caterpillars have been killed; 0% means that none of the caterpillars have been killed.

In this test, for example the following compounds of the preparation examples show good effectiveness:

TABLE J

Plant-injurious insects
*Spodoptera frugiperda* test

| Active compounds | Active compound concentration in ppm | Destruction in % after 7 d |
| --- | --- | --- |
| Ex. I-1-a-1 | 1000 | 100 |

Example K

| *Tetranychus* test (OP-resistant/immersion treatment) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are severely infested with all stages of the greenhouse red spider mite (*Tetranychus urticae*) are dipped into a preparation of the active compound of the desired concentration.

After the desired time, the activity in % is determined. 100% means that all the spider mites have been killed; 0% means that none of the spider mites have been killed.

In this test, for example the following compounds of the preparation examples show good effectiveness:

TABLE K

Plant-injurious mites
*Tetranychus* test (OP-resistant/immersion treatment)

| Active compounds | Active compound concentration in ppm | Destruction in % after 7 d |
| --- | --- | --- |
| Ex. I-1-a-1 | 1000 | 100 |
| Ex. I-1-a-2 | 1000 | 95 |
| Ex. I-1-a-3 | 100 | 80 |

Example L

| Limit concentration test/soil-dwelling insects—treatment of transgenic plants | |
|---|---|
| Test insect: | *Diabrotica balteata* — larvae in the soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added, and the concentrate is diluted with water to the desired concentration.

The active compound preparation is poured on the soil. The concentration of the active compound in the preparation is of virtually no importance, only the amount of weight of active compound per unit volume of soil, which is detailed in ppm (mg/l), being decisive. 0.25 l pots are filled with the soil and left to stand at 20° C.

Immediately after setting up the experiment, 5 pregerminated maize kernels cv. YIELD GUARD (trade mark of Monsanto Comp., USA) are placed into each pot. After 2 days, the test insects in question are placed into the treated soil. After a further 7 days, the efficacy of the active compound is determined by counting the maize plants which have emerged (1 plant=20% activity).

Example M

| *Heliothis virescens* test — treatment of transgenic plants | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Soybean shoots (Glycine max) cv. Roundup Ready (trade mark of Monsanto Comp. USA) are treated by dipping them into the active compound preparation of the desired concentration and are populated with caterpillars of the tobacco budworm (Heliothis virescens) while the leaves are still moist.

After the desired time, the destruction of the insects is determined.

The invention claimed is:
1. A compound of formula (I)

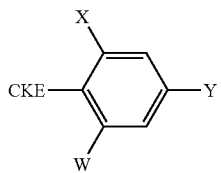

(I)

in which
W represents methoxy, ethoxy, n-propoxy, iso-propoxy, n-butoxy, iso-butoxy, sec-butoxy, methoxy-ethyloxy, ethoxy-ethyloxy, or cyclopropylmethoxy,
X represents methyl or ethyl,
Y represents chlorine,
CKE represents a group

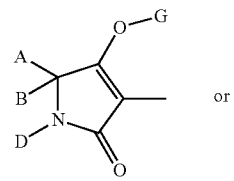

(1)

or

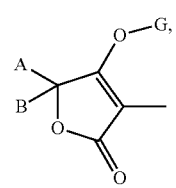

(2)

in which
A represents hydrogen, methyl, ethyl, cyclopropyl, iso-propyl, n-propyl, isobutyl, n-butyl, t-butyl or s-butyl,
B represents hydrogen, methyl, or ethyl,
A, B and the carbon atom to which they are bonded represent saturated $C_5$-$C_6$-cycloalkyl in which one ring member is optionally replaced by oxygen and that is optionally monosubstituted by methyl, methoxy, ethoxy, n-propoxy, n-butoxy, or trifluoromethyl,
D represents hydrogen, methyl, ethyl, isopropyl, cyclopropyl, or cyclohexyl, or
A and D together represent $C_3$-$C_5$-alkanediyl, and
G represents hydrogen or a group

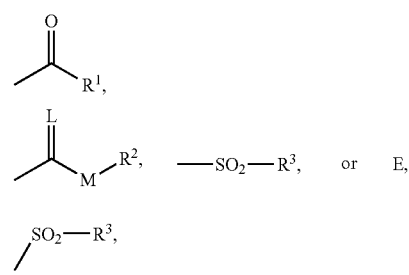

(d)

in which
L represents oxygen,
M represents oxygen,
E represents an ammonium ion ($N^+(C_6H_{13})_4$),
$R^1$ represents $C_1$-$C_8$-alkyl, $C_1$-$C_2$-alkoxy-$C_1$-alkyl, or $C_2$-$C_{17}$-alkenyl,
$R^2$ represents $C_1$-$C_8$-alkyl or $C_2$-$C_6$-alkenyl, and
$R^3$ represents $C_1$-$C_4$-alkyl.

2. A process for the preparation of compounds of formula (I)

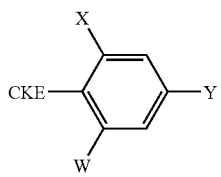

in which
W represents alkoxy, halogenoalkoxy, alkoxyalkyloxy, alkoxy-bis-alkyloxy, or optionally substituted cycloalkylalkanediyloxy that is optionally interrupted by hetero atoms,
X represents alkyl,
Y represents chlorine, bromine, or iodine, and
CKE represents a group

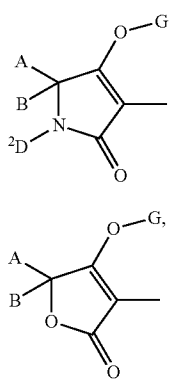

in which
A represents hydrogen; represents alkyl, alkenyl, alkoxyalkyl, or alkyl-thioalkyl, each of which is optionally substituted by halogen; represents saturated or unsaturated, optionally substituted cycloalkyl in which one or more ring atoms are optionally replaced by a hetero atom; or represents aryl, arylalkyl, or hetaryl, each of which is optionally substituted by halogen, alkyl, halogenoalkyl, alkoxy, halogenoalkoxy, cyano, or nitro,
B represents hydrogen, alkyl, or alkoxyalkyl, or
A and B together with the carbon atom to which they are bonded represent a saturated or unsaturated, unsubstituted or substituted cycle that optionally contains one or more hetero atoms,
D represents hydrogen; represents an optionally substituted radical selected from the series consisting of alkyl, alkenyl, alkynyl, alkoxyalkyl, and saturated or unsaturated cycloalkyl in which one or more ring members are optionally replaced by hetero atoms; or represents arylalkyl, aryl, hetarylalkyl, or hetaryl, or
A and D together with the atoms to which they are bonded represent a saturated or unsaturated cycle that is unsubstituted or substituted in the A,D moiety and optionally contains one or more hetero atoms, and
G represents hydrogen or a group

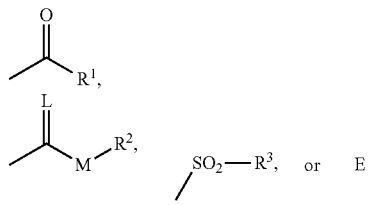

in which
E represents a metal ion equivalent or an ammonium ion,
L represents oxygen or sulphur,
M represents oxygen or sulphur,
$R^1$ represents alkyl, alkenyl, alkoxyalkyl, alkylthioalkyl, or poly-alkoxyalkyl, each of which is optionally substituted by halogen; represents cycloalkyl that is optionally interrupted by one or more hetero atoms and is optionally substituted by halogen, alkyl, or alkoxy; or represents optionally substituted phenyl, phenylalkyl, hetaryl, phenoxyalkyl, or hetaryloxyalkyl, and
$R^2$ represents alkyl, alkenyl, alkoxyalkyl, or poly-alkoxyalkyl, each of which is optionally substituted by halogen; or represents optionally substituted cycloalkyl, phenyl, or benzyl,
$R^3$ represents alkyl, alkoxy, alkylamino, dialkylamino, alkylthio, alkenylthio, or cycloalkyl-thio, each of which is optionally substituted by halogen; or represents optionally substituted phenyl, benzyl, phenoxy, or phenylthio,
comprising
(A) for compounds of formula (I-1-a)

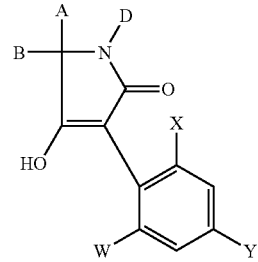

in which A, B, D, W, X, and Y have the meanings given for formula (I), subjecting to an intramolecular condensation reaction a compound of formula (II)

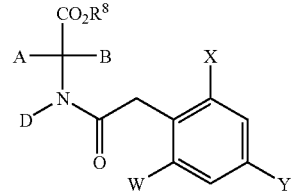

in which
A, B, D, W, X, and Y have the meanings given for formula (I), and $R^8$ represents alkyl, in the presence of a diluent and in the presence of a base, or (B) for compounds of formula (I-2-a)

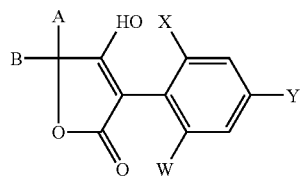
(I-2-a)

in which A, B, W, X and Y have the meanings given for formula (I), subjecting to an intramolecular condensation reaction a compound of formula (III)

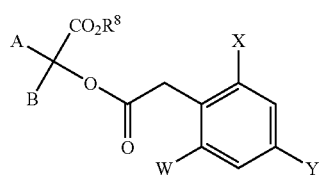
(III)

in which A, B, W, X, Y, and $R^8$ have the meanings given for formula (I), in the presence of a diluent and in the presence of a base.

and (C) for compounds of formulas (I-1-b) to (I 2 b)

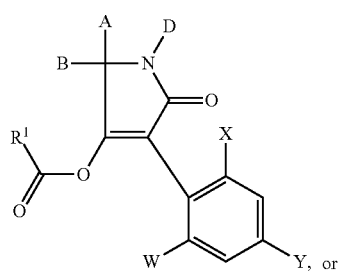
(I-1-b)

(I-2-b)

in which A, B, D, $R^1$, W, X, and Y have the meanings given for formula (I), reacting compounds of formulas (I-1-a) to (I 2 a) shown above in which A, B, D, W, X and Y have the meanings given for formula (I), (α) with an acid chloride of formula (XIII)

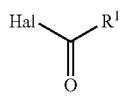
(XIII)

in which $R^1$ has the meanings given for formula (I), and

Hal represents halogen, or (β) with a carboxylic anhydride of formula (XIV)

$R^1$—CO—O—CO—$R^1$ (XIV)

in which $R^1$ has the meanings given for formula (I), optionally in the presence of a diluent and optionally in the presence of an acid-binding agent;

(D) for compounds of formulas (I-1-c) to (I 2 c)

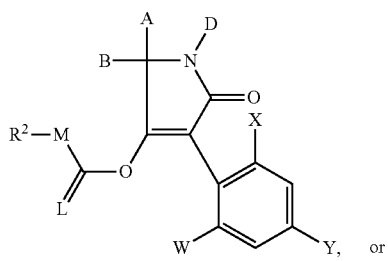
(I-1-c)

(I-2-c)

in which

A, B, D, $R^2$, M, W, X, and Y have the meanings given for formula (I), and

L represents oxygen, reacting compounds of formulas (I-1-a) to (I 2 a) shown above in which A, B, D, W, X and Y have the meanings given for formula (I), with a chloroformic ester or chloroformic thioester of formula (XV)

$R^2$-M-CO—Cl (XV)

in which $R^2$ and M have the meanings given for formula (I), optionally in the presence of a diluent and optionally in the presence of an acid-binding agent;

or (E) for compounds of formulas (I-1-c) to (I 2 c)

in which

A, B, D, $R^2$, M, W, X, and Y have the meanings given for formula (I), and

L represents sulphur, reacting compounds of formulas (I-1-a) to (I 2 a) shown above in which A, B, D, W, X and Y have the meanings given for formula (I), with a chloromonothioformic ester or chlorodithioformic ester of formula (XVI)

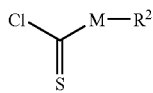
(XVI)

in which R² and M have the meanings given for formula (I), optionally in the presence of a diluent and optionally in the presence of an acid-binding agent;

or (F) for compounds of formulas (I-1-d) to (I 2 d)

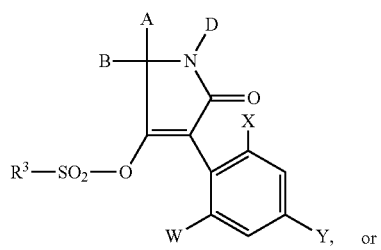
(I-1-d)

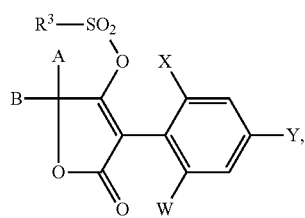
(I-2-d)

in which A, B, D, R³, W, X and Y have the meanings given for formula (I), reacting compounds of formulas (I-1-a) to (I 2 a) shown above in which A, B, D, W, X and Y have the meanings given for formula (I), with a sulphonyl chloride of formula (XVII)

R³—SO₂—Cl (XVII)

in which R³ has the meanings given for formula (I), optionally in the presence of a diluent and optionally in the presence of an acid-binding agent;

or (G) for compounds of formulas (I-1-f) to (I 2 f)

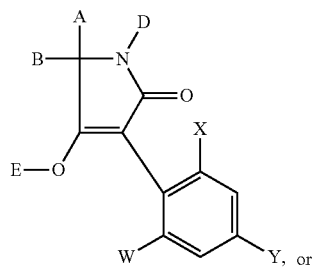
(I-1-f)

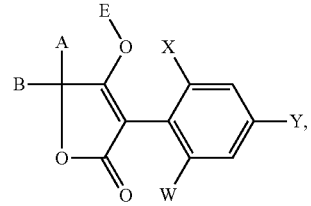
(I-2-f)

in which A, B, D, E, W, X and Y have the meanings given for formula (I), reacting compounds of formulas (I-1-a) to (I 2 a) shown above in which A, B, D, W, X and Y have the meanings given for formula (I), (α) with a metal compound of formula (XIX)

Me(OR¹⁰)$_t$ (XIX)

in which

Me represents a mono- or divalent metal, and t represents the number 1 or 2, optionally in the presence of a diluent, or (β) with an amine of formulae (XX)

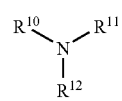
(XX)

in which R¹⁰, R¹¹ and R¹² independently of one another represent hydrogen or alkyl, optionally in the presence of a diluent.

3. A composition comprising the components, (a') one or more substituted cyclic ketoenols of formula (I) according to claim 1, and (b') one or more compounds selected from the group consisting of the compounds 4-dichloroacetyl-1-oxa-4-aza-spiro[4.5]-decane (AD-67, MON-4660), 1-dichloro-acetyl-hexahydro-3,3,8a-trimethyl-pyrrolo [1,2-a]-pyrimidin-6(2H)-one (dicyclonon, BAS-145138), 4-dichloroacetyl -3,4-dihydro-3-methyl-2H-1,4-benzoxazine (benoxacor), 1-methyl-hexyl 5-chloro -quinolin-8-oxy-acetate (cloquintocet-mexyl), 3-(2-chloro-benzyl)-1-(1-methyl-1-phenyl-ethyl) -urea (cumyluron), α-(cyanomethoximino)-phenylacetonitrile (cyometrinil), 2,4-dichloro-phenoxyacetic acid (2,4-D), 4-(2,4-dichloro -phenoxy)-butyric acid (2,4-DB), 1-(1-methyl-1-phenyl-ethyl)-3-(4-methyl-phenyl)-urea (daimuron, dymron), 3,6-dichloro-2-methoxy-benzoic acid (dicamba), S-1-methyl -1-phenyl-ethyl piperidine-1-thiocarboxylate (dimepiperate), 2,2-dichloro-N -(2oxo-2(2-propenylamino)-ethyl)-N-(2-propenyl)-acetamide (DKA-24), 2,2-dichloro -N,N-di-2-propenyl-acetamide (dichlormid), 4,6-dichloro-2-phenyl-pyrimidine (fenclorim), ethyl 1-(2,4-dichloro-phenyl)-5-trichloro-methyl-1H-1,2,4-triazole-3-carboxylate (fenchlorazole-ethyl), phenylmethyl 2-chloro-4-trifluoromethyl-thiazole -5-carboxylate (flurazole), 4-chloro-N-(1,3-dioxolan-2-yl-methoxy)-α-trifluoro-acetophenone oxime (fluxofenim), 3-dichloroacetyl-5-(2-furanyl) -2,2-dimethyl-oxazolidine (furilazole, MON-13900), ethyl 4,5-dihydro-5,5-diphenyl -3-isoxazolecarboxylate (isoxadifen-ethyl, 1-(ethoxycarbonyl)-ethyl-3,6-dichloro-2-methoxybenzoate (lactidichlor), (4-chloro-o-tolyloxy)-acetic acid (MCPA), 2-(4-chloro-o-tolyloxy) -propionic acid (mecoprop), diethyl 1-(2,4-dichloro-phenyl) -4,5-dihydro -5-methyl-1H-pyrazole-3,5-dicarboxylate (mefenpyr-diethyl), 2-dichloromethyl-2-methyl-1,3-dioxolane (MG-191), 2-propenyl-1-oxa -4-azaspiro [4.5]decane 4-carbodithioate (MG-838), 1,8-naphthalic anhydride, α-(1,3-dioxolan-2-yl-methoximino)-phenylacetonitrile (oxabetrinil), 2,2-dichloro-N -(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chloro -phenoxy)-butyric acid, diphenylmethoxyacetic acid, methyl diphenylmethoxyacetate, ethyl diphenylmethoxyacetate, methyl 1-(2chloro-phenyl) -5-phenyl-1H-pyrazole-3-carboxylate, ethyl 1-(2,4-dichloro -phenyl)-5-methyl-1H-pyrazole-3-carboxylate, ethyl 1-(2,4-dichloro-phenyl)-5-isopropyl-1H -pyrazole-3-carboxylate, ethyl 1-(2,4-dichloro-phenyl)-5-(1,1-dimethyl-ethyl)-1H -pyrazole-3-carboxylate, ethyl 1-(2, 4-dichloro-phenyl)-5-phenyl-1H -pyrazole-3-carboxylate, ethyl 5-(2,4-dichloro-benzyl)-2-isoxazoline-3-carboxylate, ethyl 5-phenyl - 2-isoxazoline-3-carboxylate, ethyl 5-(4-fluoro-phenyl)-5-phenyl-2-isoxazoline-3-carboxylate, 1,3-dimethyl-but-1-yl 5-chloro-quinolin-8-oxy-acetate, 4-allyloxybutyl 5-chloro-quinolin-8-oxy-acetate, 1-allyloxyprop-2-yl 5-chloro-quinolin -8-oxy-acetate, methyl 5-chloro-quinolin-8-oxy-acetate, ethyl 5-chloro -quinolin-8-oxy-acetate, allyl 5-chloro-quinoxalin-8-oxy-acetate, 2-oxo -prop-1-yl 5-chloro-quinolin-8-oxy-acetate, diethyl 5-chloroquinolin-8-oxy-malonate, diallyl 5-chloro-quinoxalin-8-oxy-malonate, diethyl 5-chloro-quinolin-8-oxy-malonate, 4-carboxy-chroman-4-yl-acetic acid (AC-304415), 4-chloro-phenoxy-acetic acid, 3,3'-dimethyl-4-methoxy-benzophenone, 1-bromo-4-chloromethylsulphonyl -benzene, 1-[4-(N-2-methoxybenzoylsulphamoyl)-phenyl]-3-methyl-urea (alias N - (2-methoxy-benzoyl)-4-[(methylamino-carbonyl)-amino]-benzenesulphonamide), 1-[4-(N-2-methoxybenzoylsulphamoyl)-phenyl]-3,3-dimethyl-urea, 1-[4-(N-4,5-dimethylbenzoylsulphamoyl)-phenyl]-3-methyl-urea, 1-[4-(N-naphthylsulphamoyl) -phenyl]-3, 3-dimethyl-urea, N-(2-methoxy-5-methyl-benzoyl) -4- (cyclopropylaminocarbonyl)-benzenesulphonamide, a compound of formula (IIa)

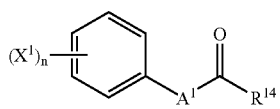
(IIa)

in which $X^1$ represents nitro, cyano, halogen, $C_1$-$C_4$-alkyl, $C_1$-$C_4$ halogenoalkyl, $C_1$-$C_4$-alkoxy, or $C_1$-$C_4$-halogenoalkoxy; n represents a number of between 0 and 5; $A^I$ represents a divalent heterocyclic group of the formulas

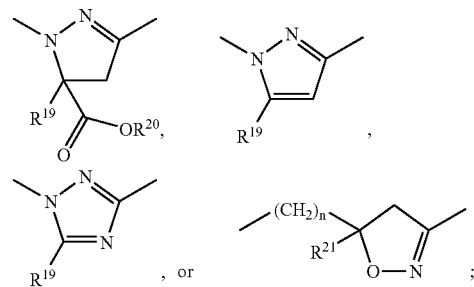

$R^{19}$ represents hydrogen, cyano, or halogen or represents $C_1$-$C_4$-alkyl, $C_3$-$C_6$-cycloalkyl or phenyl, each of which is optionally substituted by fluorine, chlorine, and/or bromine; $R^{20}$ represents hydrogen or represents $C_1$-$C_6$-alkyl, $C_3$-$C_6$-cycloalkyl, or tri($C_1$-$C_4$-alkyl)silyl, each of which is optionally substituted by hydroxyl, cyano, halogen, or $C_1$-$C_4$-alkoxy; $R^{21}$ represents hydrogen, cyano, or halogen or represents $C_1$-$C_4$-alkyl, $C_3$-$C_6$-cycloalkyl, or phenyl, each of which is optionally substituted by fluorine, chlorine, and/or bromine; and $R^{14}$ represents hydroxyl, mercapto, amino, $C_1$-$C_6$-alkoxy, $C_1$-$C_6$-alkylthio, $C_1$-$C_6$-alkylamino, or di($C_1$-$C_4$-alkyl)amino,
a compound of formula (IIb)

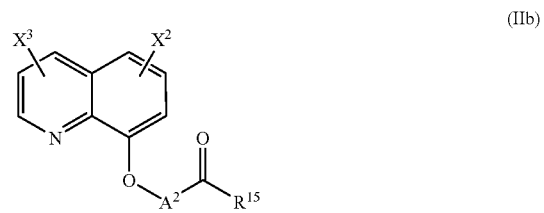
(IIb)

in which $X^2$ represents hydrogen, cyano, nitro, $C_1$-$C_4$-alkyl, $C_1$-$C_4$-halogenoalkyl, $C_1$-$C_4$-alkoxy, or $C_1$-$C_4$-halogenoalkoxy; $X^3$ represents hydrogen, cyano, nitro, $C_1$-$C_4$-alkyl, $C_1$-$C_4$-halogenoalkyl, $C_1$-$C_4$-alkoxy, or $C_1$-$C_4$-halogenoalkoxy; $A^2$ represents alkanediyl having 1 or 2 carbon atoms that is optionally substituted by $C_1$-$C_4$-alkyl and/or $C_1$-$C_4$-alkoxy-carbonyl; and $R^{15}$ represents hydroxyl, mercapto, amino, $C_1$-$C_6$-alkoxy, $C_1$-$C_6$-alkylthio, $C_1$-$C_6$-alkylamino, or di($C_1$-$C_4$-alkyl)amino,
a compound of formula (IIc)

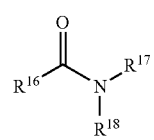
(IIc)

in which $R^{16}$ represents $C_1$-$C_4$-alkyl that is optionally substituted by fluorine, chlorine and/or bromine; $R^{17}$ represents hydrogen, represents $C_1$-$C_6$-alkyl, $C_2$-$C_6$-alkenyl, $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl, each of which is optionally substituted by fluorine, chlorine, and/or bromine, or represents phenyl that is optionally substituted by fluorine, chlorine, and/or bromine or $C_1$-$C_4$-alkyl; and $R^{18}$ represents hydrogen or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl, each of which is optionally substituted by fluorine, chlorine, and/or bromine, or represents phenyl that is optionally substituted by fluorine, chlorine, and/or bromine or $C_1$-$C_4$-alkyl, or $R^{18}$ together with $R^{17}$ represents $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are bonded, form a 5- or 6-membered carbocycle, a compound of formula (IId)

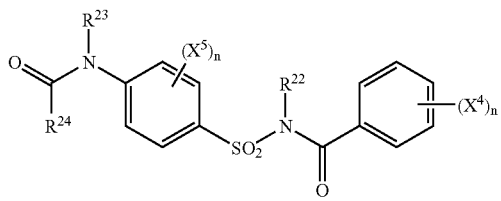

(IId)

in which $X^4$ represents nitro, cyano, carboxyl, carbamoyl, formyl, sulphamoyl, hydroxyl, amino, halogen, $C_1$-$C_4$-alkyl, $C_1$-$C_4$-halogenoalkyl, $C_1$-$C_4$-alkoxy, or $C_1$-$C_4$-halogenoalkoxy; $X^5$ represents nitro, cyano, carboxyl, carbamoyl, formyl, sulphamoyl, hydroxyl, amino, halogen, $C_1$-$C_4$-alkyl, $C_1$-$C_4$-halogenoalkyl, $C_1$-$C_4$-alkoxy, or $C_1$-$C_4$-halogenoalkoxy; n represents a number of between 0 and 5; $R^{22}$ represents hydrogen or $C_1$-$C_4$-alkyl; $R^{23}$ represents hydrogen or $C_1$-$C_4$-alkyl; and $R^{24}$ represents hydrogen, represents $C_1$-$C_6$-alkyl, $C_1$-$C_6$-alkoxy, $C_1$-$C_6$-alkylthio, $C_1$-$C_6$-alkylamino, or di($C_1$-$C_4$-alkyl)amino, each of which is optionally substituted by cyano, halogen, or $C_1$-$C_4$-alkoxy, or represents $C_3$-$C_6$-cycloalkyl, $C_3$-$C_6$-cycloalkyloxy, $C_3$-$C_6$-cycloalkylthio, or $C_3$-$C_6$-cycloalkylamino, each of which is optionally substituted by cyano, halogen, or $C_1$-$C_4$-alkyl, or a compound of formula (IIe)

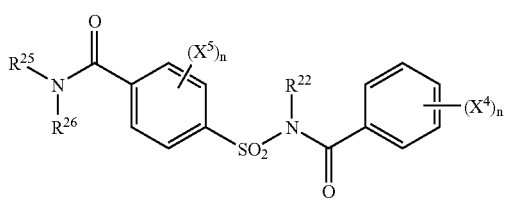

(IIe)

in which $X^4$ represents nitro, cyano, carboxyl, carbamoyl, formyl, sulphamoyl, hydroxyl, amino, halogen, $C_1$-$C_4$-alkyl, $C_1$-$C_4$-halogenoalkyl, $C_1$-$C_4$-alkoxy, or $C_1$-$C_4$-halogenoalkoxy; $X^5$ represents nitro, cyano, carboxyl, carbamoyl, formyl, sulphamoyl, hydroxyl, amino, halogen, $C_1$-$C_4$-alkyl, $C_1$-$C_4$-halogenoalkyl, $C_1$-$C_4$-alkoxy, or $C_1$-$C_4$-halogenoalkoxy; n represents a number of between 0 and 5; $R^{22}$ represents hydrogen or $C_1$-$C_4$-alkyl; $R^{25}$ represents hydrogen, represents $C_1$-$C_6$-alkyl that is optionally substituted by cyano, hydroxyl, halogen, or $C_1$-$C_4$-alkoxy, represents $C_3$-$C_6$-alkenyl or $C_3$-$C_6$-alkynyl, each of which is optionally substituted by cyano or halogen, or represents $C_3$-$C_6$-cycloalkyl that is optionally substituted by cyano, halogen, or $C_1$-$C_4$-alkyl; $R^{26}$ represents hydrogen, represents $C_1$-$C_6$-alkyl that is optionally substituted by cyano, hydroxyl, halogen, or $C_1$-$C_4$-alkoxy, represents $C_3$-$C_6$-alkenyl or $C_3$-$C_6$-alkynyl, each of which is optionally substituted by cyano or halogen, represents $C_3$-$C_6$-cycloalkyl which is optionally substituted by cyano, halogen or $C_1$-$C_4$-alkyl, or represents phenyl that is optionally substituted by nitro, cyano, halogen, $C_1$-$C_4$-alkyl, $C_1$-$C_4$-halogenoalkyl, $C_1$-$C_4$-alkoxy, or $C_1$-$C_4$-halogenoalkoxy, or $R^{26}$ together with $R^{25}$ represents $C_2$-$C_6$-alkanediyl or $C_2$-$C_5$-oxaalkanediyl, each of which is optionally substituted by $C_1$-$C_4$-alkyl.

4. A composition according to claim 3, in which component (b') is selected from the group consisting of the compounds cloquintocet-mexyl, fenchlorazole-ethyl, isoxadifen-ethyl, mefenpyr-diethyl, furilazole, fenclorim, cumyluron, dymron, the compound

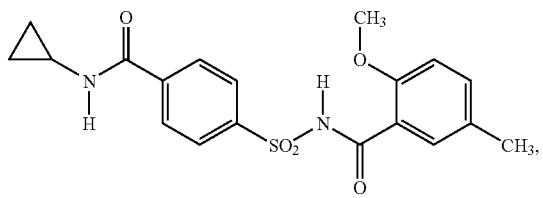

and the compound

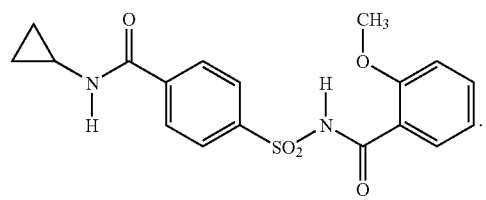

5. A composition according to claim 3 in which component (b') is cloquintocet-mexyl or mefenpyr-diethyl.

6. A pesticide and/or herbicide comprising one or more compounds of formula (I) according to claim 1.

7. A method for controlling animal pests comprising allowing an effective amount of one or more compounds of formula (I) according to claim 1 to act on pests and/or their environment.

8. A method for controlling undesired vegetation comprising allowing an effective amount of one or more compounds of formula (I) according to claim 1 to act on plants and/or their environment.

9. A process for the preparation of a pesticide and/or herbicide comprising mixing one or more compounds of formula (I) according to claim 1 with one or more extenders and/or surface-active substances.

10. A method for controlling undesired vegetation comprising allowing an effective amount of a composition according to claim 3 to act on plants and/or their environment.

11. A method for controlling undesired vegetation according to claim 10 in which components (a') and (b') of claim 3 are allowed to act separately at short intervals on plants and/or their environment.

* * * * *